United States Patent [19]

Christensen, IV et al.

[11] Patent Number: 6,037,367
[45] Date of Patent: Mar. 14, 2000

[54] SUBSTITUTED-PENT-4-YNOIC ACIDS

[75] Inventors: Siegfried B. Christensen, IV, Philadelphia; Joseph M. Karpinski, Douglassville, both of Pa.; James S. Frazee, Sewell, N.J.

[73] Assignee: SmithKline Beecham Corporation, Philadelphia, Pa.

[21] Appl. No.: 08/716,359

[22] PCT Filed: Jul. 12, 1996

[86] PCT No.: PCT/US96/11613

§ 371 Date: Sep. 14, 1998

§ 102(e) Date: Sep. 14, 1998

[87] PCT Pub. No.: WO97/03945

PCT Pub. Date: Feb. 6, 1997

Related U.S. Application Data

[60] Provisional application No. 60/001,196, Jul. 14, 1995, and provisional application No. 60/016,717, May 2, 1996.

[51] Int. Cl.$^7$ .......................... A61K 31/19; C07C 69/736
[52] U.S. Cl. .......................... 514/530; 514/570; 544/174; 544/332; 544/394; 548/131; 548/136; 548/143; 548/204; 548/253; 548/341.5; 548/479; 548/562; 549/359; 549/461; 549/488; 558/406; 560/9; 560/55; 560/56; 560/60
[58] Field of Search .......................... 544/174, 332, 544/394; 548/131, 136, 143, 204, 253, 341.5, 479, 562; 549/359, 461, 488; 558/406; 560/9, 55, 56, 60; 562/465, 466; 564/171, 344; 568/330, 644; 514/530, 570

[56] References Cited

U.S. PATENT DOCUMENTS 5,274,022 12/1993 Hawkins.

*Primary Examiner*—Robert Gerstl
*Attorney, Agent, or Firm*—James M. Kanagy; Charles M. Kinzig

[57] ABSTRACT

Compounds of formula (I) wherein: $R_1$ is —$(CR_4R_5)_nC(O)O(CR_4R_5)_mR_6$, —$(CR_4R_5)_nC(O)NR_4(CR_4R_5)_mR_6$, $(CR_4R_5)_nO(CR_4R_5)_mR_6$, or —$(CR_4R_5)_rR_6$: W is alkynyl or 2 carbon atoms; $R_3$ is H or $R_7$; Z is $C(O)R_{13}$, $(CH_2)_{0-1}C(O)OR_{13}$, $(CH_2)_{0-1}C(O)NR_{10}R_{13}$, $(CH_2)_{0-1}C(R_8R_8)OR_8$, —$NHC(O)R_7$, $(CH_2)_{0-1}NR_{10}R_{13}$, $NH[C(O)C(O)OR_8]$, $CH_2NH[C(O)CNR_{10}R_{13}]$, $CH_2S(O)_qR_7$, $CH[S(O)_qR_7]_2$, dithiolane, (tetrazol-5-yl), thiazol-2-yl, [1,2,4]thiadiazol-5-yl, [1,3,4]oxadiazol-2-yl, imidazol-2-yl, oxazol-2-yl, or (3- or 5-oxadiazolyl[1,2,4]; $R_7$ is —$(CR_4R_5)_qR_{11}$ or $C_{1-6}$ alkyl wherein the $R_{11}$ or $C_{1-6}$ alkyl group is unsubstituted or substituted one or more times by methyl or ethyl unsubstituted or substituted by 1-3 fluorines, —$NR_8R_{10}$, —$CO_2R_8$, —$O(CH_{2q}R_8$, —$NR_8C(O)R_8$ or $R_{12}$; or the pharmaceutically acceptable salts thereof.

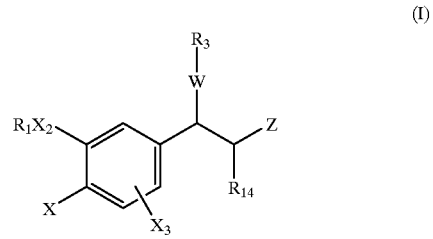

4 Claims, No Drawings

SUBSTITUTED-PENT-4-YNOIC ACIDS

This application is a 371 of PCT/US96/11613 filed Jul. 12, 1996 and also claims the benefit of Provisional Application No. 60/001,196 Jul. 14, 1995 and No. 60/016,717 May 2, 1996.

SCOPE OF THE INVENTION

The present invention relates to novel 3-(1,3, 4trisubstitutedphenyl)-5-substituted-pent-4-ynoic acids and related compounds, pharmaceutical compositions containing these compounds, and their use in treating allergic and inflammatory diseases and for inhibiting the production of Tumor Necrosis Factor (TNF).

BACKGROUND OF THE INVENTION

Bronchial asthma is a complex, multifactorial disease characterized by reversible narrowing of the airway and hyperreactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysioloy of the disease.

One such way is by elevating levels of cAMP (adenosine cyclic 3', 5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysioloy of extrinsic (allergi(c) asthma As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiesterase bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the production of Tumor Necrosis Factor (TNF), a serum glycoprotein. Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, ram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, raft vs. host reaction, allograft rejections, fever and myalgias due to infection, such as influenza, cachexia secondary to infection or malignancy, cachexia secondary to human acquired immune deficiency syndrome (AIDS), AIDS, ARC (AIDS related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell-mediated immunity is impaired and infected individuals manifest severe opportunistic infections and/or unusual neoplasms. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell-mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T cells, are targets for viral replication and the level of viral replication is dependent upon the activation state of the cells. [See Rosenber et al., The Immunopathoenesis of HIV Infection, Advances in Immunology, Vol. 57, 1989]. Monokines, such as TNF, have been shown to activate HIV replication in monocytes and/or macrophages [See Poli et al., Proc. Natl. Acad. Sci., 87:782–784, 1990], therefore, inhibition of monokine production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically Candida albicans has been shown to induce TNF production in vitro in human monocytes and natural killer cells. [See Riipi et al, Infection and Immunity, 58(9):2750–54, 1990; and Jafari et al, Journal of Infectious Diseases, 164:389–95, 1991. See also Wasan et al, Antimicrobial Agents and Chemotherapy, 35,(10):2046–48, 1991; and Luke et al, Journal of Infectious Diseases, 162:211–214, 1990].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

In a first aspect, this invention relates to compounds of Formula (I)

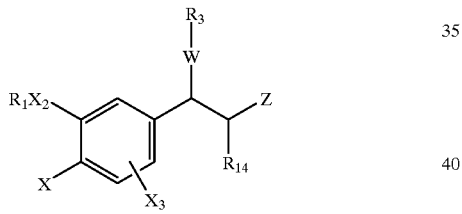

wherein:
$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties unsubstituted or substituted with one or more halogens;
m is 0 to 2;
n is 1 to 4;
r is 0 to 6;
$R_4$ and $R_5$ are independently selected hydrogen or $C_{1-2}$ alkyl;
$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety is unsubstituted or substituted by 1 to 3 methyl groups, one ethyl group, or an hydroxyl group;
provided that:
(a) when $R_6$ is hydroxyl, then m is 2; or
(b) when $R_6$ is hydroxyl, then r is 2 to 6; or
(c) when $R_6$ is 2-tetrahydropyranyl, 2-tetrahydrothiopyranyl, 2-tetrahydrofuranyl, or 2-tetrahydrothienyl, then m is 1 or 2; or
(d) when $R_6$ is 2-tetrahydropyranyl, 2-tetrahydrothiopyranyl, 2-tetrahydrofuranyl,or 2-tetrahydrothienyl, then r is 1 to 6;
e) when n is 1 and m is 0, then $R_6$ is other than H in —$(CR_4R_5)_nO(CR_4R_5)_mR_6$;
X is $YR_2$, fluorine, $NR_4R_5$, or formyl amine;
Y is O or S(O)m';
m' is 0, 1,or2;
$X_2$ is O or $NR_8$;
$X_3$ is hydrogen or X;
$R_2$ is independently selected from —$CH_3$ or —$CH_2CH_3$ optionally substituted by 1 or more halogens;
W is alkyl of 2 to 6 carbons, alkenyl of 2 to 6 carbon atoms or alkynyl of 2 to 6 carbon atoms;
$R_3$ is H or $R_7$;
Z is $C(O)R_{13}$, $(CH_2)_{0-1}C(O)OR_{13}$, $(CH_2)_{0-1}C(O)NR_{10}R_{13}$, $(CH_2)_{0-1}C(R_8R_8)OR_8$, —$NHC(O)R_7$, $(CH_2)_{0-1}NR_{10}R_{13}$, $NH[C(O)C(O)OR_8]$, $NH[C(O)C(O)NR_{10}R_{13}]$, $CH_2S(O)_qR_7$, $CH[S(O)_qR_7]_2$, dithiolanyl, (tetrazol-5-yl), thiazol-2-yl, [1,2,4]thiadiazol-5-yl,[1,3,4]oxadiazol-2-yl, imidazol-2-yl, oxazol-2-yl, oxazolidin-2-yl, or (3- or 5-oxadiazolyl [1,2,4]; wherein each of the heterocylic ring systems are unsubstituted or substituted one or more times by $R_9$;
$R_7$ is —$(CR_4R_5)_qR_{11}$or $C_{1-6}$ alkyl wherein the $R_{11}$ or $C_{1-6}$ alkyl group is unsubstituted or substituted one or more times by methyl or ethyl unsubstituted or substituted by 1–3 fluorines, F, Cl, $NO_2$, —$(CH_2)_qNR_8R_{10}$, —$C(O)R_8$, —$C(O)OR_8$, —$O(CH_2)_qR_8$,— $O(CH_2)_{1-2}CN$, —$(CH_2)_{1-2}O(CH_2)_2OR_8$, —$NR_8C(O)R_8$, phthalimido, pyrrolyl, t-butyl, N-veratrylamino, N-[2-(cyclohexylamino) acetamido]phenyl, N-[2-(1-pyrrolidino)acetamido]phenyl, N-[2-(benzylamino)acetamido]phenyl, methyl 3-(3-cyclopentyloxy4-methoxyphenyl) pent4-ynoatyl)-5-phen4-yl, or $R_{12}$;
q is 0, 1,or2;
$R_8$ is independently selected from hydrogen or $R_9$;
$R_9$ is $C_{1-4}$ alkyl optionally substituted by one to three fluorines;
$R_{10}$ is $OR_8$ or $R_8$;
$R_{11}$ is oxazolyl,pyridinyl, pyrimidyl, (1- or 2-imidazolyl), phenyl, furanyl, naphthyl, fluorenyl, dibenzofuranyl, N-acetylindolinyl, dibenzo-p-dioxinyl, trifluoromethylbenzophenonyl, or 10,10-dioxophenoxathiinyl;
$R_{12}$ is oxadiazolyl, or thiadiazolyl, and each of these heterocyclic rings is connected through a carbon atom and each may be unsubstituted or substituted by one or two $C_{1-2}$ alkyl groups unsubstituted or substituted by one to three fluorines;
$R_{13}$ is hydrogen or $R_7$; or when $R_{10}$ and $R_{13}$ are as $NR_{10}R_{13}$ they may together with the nitrogen form a 5 to 7 membered ring comprised of carbon or carbon and one or more additional heteroatoms selected from O, N, or S, wherein the additional nitrogen heteroatom may be unsubstituted or substituted by one or two $C_{1-2}$ alkyl groups unsubstituted or substituted by one to three fluorines;
$R_{14}$ is hydrogen, $C_{1-2}$ alkyl unsubstituted or substituted by one to three fluorines, $C(O)R_{13}$, $C(O)OR_{13}$, $C(O)NR_{10}R_{13}$, $OR_8$, or $S(O)_qR_7$;

provided that when Z is —NHC(O)R$_7$, NH[C(O)C(O)OR$_8$], NH[C(O)C(O)NR$_{10}$R$_{13}$], and W is alkynly or alkenyl of 2 carbons, then R$_3$ is not H or a C1-4 alkyl group unsubstitited or substituted by one to three fluorines; or the pharmaceutically acceptable salts thereof.

This invention also relates to the pharmaceutical compositions comprising a compound of Formula (I) and a pharmaceutically acceptable carrier or diluent.

The invention also relates to a method of mediation or inhibition of the enzymatic activity (or catalytic activity) of PDE IV in mammals, including humans, which comprises administering to a mammal in need thereof an effective amount of a compound of Formula (I) as shown above.

The invention further provides a method for the treatment of allergic and inflammatory disease which comprises administering to a mammal, including humans, in need thereof, an effective amount of a compound of Formula (I).

The invention also provides a method for the treatment of asthma which comprises administering to a mammal, including humans, in need thereof, an effective amount of a compound of Formula (I).

This invention also relates to a method of inhibiting TNF production in a mammal, including humans, which method comprises administering to a mammal in need of such treatment, an effective TNF inhibiting amount of a compound of Formula (I). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of Formula (I).

Compounds of Formula (I) are also useful in the treatment of additional viral infections, where such viruses are sensitive to upregulation by TNF or will elicit TNF production in vivo.

In addition, compounds of Formula (I) are also useful in treating yeast and fungal infections, where such yeast and fungi are sensitive to upregulation by TNF or will elicit TNF production in vivo.

DETAILED DESCRIPTION OF THE INVENTION

This invention also relates to a method of mediating or inhibiting the enzymatic activity (or catalytic activity) of PDE IV in a mammal in need thereof and to inhibiting the production of TNF in a mammal in need thereof, which comprises administering to said mammal an effective amount of a compound of Formula (I).

Phosphodiesterase IV inhibitors are useful in the treatment of a variety of allergic, autoimmune and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock, adult respiratory distress syndrome, multiple sclerosis and Alzheimer's disease. In addition, PDE IV inhibitors are useful in the treatment of diabetes insipidus and central nervous system disorders such as depression and multi-infarct dementia.

The viruses contemplated for treatment herein are those that produce TNF as a result of infection, or those which are sensitive to inhibition, such as by decreased replication, directly or indirectly, by the TNF inhibitors of Formula (I). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (I).

The compounds of this invention may also be used in association with the veterinary treatment of animals, other than in humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anemia virus, caprine arthritis virus, visna virus, maedi virus and other lentiviruses.

The compounds of this invention are also useful in treating yeast and fungal infections, where such yeast and fungi are sensitive to upregulation by TNF or will elicit TNF production in vivo. A preferred disease state for treatment is fungal meningitis. Additionally, the compounds of Formula (I) may be administered in conjunction with other drugs of choice for systemic yeast and fungal infections. Drugs of choice for fungal infections, include but are not limited to the class of compounds called the polymixins, such as Polymycin B, the class of compounds called the imidazoles, such as clotrimazole, econazole, miconazole, and ketoconazole; the class of compounds called the triazoles, such as fluconazole, and itranazole, and the class of compound called the Amphotericins, in particular Amphotericin B and liposomal Amphotericin B.

The compounds of Formula (I) may also be used for inhibiting and/or reducing the toxicity of an anti-fungal, anti-bacterial or anti-viral agent by administering an effective amount of a compound of Formula (I) to a mammal in need of such treatment. Preferably, a compound of Formula (I) is administered for inhibiting or reducing the toxicity of the Amphotericin class of compounds, in particular Amphotericin B.

The term "$C_{1-2}$ alkyl", "$C_{1-4}$ alkyl", "$C_{1-6}$ alkyl" or "alkyl" groups as used herein is meant to include both straight or branched chain radicals of 1 to 10, unless the chain length is limited thereto, including, but not limited to methyl, ethyl, n-propyl, isopropyl, n-butyl, sec-butyl, isobutyl, tert-butyl, and the like.

The term "cycloalkyl" or "cycloalkyl alkyl" means groups of 3–7 carbon atoms, such as cyclopropyl, cyclopropylmethyl, cyclopentyl, or cyclohexyl.

"Aryl", "aralkyl" or "aryloxyalkyl", unless specified otherwise, means an aromatic ring or ring system of 6–10 carbon atoms, such as phenyl, benzyl, phenethyl, or naphthyl. Preferably the aryl is monocyclic, i.e, phenyl. The alkyl chain is meant to include both straight or branched chain radicals of 1 to 4 carbon atoms. The term "oxy" is intended to have the usual chemical meaning, i.e., an oxygen atom.

"Halo" means all halogens, i.e., chloro, fluoro, bromo, or iodo.

"Inhibiting the production of IL-1" or "inhibiting the production of TNF" means:

(a) a decrease of excessive in vivo IL-1 or TNF levels, respectively, in a human to normal levels or below normal levels by inhibition of the in vivo release of IL-1 by all cells, including but not limited to monocytes or macrophages;

(b) a down regulation, at the translational or transcriptional level, of excessive in vivo IL-1 or TNF levels, respectively, in a human to normal levels or below normal levels; or (c) a down regulation, by inhibition of the direct synthesis of IL-1 or TNF levels as a postranslational event.

The phrase "TNF mediated disease or disease states" means any and all disease states in which TNF plays a role, either by production of TNF itself, or by TNF causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF. As TNF-β (also known as lymphotoxin) has close structural homoloy with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise. Preferably TNF-α is inhibited.

"Cytokine" means any secreted polypeptide that affects the functions of cells, and is a molecule which modulates interactions between cells in immune, inflammatory, or hematopoietic responses. A cytokine includes, but is not limited to, monokines and lymphokines regardless of which cells produce them.

The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. Preferrably, his cytokine is TNF-α.

All of the compounds of Formula (I) are useful in the method of inhibiting the production of TNF, preferably by macrophages, monocytes or macrophages and monocytes, in a mammal, including humans, in need thereof. All of the compounds of Formula (I) are useful in the method of inhibiting or mediating the enzymatic or catalytic activity of PDE IV and in treatment of disease states mediated thereby.

Preferred compounds are as follows:

When $R_1$ is an alkyl substituted by 1 or more halogens, the halogens are preferably fluorine and chlorine, more preferably a $C_{1-4}$ alkyl substituted by 1 or more fluorines. The preferred halo-substituted alkyl chain length is one or two carbons, and most preferred are the moieties —$CF_3$, —$CH_2F$, —$CHF_2$, —$CF_2CHF_2$, —$CH_2CF_3$, and —$CH_2CHF_2$. Preferred $R_1$ substitutents for the compounds of Formula (I) and (II) are $CH_2$-cyclopropyl, $CH_2$–$C_{5-6}$ cycloalkyl, $C_{4-6}$ cycloalkyl unsubstituted or substituted with OH, $C_{7-11}$ polycycloalkyl, (3- or 4-cyclopentenyl), phenyl, tetrahydrofuran-3-yl, benzyl or $C_{1-2}$ alkyl unsubstituted or substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$.

When the $R_1$ term is $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be —$CH_2CH(-CH_3)$—, for instance. The individual hydrogen atoms of the repeating methylene unit or the branching hydrocarbon can unsubstituted or be substituted by fluorine independent of each other to yield, for instance, the preferred $R_1$ substitutions, as noted above.

Preferred X groups are those wherein X is $YR_2$ and Y is oxygen. The preferred $X_2$ group for is that wherein $X_2$ is oxygen. The preferred $X_3$ group for Formula (I) and (II) is that wherein $X_3$ is hydrogen. Preferred $R_2$ groups, where applicable, is a $C_{1-2}$ alkyl unsubstituted or substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Preferred are those compounds of Formula (I) wherein $R_1$ is —$CH_2$-cyclopropyl, —$CH_2$–$C_{5-6}$ cycloalkyl, —$C_{4-6}$ cycloalkyl unsubstituted or substituted with OH, X is $YR_2$, and Z is tetrazol-5-yl, $C(O)R_{13}$, $C(O)OR_{13}$, $C(O)NR_{10}R_{13}$,) or (3- or 5-oxadiazolyl[1,2,4].

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. The parent compound, dissolved in a suitable solvent, is treated with an excess of an organic or inorganic acid, in the case of acid addition salts of a base, or an excess of organic or inorganic base where the molecule contains a COOH for example.

Pharmaceutical compositions of the present invention comprise a pharmaceutical carrier or diluent and some amount of a compound of the Formula (I). The compound may be present in an amount to effect a physiological response, or it may be present in a lesser amount such that the user will need to take two or more units of the composition to effect the treatment intended. These compositions may be made up as a solid, liquid or in a gaseous form. Or one of these three forms may be transformed to another at the time of being administered such as when a solid is delivered by aerosol means, or when a liquid is delivered as a spray or aerosol.

The nature of the composition and the pharmaceutical carrier or diluent will, of course, depend upon the intended route of administration, for example parenterally, topically, orally or by inhalation.

For topical administration the pharmaceutical composition will be in the form of a cream, ointment, liniment, lotion, pastes, aerosols, and drops suitable for administration to the skin, eye, ear, or nose.

For parenteral administration the pharmaceutical composition will be in the form of a sterile injectable liquid such as an ampule or an aqueous or non-aqueous liquid suspension.

For oral administration the pharmaceutical composition will be in the form of a tablet, capsule, powder, pellet, atroche, lozenge, syrup, liquid, or emulsion.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The pharmaceutical preparations thus described are made following the conventional techniques of the pharmaceutical chemist as appropriate to the desired end product.

In these compositions, the amount of carrier or diluent will vary but preferably will be the major proportion of a suspension or solution of the active ingredient. When the diluent is a solid it may be present in lesser, equal or greater amounts than the solid active ingredient.

Usually a compound of Formula I is administered to a subject in a composition comprising a nontoxic amount sufficient to produce an inhibition of the symptoms of a disease in which PDE IV enzymes are a factor. Topical formulations will contain between about 0.001 to 5.0% by weight of the active ingredient and will be applied as required as a preventative or curative agent to the affected area When employed as an oral, or other ingested or injected regimen, the dosage of the composition is selected from the range of from 10 mg to 1000 mg of active ingredient for each administration. For convenience, equal doses will be administered 1 to 5 times daily with the daily dosage regimen being selected from about 50 mg to about 5000 mg.

It will be recognized that some of the compounds of Formula (I) may exist in both racemic and optically active forms; some may also exist in distinct diastereomeric forms possessing distinct physical and biological properties. All of these compounds are considered to be within the scope of the present invention.

The following examples are given to further illustrate the described invention. These examples are intented solely for illustrating the invention and should not be read to limit the invention in any manner. Reference is made to the claims for what is reserved to the inventors hereunder.

No unacceptable toxicological effects are expected when these compounds are administered in accordance with the present invention.

METHODS OF PREPARATION

Compounds of Formula (I) may be prepared by the processes disclosed herein

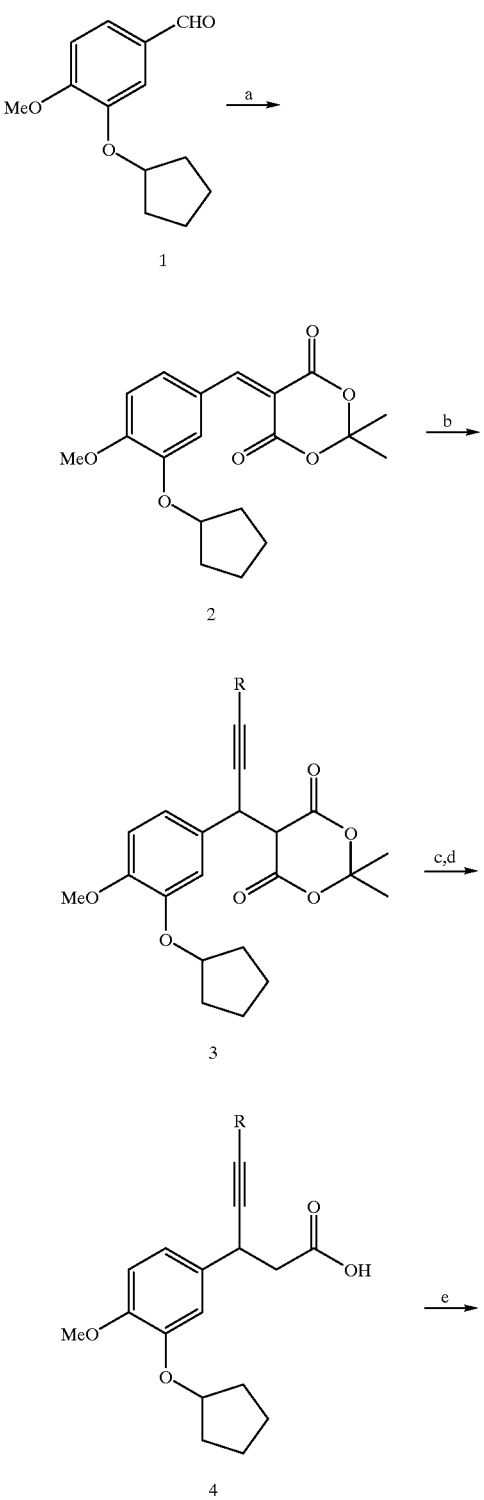

11

-continued

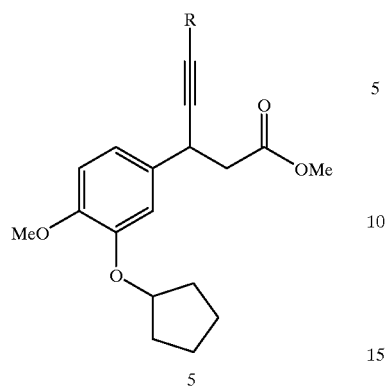
5

12

-continued

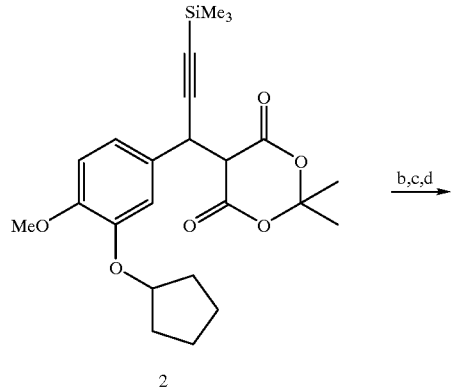
2 b,c,d →

(a) Meldrum's acid, piperidine, HOAc, benzene; (b) RC≡CH, BuLi, THF: (c) dioxane, aq. HCl: (d) dimethylacetamide, reflux; e) CH$_2$N$_2$. Aldehyde 1-Scheme-1 may be condensed with a malonic ester derivative, such as Meldrum's acid, under acid base catalysis such as piperidine and acetic acid, or p-toluene sulfonic acid and pyridine, with refluxing in a suitable solvent such as benzene or toluene, preferably removing the water formed by distillation. The resulting benzylidene malonate, 2-Scheme-1 can be alkylated with ethynyl lithium compounds, in non-protic solvents such as tetrahydrofuran or diethyl ether, at temperatures from −78° C. to 0° C., preferably −78° C., to give 3-Scheme-1. The cyclic ester of 3-Scheme-1 may be hydrolyzed by heating with an acid such as aqueous hydrochloric acid in a non-alcoholic solvent such as tetrahydrofuran or dioxane. The intermediate malonic acid from this hydrolysis can be decarboxylated by heating briefly in a solvent such as dimethylacetamide or dimethylformamide at a temperature from 65° C. to 140° C., preferably 135° C. The substituted phenylpropionic acid, 4Scheme-1 may be esterified by a number of methods, such as diazomethane in diethyl ether, methanol and HCl(g), or methanol and trimethylsilyl chloride, giving the methyl propionate, 5-Scheme-1.

Scheme 2

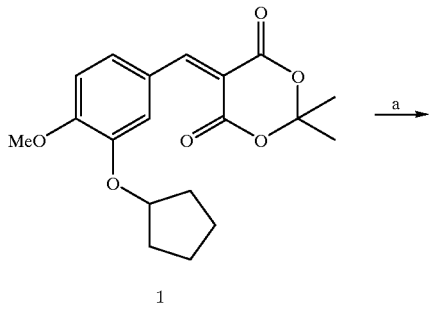
1 a →

3 e →

4 f →

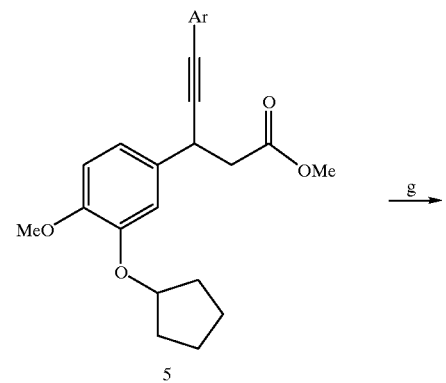
5 g →

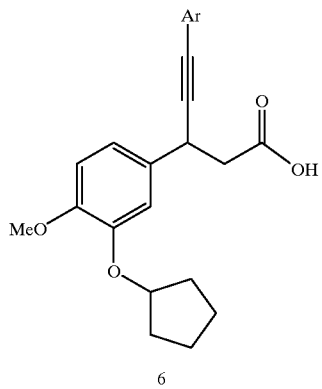

a) Me₃SiC≡CH, BULi; (b) aq. HCl, dioxane; (c) dimethylacetamide, reflux; (d) NaOH; e) CH₂N₂: f) ArI, Pd. CuI, Et₃N; g) NaOH.

The benzylidene derivative of Meldrum's acid, 1-Scheme-2, can be alkylated with a lithiated, protected acetylene, in this case the species formed from the reaction of n-butyl lithium with trimethylsilyl acetylene, in a solvent such as tetrahydrofuran or diethyl ether, in this case tetrahydrofuran, at a temperature from −78° C. to 0° C., in this case −78° C., giving the alkylated species 2-Scheme-2. The cyclic diester of 2-Scheme-2 can be cleaved by refluxing in a mixture of tetrahydrofuran or dioxane, in this case dioxane, and aqueous HCl. The intermediate malonic acid derivative could be decarboxylated thermally in dimethylacetamide or dimethylformamide, in this case dimethylacetamide, at a temperature from 65° C. to 140° C., preferably 135° C. The trimethylsilyl protecting group can be removed with base, such as NaOH, K₂CO₃, or NaOMe, preferably aqueous NaOH, to give 3-Scheme-2. The substituted phenylpropionic acid 3-Scheme-2 may be esterified using diazomethane, methanolic HCl, or methanol and trimethylsilyl chloride, preferably with diazomethane, to give the acetylenic ester 4 Scheme-2. Arylation of the acetylene of 4-Scheme-2 may be done using an appropriate aromatic bromide or iodide, preferably iodide, under catalysis by a zero valent palladium species, in this case tetrakis (triphenylphosphine)palladium(0), and a monovalent copper species, in this case copper(1) iodide, to give the substituted acetylene, 5-Scheme-2. The methyl ester may be hydrolyzed under basic conditions, in this case a mixture of aqueous NaOH and MeOH, to give the carboxylic acid 6-Scheme-2.

Scheme 3

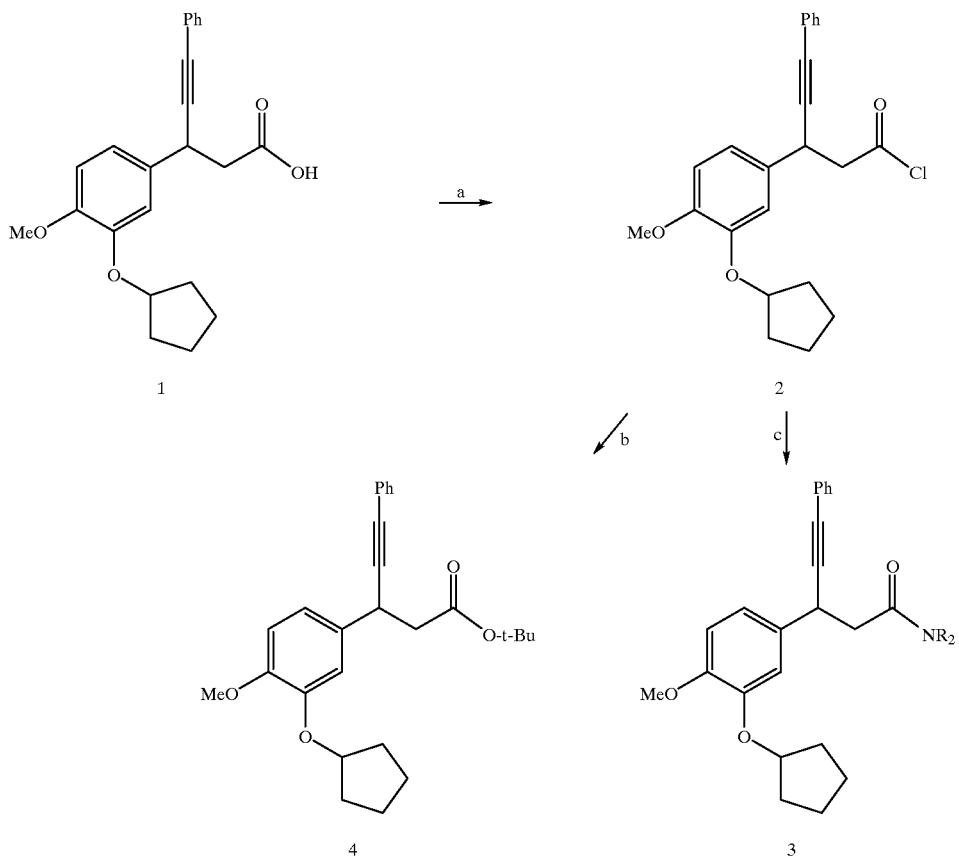

(a) (COCl)₂, DMF, benzene; (b) t-BuOH, PhNMe₂, Et₂O; (c) HNR₂, Me₂CO, H₂O.

Propionic acid 1-Scheme-3 can be treated with a chlorinating agent such as oxalyl chloride, thionyl chloride or phosphorus pentachloride, in this case oxalyl chloride, under catalysis by dimethylformamide, in a solvent such as benzene, toluene, methylene chloride or dichlorethane, in this case benzene, at a temperature from 0° C. to 78° C., in this case 23° C., to give the acid chloride, 2-Scheme-3. The acid chloride may be reacted with an alcohol, in this case t-butanol in the prsence of a base, in this case dimethylaniline, to give an ester, in this case the t-butyl ester, 4-Scheme-3. Alternatively, the acid chloride 2-Scheme-3 can be reacted with an excess of a primary or secondary amine, in a mixture of acetone and water, at a temperature of −20° C. to 0° C., preferably −20° C, to give the amide, 3-Scheme-3.

Scheme 4

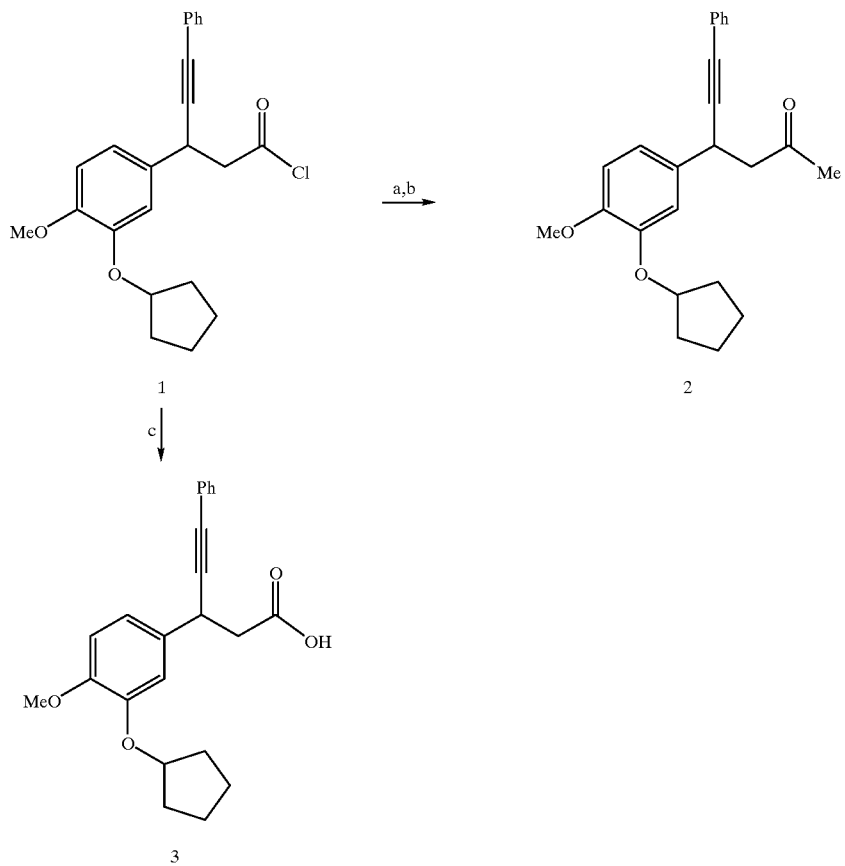

(a) Meldrum's acid, pyridine, $CH_2Cl_2$, 0° C.; (b) HOAc, $H_2O$, reflux; (c) $NaBH_4$, glyme, 0° C.

The acid chloride, 1-Scheme4, prepared as in Scheme 3, could be used to acylate Meldrum's acid, in a solvent such as methylene chloride, chloroform, ether, or benzene, in this case methylene chloride, in the presence of a base such as pyridine, triethylamine or dimethylaniline, in this case pyridine. The intermediate acylated Meldrum's acid was immediately hydroyzed under mild acidic catalysis, in this case acetic acid, to give the ketone, 2-Scheme4. Also, the acid chloride 1-Scheme-4 can be reduced with a hydride reducing agent such as lithium aluminum hydride or sodium borohydride, in this case sodium borohydride, in a solvent such as diethyl ether, tetrahydrofuran, or dimethoxyethane, in this case dimethoxyethane, to five the alcohol 3-Scheme4.

Scheme 5

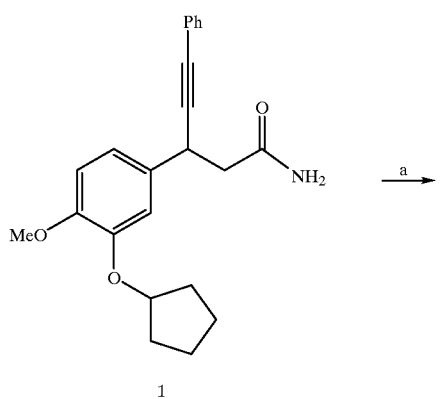
1

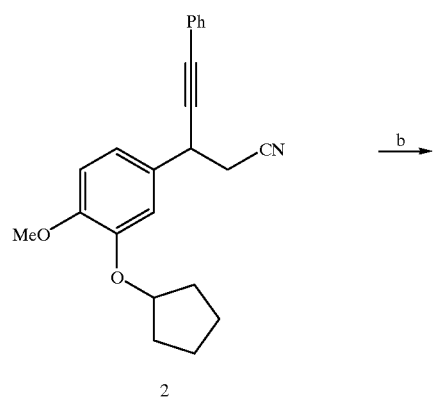
2

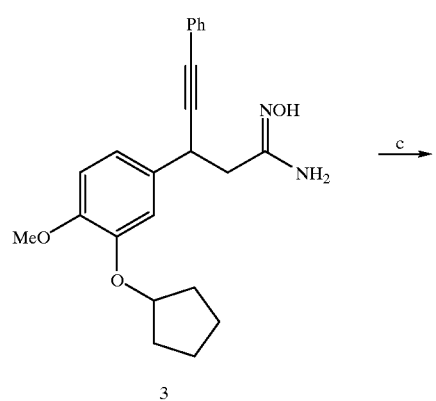
3

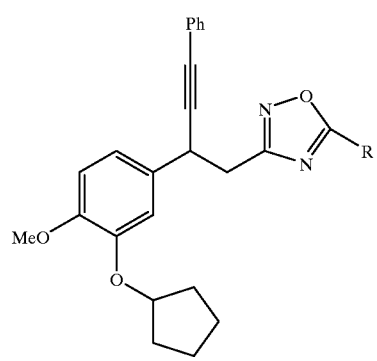
4

(a) TFA anhydride, pyridine, CH₂Cl₂; (b) NH₂OH·HCl, K₂CO₃, EtOH, H₂O; (c) CH(OEt)₃ or (RCO)₂O, reflux.

The primary amide 1-Scheme-5, prepared as shown in Scheme 3, can be reacted with a dehydrating agent such as trifluoroacetic anhydride, thionyl chloride, or oxalyl chloride, in this case oxalyl chloride, in the presence of a base, such as triethylamine, pyridine or dimethylaniline, in this case pyridine, at a temperature from −20° C. to 23° C., in this case 0° C., to give the nitrile, 2-Scheme-5. The nitrile can be reacted with a solution of excess hydroxylamine in aqueous ethanol at 55° C. to give the hydroxyamidine, 3-Scheme-5. Reaction of the hydroxyamidine with an acylating agent, for example trifluoroacetic anhydride, acetic anhydride, acetyl chloride or triethylorthoformate can give an O-acyl hydroxyamidine, which can then undergo ring closure thermally or in the presence of excess acylating agent, to give the oxadiazole 4-Scheme-5.

Scheme 6

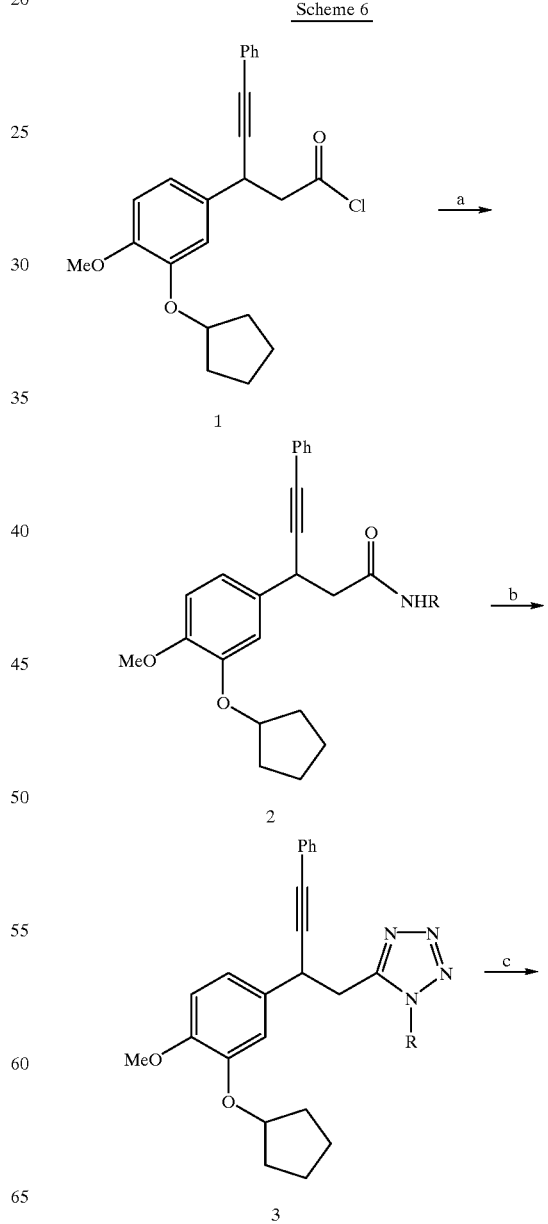

19

-continued

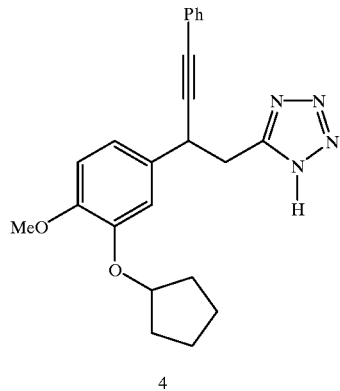

4

(a) RNH₂, Me₂CO, H₂O; (b) Ph₃P, DEAD, TMSN₃; (c) NaOH, H₂O, MeOH.

Acid chloride 1-Scheme-6, prepared as in Scheme 3, can be reacted with an excess of a primary amine, in this case either methylamine or 2-cyanoethylamine, in a mixture of acetone and water, at −20° C. to give the secondary amide, 2-Scheme-6. This amide can be reacted with a phosphine such as triphenyl phosphine or tributylphosphine, in this case triphenylphosphine, a proton acceptor such as diethylazodicarboxylate or di-isopropylazodicarboxylate, in this case diethylazodicarboxylate, and a source of azide such as azidotrimethylsilane, in a solvent such as THF, dioxane, benzene, toluene or methylene chloride, in this case tetrahydrofuran, to give the substituted tetrazole 3-Scheme-6. When the substitution on 1 position of the tetrazole is the 2-cyanoethyl group, this group can be removed by treatment of 3-Scheme-6 with base, in this case aqueous NaOH in MeOH, to give the 1H-tetrazole 4Scheme-6.

It will be recognized that certain compounds of Formula (I) may exist in distinct diastereomeric forms possessing distinct physical and biological properties; such isomers may be separated by standard chromatographic methods.

The following examples are given to further illustrate the described invention. These examples are intented solely for illustrating the invention and should not be read to limit the invention in any manner. Reference is made to the claims for what is reserved to the inventors hereunder.

SPECIFIC EXAMPLES

Example 1

Preparation of (+/−)-3-(3-cyclopentyloxy-4-methoxyphenyl)-3-phenylethynylpropionic acid 1(a) 2,2-Dimethyl-5-(3-cyclopentyloxy-4-methoxybenzylidenyl)-1,3-dioxane-4,6-dione A mixture of 3-cyclopentyloxy-4-methoxybenzaldehyde (12.8 g, 0.058 mol), 2,2-dimethyl-1,3-dioxane-4,6-dione (8.3 g, 0.058 mol), piperidine (1 mL) and HOAc (0.5 mL) in benzene (150 mL) was refluxed for 2 h, using a Dean Stark trap to remove the water that was formed. Hexane (75 mL) was added, the mixture was cooled, and the crystalline product filtered and dried (18.7 g, 93%). mp 116–119° C.

1(b) (+/−)-2,2-dimethyl-5-([1-(3-cyclopentyloxy-4-methoxyphenyl)-3-phenyl]prop2-yne)-1,3-dioxane-4,6-dione A solution of phenylacetylene (2.66 g, 0.026 mol) in THF (50 mL) at 0° C. was treated slowly with a solution of n-BuLi (0.026 mol) in hexane (16.4 mL). After the addition, the reaction was stirred for 15 min at 23° C., and then cooled

20 to −78° C. A solution of the compound of Example 1 (a) (8.0 g, 0.022 mol) in THF (125 mL) was added over 5 min, and stirring was continued at −78° C. for 30 min. The reaction was quenched with water (500 mL) and 3N HCl (20 mL), and extracted with ether. The extracts were washed with water, dried (CaSO₄), and the solvent evaporated. The residue was recrystallized from a mixture of CH₂Cl₂ and cyclohexane, and gave the titled compound (8.31 g, 84%). mp 108–114° C.

1(c) (+/−)-3-(3-Cyclopentyloxy-4-methoxyphenyl)-3-phenylethynylpropionic acid

A solution of the compound of Example 1 (b) (4.2 g, 9.4 mmol) in dioxane (70 mL), water ( 3 mL) and 3N HCl (5 mL) was heated at 100° C. for 90 min. The reaction was cooled, diluted with water (200 mL), and extracted with ether. The extracts were washed with water, dried (CaSO₄), and the solvent evaporated. The residue was dissolved in dimethylacetamide (10 mL), and the solution was heated at 135° C. for 30 min. The reaction was cooled, diluted with water (200 mL) and extracted with ether. The extracts were washed well with water, dried (CaSO₄), and the solvent evaporated. The residue was recrystallized from a mixture of CH₂Cl₂ and hexane, and gave the titled compound (2.8 g, 82%). mp 86–88° C.

Example 2

Preparation of (+/−)-methyl-(3-cyclopentyloxy-4-methoxyphenyl)-3-phenylethynylpropionate A solution of the compound from Example 1(c) (210 mg, 0.58 mmol) in ether (20 mL) was treated with an excess of a solution of diazomethane in ether for 5 min at 23° C. The solvent was evaporated, and the residue crystallized from hexane, and gave the titled compound (160 mg, 73%). mp 71–75° C.

Example 3

Preparation of (+/−)-methyl-3-(3-cyclopentyloxy-4-methoxyphenyl)-7-hydroxyhept-4-ynoate 3(a) (+/−)-2,2-Dimethyl-5-(1-(3-cyclopentyloxy-4-methoxyphenyl)-5-(tetrahydropyran-2-yloxy)-pent-2-yn)-1,3-dioxane-4,6-dione Following the procedure of Example 1(b), except substituting 4-(tetrahydropyran-2-yloxy)butyne for phenylacetylene, the titled compound was obtained (51%). ¹H NMR (400 MHz, CDCl₃) δ 7.08 (s, 1 H), 7.00 (d, 1 H), 6.80 (d, 1 H), 4.84 (m, 1 H), 4.80 (m, 1 H), 4.66 (m, 1 H), 3.76–3.90 (m, 3 H), 3.84 (s, 3 H), 3.54–3.60 (m, 1 H), 3.46–3.52 (m, 1 H), 2.56 (m, 2 H), 1.48–1.98 (m, 14 H), 1.70 (s, 3 H), 1.58 (s, 3 H).

3(b) (+/−)-3-(3-cyclopentyloxy-4methoxyphenyl)-7-hydroxyhept-4-ynoic acid

Following the procedure of Example 1(c), except substituting (+/−)-2,2-dimethyl-5-(1-(3-cyclopentyloxy-4-methoxyphenyl)-5-(tetrahydropyran-2-yloxy)-pent-2-yn)-1,3-dioxane-4,6-dione for (+/−)-2,2-dimethyl-5-([1-(3-cyclopentyloxy-4-methoxyphenyl)-3-phenyl]prop-2-yne)-1,3-dioxane-4,6-dione gave the titled compound (72%).

3(c) (+/−)-Methyl-3-(3-cyclopentyloxy-4-methoxyphenyl)-7-hydroxyhept-4-ynoate

Following the procedure of Example 2, except substituting (+1-)-3-(3-cyclopentyloxy-4-methoxyphenyl)-7-hydroxyhept-4-ynoic acid for (+/−)-3-(3-cyclopentyloxy-4-methoxyphenyl)-3-phenylethynylpropionic acid gave the titled compound (50%). ¹H NMR (400 MHz, CDCl₃) δ 6.81–6.89 (m, 3 H), 4.77 (m, 1 H), 4.05 (m, 1 H), 3.82 (s, 3 H), 3.68 (s, 3 H), 3.68–3.72 (m, 2 H), 2.71 (m, 2 H), 2.48 (m, 2 H), 2.12 (s, 1 H), 1.72–1.92 (m, 6 H), 1.61 (m, 2 H).

Example 4

Preparation of (+/−)-methyl-3-(3-cyclopentyloxy-4-methoxyphenyl)-8-hydroxyoct-4-ynoate 4(a) 5-(Tetrahydropyran-2-yloxy) pentyne A mixture of 5-hydroxypentyne (5.0 g, 0.06 mol) and freshly distilled dihydropyran (10 mL) was treated with a trace of p-toluenesulfonic acid hydrate. The exothermic reaction was stirred for 5 min, and the excess dihydropyran was removed under reduced pressure. The residue was purified by flash chromatography (alumna, neutral, activity 1, 25% ether/hexane) and gave the title compound (6.4 g, 63%). $^1$H NMR (400 MHz, CDCl$_3$) δ 4.60 (t, 1 H), 3.86 (m, 2 H), 3.50 (m, 2 H), 2.32 (m, 2 H), 1.96 (t, 1 H), 1.82 (m, 3 H), 1.72 (m, 1 H), 1.48–1.65 (m, 4 H).

4(b) (+/−)-2,2-Dimethyl-5-(1-(3-cyclopentyloxy-4-methoxyphenyl)-6-(tetrahydropyran-2-yloxy)-hex-2-yn)-1,3-dioxane-4,6-dione Following the procedure of Example 1(b), except substituting 5-(tetrahydropyran-2-yloxy)pentyne for phenylacetylene, the titled compound was obtained (81%). $^1$H NMR (400 MHz, CDCl$_3$) δ 7.12 (s, 1 H), 7.00 (d, 1 H), 6.80 (d, 1 H), 4.84 (d, 1 H), 4.80 (m, 1 H), 4.61 (d, IH), 3.88 (m, 3 H), 3.82 (s, 3 H), 3.52 (m, 2 H), 2.38 (m, 2 H), 1.50–2.00 (m, 16 H), 1.74 (s, 3 H), 1.62 (s, 3 H).

4(c) (+/−)-3-(3-Cyclopentyloxy-4-methoxyphenyl)-8-hydroxyoct-4ynoic acid

Following the procedure of Example 1(c), except substituting (+/−)-2,2-dimethyl-5-(1-(3-cyclopentyloxy-4-methoxyphenyl)-6-(tetrahydropyran-2-yloxy)-hex-2-yn)-1,3-dioxane-4,6-dione for (+/−)-2,2-dimethyl-5-([1-(3-cyclopentyloxy-4-methoxyphenyl)-3-phenyl]prop2-yne)-1,3-dioxane-4,6-dione gave the titled compound, purified by flash chromatography (silica gel, 2%MeOH/0.5%HOAc/CH$_2$Cl$_2$) (29%). $^1$H NMR (400 MHz, CDCl$_3$) δ 6.90 (m, 2 H), 6.80 (d, 1 H), 6.52 (br s, 2 H), 4.78 (m, 1 H), 4.06 (m, 1 H), 3.82 (s, 3 H), 3.79 (m, 2 H), 2.72 (m, 2 H), 2.34 (m, 2 H), 1.54–1.96 (m 10 H).

4(d) (+/−)-Methyl-3-(3-cyclopentyloxy-4-methoxyphenyl)-8-hydroxyoct-4-ynoate

Following the procedure of Example 2, substituting (+/−)-3-(3-cyclopentyloxy-4-methoxyphenyl)-8-hydroxyoct-4-ynoic acid for (+/−)-3-(3-cyclopentyloxy-4-methoxyphenyl)-3-phenylethynylpropionic acid, the titled compound was prepared and purified by flash chromatography (alumina, neutral, activity 1, 2%MeOH/ether) (89%). $^1$H NMR (400 MHz, CDCl$_3$) δ 6.87 (m, 2 H), 6.78 (d, 1 H), 4.77 (m, 1 H), 4.05 (m, 1 H), 3.81 (s, 3 H), 3.71 (t, 2 H), 3.66 (s, 3 H), 2.68 (m, 2 H), 2.32 (m, 2 H), 1.82–1.98 (m, 6 H), 1.74 (t, 2 H), 1.61 (m, 2 H).

Example 5

Preparation of (+/−) methyl-3-(3-cyclopentyloxy-4-methoxyphenyl)non-4-ynoate

5(a) (+/−)-2,2-Dimethyl-5-(1-(3-cyclopentyloxy-4-methoxyphenyl)-hept-2-yn)-1,3-dioxane4,6-dione Following the procedure in Example 1(b), except substituting 1-hexyne for phenylacetylene, the titled compound was prepared and purified by crystallization from cyclohexane (75%). $^1$H NMR (400 MHz, CDCl$_3$) δ 7.13 (d, 1 H), 6.98 (dd, 1 H), 6.90 (d, 1 H), 4.82 (d, 1 H), 4.79 (m, 1 H), 3.82 (s, 4 H), 2.28 (m, 2 H), 1.72 (s, 3 H), 1.56 (s, 3 H), 1.40–2.00 (m, 12 H), 0.92 (t, 3 H).

5(b) (+/−)-3-(3-Cyclopentyloxy-4-methoxyphenyl)non-4-ynoic acid

Following the procedure in Example 1(c), except substituting (+/−)-2,2-dimethyl-5-(1-(3-cyclopentyloxy-4-methoxyphenyl)-hept-2-yn)-1,3-dioxane-4,6-dione for (+/−)-2,2-dimethyl-5-([1-(3-cyclopentyloxy-4-methoxyphenyl)-3-phenyl]prop-2-yne)-1,3-dioxane-4,6-dione, the titled compound was prepared and purified by flash chromatography (Florisil, 5% MeOH/0.1% HOAc/ether) (47%). $^1$H NMR (400 MHz, CDCl$_3$) δ 6.96 (d, 1 H), 6.90 (d of d, 1 H), 6.82 (d, 1 H), 4.76 (m, 1 H), 4.08 (m, 1 H), 3.81 (s, 3 H), 2.80 (d of d, 1 H), 2.70 (d of d, 1 H), 2.25 (m, 2 H), 1.70–1.95 (m, 6 H), 1.62 (m, 2 H), 1.38–1.52 (m, 4 H), 0.94 (t, 3 H).

5(c) (+/−)-Methyl-3-(3-cyclopentyloxy-4-methoxyphenyl)non-4-ynoate

The compound from Example 5(c) (120 mg, 0.35 mmol) in MeOH (5 mL) was treated with a solution (1M) of HCl in Et$_2$O (0.2 mL) and stirred for 18 h at 23° C. The solvents were evaporated, and the residue was purified by flash chromatography (alumina, neutral, activity 1, CH$_2$Cl$_2$) and gave the titled compound (72%). $^1$H NMR (400 MHz, CDCl$_3$) δ 6.92 (d, 1 H), 6.86 (d of d, 1 H), 6.79 (d, 1 H), 4.76 (m, 1 H), 4.06 (m, 1 H), 3.81 (s, 3 H), 3.66 (s, 3 H), 2.73 (dd, 1 H), 2.65 (dd, 1 H), 2.21 (m, 2 H), 1.80–2.00 (m, 6 H), 1.61 (m, 2 H), 1.36–1.52 (m, 4 H), 0.91 (t, 3 H).

Example 6

Preparation of (+/−)-3-(3-cyclopentyloxy-4-methoxyphenyl)-3-ethynylpropionic acid 6(a) (+/−)-2,2-Dimethyl-5-([1-(3-cyclopentyloxy-4-methoxyphenyl)-3-trimethylsilyl]prop-2-yne)-1,3-dioxane-4,6-dione Following the procedure of Example 1(b), except substituting trimethylsilylacetylene for phenylacetylene, the titled compound was prepared (63%). mp 105–107° C.

6(b) (+/−)-3-(3-Cyclopentyloxy-4-methoxyphenyl)-3-trimethylsilylethynylpropionic acid Following the procedure of Example 1(c), except substituting (+/−)-2,2-dimethyl-5-([1-(3-cyclopentyloxy-4-methoxyphenyl)-3-trimethylsilyl]prop-2-yne)-1,3-dioxane-4,6-dione for (+/−)-2,2-dimethyl-5-([1-(3-cyclopentyloxy-4-methoxyphenyl)-3-phenyl]prop-2-yne)-1,3-dioxane-4,6-dione the titled compound was prepared (78%). $^1$H NMR (400 MHz, CDCl$_3$) δ 6.98 (d, 1 H), 6.88 (d of d, 1 H), 6.80 (d, 1 H), 4.80 (m, 1 H), 4.12 (t, 1 H), 3.82 (s, 3 H), 2.86 (d of d, 1 H), 2.74 (d of d, 1 H), 1.78–2.00 (m, 6 H), 1.62 (m, 2 H).

6(c) (+/−)-3-(3-Cyclopentyloxy-4-methoxyphenyl)-3-ethynylpropionic acid

The compound from Example 6(b) (60 mg, 0.18 mmol) was dissolved in a mixture of MeOH (2 mL) and H$_2$O (1 mL) and treated with NaOH (2.5N, 0.5 mL). The reaction was heated to 50° for 20 min, the diluted with H$_2$O (20 mL) and filtered. The filtrate was acidified, and extracted with ether. The extracts were washed with H$_2$O, dried (CaSO$_4$), and the solvent evaporated. The residue was crystallized from cyclohexane, and gave the titled compound (45 mg, 88%). mp 128–131° C.

Example 7

Preparation of (+/−) methyl-3-(3-cyclopentyloxy-4-methoxyphenyl)-3-ethynylpropionate Following the procedure of Example 2, except substituting (+/−)-3-(3-cyclopentyloxy-4-methoxyphenyl)-3- ethynylpropionic acid for (+/−)-3-(3-cyclopentyloxy-4-methoxyphenyl)-3-phenylethynylpropionic acid the titled compound was prepared, and purified by crystallization from hexane (78%). mp 41–42° C.

Example 8

Preparation of (+/−)-methyl-3-(3-cyclopentyloxy-4-methoxyphenyl)-3-[3-(5-methyl-[1,3,4]thiadiazol-2-yl)phenylethynyl]propionate 8(a) Methyl 3-iodobenzoate 3-Iodobenzoic acid (10.0 g, 40.3 mmol) was placed in dry methanol (50 mL) under an argon atmosphere and was treated with chlorotrimethylsilane (15.4 mL, 0.12 mol). After heating at 65° C. for 4 h, the mixture was cooled to room temperature and was concentrated in vacuo. The residue was partitioned between ethyl acetate (100 mL) and water, the organic phase was washed twice with water, was dried ($Na_2SO_4$) and was evaporated to provide the titled compound as a white solid (10.6 g, 100%).

8(b) 3-Iodobenzoyl hydrazine

A mixture of the compound from Example 8(a) (13.0 g, 49.6 mmol) and hydrazine monohydrate (26.0 mL, 0.55 mol) in methanol (200 mL) was refluxed under an argon atmosphere for 4 h. The mixture was cooled to room temperature, was concentrated in vacuo, and water was added. The resulting white solid precipitate was collected by filtration to provide the titled compound (11.84 g, 91%). p. 136–137° C.

8(c) 3-Iodobenzoyl-N'-acetyl hydrazine

A stirred solution of the compound from Example 8(b) (11.8 g, 45.2 mmol) in absolute ethanol (200 mL) was treated with triethylamine (9.5 mL, 67.8 mmol) followed by acetic anhydride (6.4 mL, 67.8 mmol) and the resulting solution was refluxed for 2.5 h. The mixture was cooled to room temperature, was concentrated in vacuo, and water was added. The resulting white solid precipitate was collected by filtration to provide the titled compound (13.7 g, 100%). mp 156–158° C.

8(d) 1-Iodo-3-(5-methyl-[1,3,4]thiadiazol-2-yl)benzene

A stirred mixture of the compound from Example 8(c) (7.0 g, 23.0 mmol), toluene (300 mL) and Lawessons's reagent (12.1 g, 30 mmol) was refluxed for 1.5 h under an argon atmosphere. The cooled mixture was diluted with chloroform (10 mL) and was basified with a 5% sodium carbonate solution. The organic phase was washed with water, was dried ($Na_2SO_4$) and was evaporated The residue was purified by flash chromatography, eluting with 99:1 ethyl acetate/dichloromethane to provide the titled compound as a white solid (2.48 g, 36%). mp 87–89° C.

8(e) (+/−)-Methyl-3-(3-cyclopentyloxy-4-methoxyphenyl)-3-[3-(5-methyl-[1,3,4]thiadiazol-2-yl)phenylethynyl] propionate To a solution of the compound from Example 7 (0.15 g, 0.5 mmol) and the compound from Example 8(d) (0.15 g, 0.50 mmol) in triethylamine (5 mL) under an argon atmosphere was added trace tetrakis(triphenylphosphine) palldium(0) and trace copper(I) iodide. The mixture was heated to 80° C. for 0.20 h, was cooled to room temperature and was concentrated in vacuo. Purification by flash chromatography (silica gel, 50%EtOAc/hexane) provided the titled compound as a yellow oil (0.21 g, 89%). Anal. ($C_{27}H_{28}N_2SO_4\cdot 0.5\ H_2O$) calcd: C, 66.76; H, 6.01; N, 5.77. found: 66.84; H, 5.80; N, 5.66.

Example 9

Preparation of (+/−)-3-(3-cyclopentyloxy-4-methoxyphenyl)-3[3-(5-methyl-[1,3,4]thiadiazol-2-yl) phenylethynyl]propionic acid To a solution of the compound from Example 8(e) (0.19 g, 0.40 mmol) in 5:5:2 THF/methanol/water (5 mL) was added solid NaOH (0.05 g, 1.2 mmol). After 24 h, the mixture was acidified (3N HCl), was concentrated in vacuo, and was partitioned between water and dichloromethane. The organic phase was dried ($MgSO_4$), was filtered and was evaporated. Purification by flash chromatography (silica gel, 10% MeOH/$CHCl_3$) provided the titled compound as a yellow solid (0.07 g, 38%). mp. 51–55° C.

Example 10

Preparation of (+/−)-methyl-3-(3-cyclopentyloxy-4-methoxyphenyl)-3-[3-(5-methyl-[1,3,4]oxadiazol-2-yl)phenylethynyl]propionate 10(a) 1-Iodo-3-(5-methyl-[1,3,4]oxadizol-2-yl)benzene A stirred mixture of the compound from Example 8(c) (7.1 g, 23.4 mmol), phosphorus oxychloride (21.0 mL, 0.23 mol), and toluene (200 mL) was refluxed for 2 h under an argon atmosphere. The cooled mixture was partitioned between chloroform and water, the organic phase was washed with water, was dried ($MgSO_4$) and was evaporated. Purification by flash chromatography(silica gel, 35%EtOAc/hexane) provided the titled compound as a white solid (3.54 g, 53%). mp 104–105° C.

10(b) (+/−)-Methyl-3-(3-cyclopentyloxy-4-methoxyphenyl)-3-[3-(5-methyl-[1,3,4]oxadiazol-2-yl) phenylethynyl]propionate To a solution of the compound from Example 7 (0.15 g, 0.5 mmol) and 1-iodo-3-(5-methyl-[1,3,4]oxadiazol-2-yl) benzene (0.14 g, 0.5 mmol) in triethylamine (5 mL) under an argon atmosphere was added trace tetrakis (triphenylphosphine)palladium(0) and trace copper(I) iodide. The mixture was heated at 80° C. for 0.2 h, was cooled to room temperature and was concentrated in vacuo. Purification by flash chromatography (silica gel, 50% EtOAc/hexane) provided the titled compound as a yellow oil (0.19 g, 80%). Anal. ($C_{27}H_{28}N_2O_5\cdot 0.375\ H_2O$) calcd: C, 69.40; H, 6.20; N, 6.00. found: C, 69.23; H, 6.13;N,5.69.

Example 11

Preparation of (+/−)-3-(3-cyclopentyloxy-4-methoxyphenyl)-3-[3-(5-methyl-[1,3,4]oxadiazol-2-yl)phenylethynyl]propionic acid To a solution of the compound from Example 10(b) (0.16 g, 0.35 mmol) in 5:5:2 THF/methanol/water (5 mL) was added solid NaOH (0.04 g, 1.05 mmol). After 24 h, the mixture was acidified (3N HCl), was concentrated in vacuo and was partitioned between water and dichloromethane. The organic phase was dried ($MgSO_4$), was filtered and was evaporated. Purification by flash chromatography (silica gel, 5% MeOH/$CHCl_3$) provided the titled compound as a yellow solid (0.05 g, 32%). m.p. 110–114° C.

Example 12

Preparation of (+/−)-methyl-3-(3-cyclopentyloxy-4-methoxyphenyl)-3-[3-(5-methyl-[1,2,4]oxadiazol-3-yl)phenylethynyl]propionate Following the procedure of Example 8(e), except substituting 1-iodo-3-(5-methyl-[1,2,4]oxadiazol-3-yl)benzene for 1-iodo-3-(5-methyl-[1,3,4]thiadiazol-2-yl)benzene the titled compound was prepared (69%). mp 66–68° C.

Example 13

Preparation of (+/−)-methyl 3-(3-cyclopentyloxy-4-methoxyphenyl)-3-(imidazol-2-ylethynyl) propionate 13(a) Methyl 3-(N-tert-butoxycarbonylimidazol-2-ylethynyl)-3-(3-cyclopentyloxy-4-methoxyphenyl) propionate To a suspension of the compound from Example 7 (0.50 g, 1.65 mmol) and N-tert-butoxycarbonyl-2-iodopyrimidine (0.49 g, 1.65 mmol) in triethylamine (5 mL) under an argon atmosphere were added tetrakis(triphenylphosphine) palladium(0) (0.079 g, 4%) and copper(I) iodide (0.018 g, 6%), and the mixture was heated at 85–90° C. for 0.5h. Water was added and the mixture was extracted three times with dichloromethane, was dried (magnesium sulfate) and was evaporated. Purification by flash chromatography (silica gel, 35%EtOAc/hexane) provided the titled compound as a yellow oil (0.34 g, 45%). $^1$H-NMR (CDCl$_3$, 400 MHz) δ 7.36 (d, J=1.8 Hz, 1 H), 6.97 (m, 3 H), 6.81 (d, J=8.0 Hz, 1 H), 4.82 (m, 1 H), 4.35 (t, J=7.5 Hz, 1 H), 3.82 (s, 3 H), 3.67 (s, 3 H), 2.91 (m, 2 H), 1.8–2.0 (m, 6 H), 1.6 (m, 2 H), 1.57 (s, 9 H).

13(b) (+/−)-Methyl 3-(3-cyclopentyloxy-4-methoxyphenyl)-3-(imidazol-2-ylethynyl) propionate A solution of the compound from Example 13(a) (0.34 g, 0.73 mmol) in ethyl acetate (10 mL) to which had been added 50 drops of hydrogen chloride-saturated ethyl acetate was stirred at room temperature under an argon atmosphere for 24 h. The solvent was evaporated and crude product was purified by two flash chromatographies(silica gel, 3% MeOH/CH$_2$Cl$_2$), (silica gel, 75% ether/hexane) provided the titled compound (0.033 g, 12%) as a white solid. mp 120–121° C.

Example 14

Preparation of (+/−)-methyl 3-(2-acetamidopyrimidin-5-ylethynyl)-3-(3-cyclopentyloxy-4-methoxyphenyl) propionate To a suspension of the compound from Example 7 (0.50 g, 1.65 mmol) and 2-acetamido-5-bromopyrimidine (0.38 g, 1.65 mmol) in triethylamine (5 mL) under an argon atmosphere were added tetrakis(triphenylphosphine)palladium (0) (0.080 g, 4%) and copper(I) iodide (0.020 g, 6%), and the mixture was heated at 85–90° C. for 0.75 h. Water was added and the mixture was extracted three times with dichloromethane, was dried (magnesium sulfate) and was evaporated. Purification by flash chromatography (silica gel, 45%EtOAc/hexane) provided the titled compound as a yellowish solid (0.60 g, 83%). Trituration from dichloromethane-hexanes provided a white solid. mp 113–114° C.

Example 15

Preparation of (+/−)-methyl 3-(2-aminopyrimidin-5-ylethynyl)-3-(3-cyclopentyloxy-4-methoxyphenyl) propionate To a suspension of sodium methoxide (0.12 g, 2.2 mmol) in methanol (20 mL) was added the compound from Example 14 (0.26 g, 0.60 mmol). The mixture was heated at reflux for 1 h (forming a solution) and was cooled. Water was added and the mixture was extracted three times with dichloromethane, was dried (magnesium sulfate) and the solvent was evaporated. Purification by flash chromatography (silica gel, 40% EtOAc/hexane) provided the titled compound (0.17 g, 73%) as a waxy white solid. Trituration from dichloromethane-hexanes provided a fine white solid. mp 117–118° C.

Example 16

Preparation of (+/−)-methyl-3-(4-carboxyphenyl) ethynyl-3-(3-cyclopentyloxy-4-methoxyphenyl) propionate 16(a) (+/−)-Methyl-3-(4-carbomethoxyphenyl)ethynyl-3-(3-cyclopentyloxy-4-methoxyphenyl)propionate Following the procedure of Example 8(e), except substituting methyl 3-iodobenzoate for 1-iodo-3-(5-methyl-[1,3,4]thiadiazol-2-yl)benzene, the titled compound was prepared as a yellow oil. Anal. (C$_{26}$H$_{28}$O$_6$) calcd: C, 71.54; H, 6.47. found: C, 71.55; H, 6.74.

16(b) (+/−)-Methyl-3-(4-carboxyphenyl)ethynyl-3-(3-cyclopentyloxy-4-methoxyphenyl)propionate NaOH (0.04 g, 0.9 mmol) was added to a solution of the compound from Example 16(a) (0.4 g, 0.9 mmol) in 5:2 methanol/water. After 36 h, the mixture was acidified with 3N HCl and evaporated. Purification by flash chromatography (silica gel, 5% MeOH/CHCl$_3$) provided the titled compound as a white solid. m.p. 109–110° C.

Example 17

Preparation of (+/−)-3-(3-cyclopentyloxy-4-methoxyphenyl)-3-phenylethynylpropionic acid amide 17(a) (+/−)-3-(3-Cyclopentyloxy-4-methoxyphenyl)-3-phenylethynylpropionic acid chloride A solution of the compound from Example 1(c) (3.6 g, 10 mmol) in benzene (75 mL) and DMF (0.1 mL) was cooled to 5° C. and treated with oxalyl chloride (2 mL). After the addition, the reaction was warmed to 23° C., stirred for 15 min, and the solvents removed. Additional benzene (75 mL) was added to the residue, and the solvent removed again., giving the titled compound as a yellow oil (100%). IR(neat) 1800 cm$^{-1}$ 17(b) (+/−)-3-(3-Cyclopentyloxy-4-methoxyphenyl)-3-phenylethynylpropionic acid amide A solution of the compound from Example 17(a) (3.8 g, 10 mmol) in acetone (30 mL) was slowly added to a cold (−20° C.), well stirred mixture of NH$_4$OH (30 mL) and acetone (50 mL), the addition at such a rate so the internal temperature does not rise above 0°. The reaction was stirred at 0° C. for 30 min, diluted with water (100 mL), and the solid filtered. The solid was washed well with water, dried, and recrystallized from EtOH and gave the titled compound (3.32 g, 92%). mp 142–144° C.

Example 18

Preparation of (+/−)-N-methyl-3-(3-cyclopentyloxy-4-methoxyphenyl)-3-phenylethynylpropionic acid amide Following the procedure of Example 17(b), except substituting a solution of methylamine for NH$_4$OH, the titled compound was prepared (65%). mp 127–131° C.

Example 19

Preparation of (+/−)-N,N-dimethyl-3-(3-cyclopentyloxy-4-methoxyphenyl)-3-phenylethynylpropionic acid amide Following the procedure of Example 17(b), except substituting a solution of dimethylamine for NH$_4$OH, the titled compound was prepared, and purified by crystallization from acetone/hexane (45%). mp 87–89° C.

Example 20

Preparation of (+/−)-N-[3-(3-cyclopentyloxy-4-methoxyphenyl)-3-phenylethynyl] propionylmorpholine Following the procedure of Example 17(b), except substituting an excess of morpholine for $NH_4OH$, the titled compound was prepared, and purified by flash chromatography (alumina, neutral, activity 1, 10% ether/$CH_2Cl_2$) (49%). $^1H$ NMR (400 MHz, $CDCl_3$) δ 7.42 (m, 2 H), 7.28 (m, 3 H), 7.00 (m, 2 H), 6.82 (d, 1 H), 4.80 (m, 1 H), 4.46 (t, 1 H), 3.84 (s, 3 H), 3.62 (m, 4 H), 3.58 (m, 1 H), 3.28–3.48 (m, 3 H), 2.92 (dd, 1 H), 2.76 (dd, 1 H), 1.78–1.98 (m, 6 H), 1.60 (m, 2 H).

Example 21

Preparation of (+/−)-N-methoxy-3-(3-cyclopentyloxy-4-methoxyphenyl)-3-phenylethynylpropionic acid amide The compound from Example 17(a) (525 mg, 1.37 mmol) in $CH_2Cl_2$ (20 mL) was slowly added to a cold (0° C.) solution of O-methylhydroxylamine hydrochloride (570 mg, 6.85 mmol) and triethylamine (690 mg, 6.85 mmol), and the reaction was stirred in the cold for 2 h. After washing the reaction with water, dilute aqueous HCl and aqueous $NaHCO_3$, the organic layer was dried ($CaSO_4$), and the solvent evaporated. The residue was recrystallized from ether/hexane, and gave the titled compound (460 mg, 84%). mp 111–114° C.

Example 22

Preparation of (+/−)-N-(thiazol-2-yl)-3-(3-cyclopentyloxy-4-methoxyphenyl)-3-phenylethynylpropionamide Following the procedure of Example 17(b), except substituting 2-aminothiazole for $NH_4OH$, the titled compound was prepared (56%). m.p. 142–144° C.

Example 23

Preparation of (+/−)-1-methyl4-[2-(3-cyclopentyloxy-4-methoxyphenyl)-4-phenylbut-3-ynoyl]piperazine, hydrochloride Following the procedure of Example 17(b), except substituting an excess of N-methylpiperazine for $NH_4OH$, the titled compound was prepared. The compound was purified by conversion to the HCl salt in $CHCl_3$ and ether, followed by recrstallization from i-propanol/ether (38%). mp 196–199° C.

Example 24

Preparation of (+/−)-1,1-dimethyl-4-[2-(3-cyclopentyloxy-4-methoxyphenyl)-4-phenylbut-3-ynoyl]piperazinium iodide The compound from Example 23 (60 mg, 0.12 mmol) was stirred in a mixture of ether (10 mL) and aqueous NaOH (0.1M, 10 mL). The ether was seperated, dried ($CaSO_4$), and the solvent evaporated. The residue was dissolved in acetone (3 mL), and treated with MeI (0.4 mL). After 30 min at 23° C., the reaction was diluted with ether (5 mL), chilled, and the crystalline titled compound was filtered (60 mg, 82%). mp 222–230° C.

Example 25

Preparation of (+/−)-N-methyl-N-(thiazol-2-yl)-3-(3-cyclopentyloxy-4-methoxyphenyl)-3-phenylethynylpropionamide To a solution of the compound from Example 22 (0.07 g, 0.16 mmol) in THF (2 mL) under an argon atmosphere was added 60% NaH/mineral oil suspension (0.008 g, 0.19 mmol), followed by methyl iodide (0.012 mL, 0.19 mmol). After heating at 80° C. for 0.25 h, the mixture was cooled to room temperature, was diluted with ethyl acetate, was washed with brine, was dried ($MgSO_4$) and was evaporated. Purification by flash chromatography, eluting with 1:1 hexanes/ethyl acetate provided the title compound as a yellow resin (0.025 g, 34%). Anal. ($C_{27}H_{28}N_2SO_3 \cdot 0.375 H_2O$) calcd: C, 69.39; H, 6.20; N, 5.99. found: C, 69.52; H, 6.22; N, 5.78.

Example 26

Preparation of (+/−)-t-butyl-(3-cyclopentyloxy-4-methoxyphenyl)-3-phenylethynylpropionate A solution of the compound from Example 17(a) (235 mg, 0.62 mmol) in ether (10 mL) was added to a solution of t-butanol (222 mg, 3 mmol) and dimethylaniline (75 mg, 0.62 mmol) in ether (50 mL) at 0° C., and stirring was continued for 24 h at 23° C. The reaction was washed with water, and 1N HCl, the organic layer was dried ($CaSO_4$) and the solvent removed. Purification by flash chromatography (alumina, neutral, activity 1, ether) gave the titled compound (65 mg, 25%). mp 54–58° C.

Example 27

Preparation of (+/−)-3-(3-cyclopentyloxy-4-methoxyphenyl)-5-phenylpent-4-ynol

The compound from Example 17(a) (320 mg, 0.82 mmol) in dimethoxyethane (5mL) was cooled to 0° C. and treated with $NaBH_4$ (100 mg). After 30 min, the reaction was quenched by the addition of 1N HCl (10 mL), diluted with water (50 mL), and extracted with ether. The extracts were washed with water, dried ($CaSO_4$), and the solvent evaporated. The residue was purified by flash chromatography (silica, 30% EtOAc/hexane) and gave the titled compound (195 mg, 90%). $^1H$ NMR (400 MHz, $CDCl_3$) δ 7.45 (m, 2 H), 7.30 (m, 3 H), 6.98 (s, 1 H), 6.95 (d, 1 H), 6.80 (d, 1 H), 4.80 (m, 1 H), 4.00 (t, 1 H), 3.88 (m, 1 H), 3.82 (s, 3 H), 3.78 (m, 1 H), 2.05 (m, 2 H), 1.78–1.96 (m, 7 H), 1.60 (m, 2 H).

Example 28

Preparation of (+/−)4(3-cyclopentyloxy-4-methoxyphenyl)-6-phenylhex-5-yn-2-one

The compound from Example 17(a) (320 mg, 0.82 mmol) in $CH_2Cl_2$ (5 mL) was added to a cold (0° C.) solution of Meldrum's acid (130 mg, 0.91 mmol) and pyridine (72 mg, 0.91 mmole) and the reaction was stirred at 0° C. for 6 h. The solvent was removed, and the residue dissolved in a mixture of HOAc (5 mL) and water (0.3 mL), the solution was refluxed for 3 h, and all the solvents were removed. The residue wastaken up in ether, washed with water, 1N NaOH, 1N HCl, dried ($CaSO_4$), and the solvent removed. The residue was crystallized from cyclohexane/hexane, and gave the titled compound (105 mg, 35%). mp 62–64° C.

Example 29

Preparation of (+/−)-3-[2-(3-cyclopentyloxy-4-methoxyphenyl)-4-phenylbut-3-ynyl]-5-methyl-1,2,4-oxadiazole 29(a) (+/−)-3-(3-Cyclopentyloxy-4-methoxyphenyl)-3-phenylethynylpropionitrile The compound from Example 17(c) (3.17 g, 8.73 mmol) and pyridine (3.13 g, 40 mmol) in $CH_2Cl_2$ (50 mL) was cooled to 0° C. and treated slowly with trifluoracetic anhydride (3.0 g, 14.2 mmol), and stirred for 45 min. The reaction was washed with water, 0.5N HCl, aqueous $NaHCO_3$, dried ($CaSO_4$), and the solvent evaporated. Purification by flash chromatography (silica gel, 20% EtOAc/hexane) gave the titled compound (2.7 g, 89%). $^1$H NMR (400 MHz, $CDCl_3$) δ 7.48 (m, 2 H), 7.32 (m, 3 H), 7.04 (d, 1 H), 7.00 (dd, 1 H), 6.86 (d, 1 H), 4.82 (m, 1 H), 4.18 (t, 1 H), 3.84 (s, 3 H), 2.88 (d, 2 H), 1.95 (m, 4 H), 1.86 (m, 2 H), 1.62 (m, 2 H).

29(b) (+/−)-N-Hydroxy-3-(3-cyclopentyloxy-4-methoxyphenyl)-3-phenylethynyl propanamidine The compound of Example 29(a) (490 mg, 1.42 mmol) in EtOH (25mL) was treated with a solution of hydroxylamine hydrochloride (460 mg, 6.7 mmol) in $H_2O$ (2.5 mL) and $K_2CO_3$ (460 mg, 3.35 mmol) in $H_2O$ (2.5 mL). The reaction was heated at 55° C. for 24 h, diluted with $H_2O$ (100 mL), and extracted with ether. The extracts were washed with $H_2O$, dried ($CaSO_4$), and the solvent removed. The residue was purified by flash chromatography (silica gel, eluting first with 25% ether/$CH_2Cl_2$, then ether), and gave the titled compound (400 mg, 74%). $^1$H NMR (400 MHz, $CDCl_3$) d 8.80 (s, 1 H), 7.47 (m, 2 H), 7.30 (m, 3 H), 6.98 (m, 2 H), 6.80 (d, 2 H), 4.82 (s, 1 H), 4.80 (m, 1 H), 4.08 (t, 1 H), 3.82 (s, 3 H), 2.64 (m, 2 H), 1.90 (m, 4 H), 1.82 (m, 2 H), 1.60 (m, 2 H).

29(c) (+/−)-3-[2-(3-cyclopentyloxy-4-methoxyphenyl)-4-phenylbut-3-ynyl]-5-methyl- 1,2,4-oxadiazole The compound from Example 29(b) (400 mg, 1.06 mmol) in $CH_2Cl_2$ (10 mL) at 0° C. was treated with triethylamine (117 mg, 1.16 mmol) and acetyl chloride (91 mg, 1.16 mmol), and stirred for 30. min. The reaction was washed with $H_2O$, 0.1N HCl, aqueous $NaHCO_3$, dried ($CaSO_4$), and the solvent evaporated. The residue was dissolved in toluene (10 mL), treated with triethylamine hydrochloride (2 mg), and refluxed for 12 h. The solvent was evaporated, and the residue purified by flash chromatography (alumina, neutral, activity 1, ether), and gave the titled compound (300 mg, 53%). mp 86–90° C.

Example 30

Preparation of (+/−)-3-[2-(3-cyclopentyloxy-4-methoxyphenyl)-4phenylbut-3-ynyl]-5-trifluoromethyl- 1,2,4-oxadiazole The compound of Example 29(b) (156 mg, 0.41 mmol) in toluene (10 mL) was treated with trifluoroacetic anhydride (0.5 mL) at 23° C. for 30 min and 105° C. for 10 min. The reaction was cooled, diluted with ether (50 mL), washed with $H_2O$, aqueous $NaHCO_3$, dried ($CaSO_4$), and the solvent evaporated. The residue was purified by flash chromatography (silica gel, 40% $CH_2Cl_2$/10% ether/hexane) and gave the titled product, which was further purified by recrystallization from hexane (100 mg, 53%). mp 96–98° C.

Example 31

Preparation of (+/−)-3-[2-(3cyclopentyloxy-4-methoxyphenyl)-4-phenylbut-3-ynyl]-1,2,4-oxadiazole The compound from Example 29(b) (93 mg, 0.25 mmol) in triethylorthoformate (3 mL) was heated at 130° C. for 30 min. The solvents were removed, and the residue purified by flash chromatography (alumina, neutral, activity 1, 20% ether/$CH_2Cl_2$) and gave the titled compound (13 mg, 13%). $^1$H NMR (400 MHz, $CDCl_3$) δ 8.66 (s, 1 H), 7.38 (m, 2 H), 7.30 (m, 3 H), 6.98 (m, 2 H), 6.84 (d, 1 H), 4.78 (m, 1 H), 4.39 (dd, 1 H), 3.82 (s, 3 H), 3.36 (dd, 1 H), 3.26 (dd, 1 H), 1.92 (m, 6 H), 1.60 (m, 2 H).

Example 32

Preparation of (+/−)-5-[2-(3-cyclopentyloxy-4-methoxyphenyl)-4-phenylbut-3-ynyl]tetrazole 32(a) (+/−)-N-(2-Cyanoethyl)-3-(3-cyclopentyloxy-4-methoxyphenyl)-3-phenylethynylpropionic acid amide Following the procedure from Example 17(b), except substituting 3-aminopropionitrile for $NH_4OH$, the titled compound was prepared (80%). $^1$H NMR (400 MHz, $CDCl_3$) 8 7.42 (m, 2 H), 7.30 (m, 3 H), 6.97 (m, 2 H), 6.83 (d, 2 H), 6.22 (t, 1 H), 4.77 (m, 1 H), 4.34 (t, 1 H), 3.82 (s, 3 H), 3.46 (m. 2 H), 2.73 (dd, 1 H), 2.64 (dd, 1 H), 2.52 (m, 2 H), 1.76–1.98 (m, 6 H), 1.60 (m, 2 H).

32(b) (+/−)-1-(2-cyanoethyl) 5-[2-(3-cyclopentyloxy-4-methoxyphenyl)-4-phenylbut-3-ynyl]tetrazole The compound from Example 32(a) (900 mg, 2.16 mmol) in THF (20 mL) was treated with triphenylphosphine (1.13 g, 4.33 mmol), diethylazodicarboxylate (753 mg, 4.33 mmol), and azidotrimethylsilane (498 mg, 4.33 mmol), and the reaction was stirred at 23° C. for 18 hr. Excess azide was decomposed by treatment of the reaction with aqueous ceric ammonium nitrate, and following dilution with $H_2O$ (50 mL) the mixture was extracted with ether. The extracts were washed with $H_2O$, dried ($CaSO_4$) and the solvent removed. The residue was purified by flash chromatography (silica gel, 50% EtOAc/hexane, and gave the titled product (680 mg, 71%). $^1$H NMR (400 MHz, $CDCl_3$) δ 7.40 (m, 2 H), 7.32 (m, 3 H), 6.90 (d, 1 H), 6.84 (d, 1 H), 6.80 (s, 1 H), 4.69 (m, 1 H), 4.38 (t, 1 H), 4.18 (m, 2 H), 3.82 (s, 3 H), 3.54 (dd, 1 H), 3.38 (dd, 1 H), 2.80 (m, 1 H), 2.68 (m, 1 H), 1.76–1.98 (m, 6 H), 1.62 (m, 2 H).

32(c) (+/−)-5-[2-(3-Cyclopentyloxy-4-methoxyphenyl)-4-phenylbut-3-ynyl]tetrazole The compound from Example 32(b) (500 mg, 1.13 mmol) in MeOH (8 mL) was treated with NaOH (2.5N, 0.6 mL). After 5 min, the reaction was diluted with $H_2O$ (20 mL), filtered, the filtrate acidified, and extracted with ether. The extracts were washed with $H_2O$, dried ($CaSO_4$), and the solvent evaporated. Purification of the residue by flash chromatography (silica gel, 2% MeOH/EtOAc) gave the titled compound (110 mg, 25%). $^1$H NMR (400 MHz, $CDCl_3$) δ 7.38 (m, 2 H), 7.30 (m, 3 H), 6.92 (m, 2 H), 6.80 (d, 1 H), 5.34 (br s, 1 H), 4,76 (m, 1 H), 4.36 (t, 1 H), 3.82 (s, 3 H), 3.50 (d, 2 H), 1.72–1.98 (m, 6 H), 1.60 (m, 2 H).

Example 33

Preparation of (+/−)-1-methyl-5-[2-(3-cyclopentyloxy-4-methoxyphenyl)-4-phenylbut-3-ynyl]tetrazole Following the procedure of Example 32(b), except substituting the compound from Example 18 for (+/−)-N-(2-cyanoethyl)-3-(3-cyclopentyloxy-4-methoxyphenyl)-3-phenylethynylpropionic acid amide gave the titled compound (12%). $^1$H NMR (400 MHz, $CDCl_3$) δ 7.40 (m, 2 H), 7.32 (m, 3 H), 6.86 (m, 3 H), 4.70 (m, 1 H), 4.36 (t, 1 H), 3.86 (s, 3 H), 3.66 (s, 3 H), 3.47 (dd, 1 H), 3.30 (dd, 1 H), 1.78–1.94 (m, 6 H), 1.60 (m, 2 H).

Example 34

Preparation of (+/−)-methyl-3-(3-cyclopentyloxy-4-methoxyphenyl)-3-[3-(3-methyl-[1,2,4]oxadiazol-5-yl)phenylethynyl]propionate Following the procedure of Example 8(e), except substituting 1-iodo-3-(3-methyl-[1,2,4]oxadiazol-5-yl)benzene for 1-iodo-3-(5-methyl-[1,3,4]thiadiazol-2-yl)benzene the titled compound was prepared (67%). mp 66–68.5° C.

Example 35

Preparation of (+/−)-Ethyl-3-(3-Cyclopentyloxy-4-methoxyphenyl)3-phenylethynylpropionate A solution of (+/−)-3-(3-cyclopentyloxy-4-methoxyphenyl)-3-phenylethynylpropionic acid (250 mg, 0.69 mmol) in EtOH (20 ml) and $H_2SO_4$ (1 drop) was refluxed for 6 hr. The solvent was evaporated, the residue taken up in $Et_2O$, washed with aqueous $Na_2CO_3$, dried, and the solvent evaporated. The residue was crystallized from hexane, and gave the titled compound, 180 mg (67%). $^1H$ NMR (400 MHz, CDCl$_3$) δ 7.40 (m, 2 H), 7.28 (m, 3 H), 6.98 (m, 2 H), 6.82 (d, 1 H), 4.80 (m, 1 H), 4.32 (t, 1 H), 4.14 (q, 2 H), 3.80 (s, 3 H), 2.86 (d of d, 1 H), 2.76 (d of d, 1 H), 1.76–1.98 (m, 6 H), 1.62 (m, 2 H), 1.22 (t, 3 H).

Example 36

Preparation of (+/−)-i-Propyl-3-(3-Cyclopentyloxy-4-methoxyphenyl)-3-phenylethynylpropionate A solution of (+/−)-3-(3-cyclopentyloxy-4-methoxyphenyl)-3-phenylethynylpropionic acid chloride (150 mg, 0.42 mmol) and dimethylaniline (100 mg, 0.83 mmol) in $Et_2O$ (5 ml) was treated with i-propanol (1 ml) and stirred at 23° for 18 hr. The solvents were evaporated, and the residue taken up in $Et_2O$, washed with 3N HCl, $H_2O$, dried, and the solvent evaporated. The residue was purified by flash chromatography (silica gel, 20% EtOAc/hexane), and gave the titled compound, 82 mg (54%). MP . $^1H$ NMR (400 MHz, CDCl$_3$) δ 7.38 (m, 2 H), 7.30 (m, 3 H), 6.94 (m, 2 H), 6.78 (d, 1 H), 5.02 (m, 1 H), 4.78 (m, 1 H), 4.30 (t, 1 H), 3.80 (s, 3 H), 2.82 (d of d, 1 H), 2.72 (d of d, 1 H), 1.78–1.96 (m, 6 H), 1.60 (m, 2 H), 1.22 (d, 3 H), 1.16 (d, 3 H).

Example 37

Preparation of (+/−)-n-Propyl-3-(3-Cyclopentyloxy-4-methoxyphenyl)-3-phenylethynylpropionate A solution of (+/−)-3-(3-cyclopentyloxy-4-methoxyphenyl)-3-phenylethynylpropionic acid (200 mg, 0.55 mmol) in n-propanol (15 ml) and conc. $H_2SO_4$ (1 drop) was heated at 95° for 5 hr. The solvents were evaporated, the residue taken up in $Et_2O$, washed with $H_2O$, aqueous $K_2CO_3$, dried and the solvent evaporated. The residue was purified by flash chromatography (alumina, neutral, activity 1, $Et_2O$), and gave the titled compound as an oil, 125 mg (56%). $^1H$ NMR (400 MHz, CDCl$_3$) δ 7.40 (m, 2 H), 7.28 (m, 3 H), 6.98 (m, 2 H), 6.84 (d, 1 H), 4.80 (m, 1 H), 4.36 (t, 1 H), 4.06 (t, 2 H), 3.82 (s, 3 H), 2.90 (d of d, 1 H), 2.78 (d of d, 1 H), 1.78–1.96 (m, 6 H), 1.64 (m, 4 H), 0.90 (t, 3 H).

Example 38

Preparation of (+/−)-1-Phenyl-3-(3-cyclopentyloxy-4-methoxyphenyl)-5-oxohexyne

A solution of Meldrum's acid (130 mg, 0.91mmol) and pyridine (72 mg, 0.91 mmol) in $CH_2Cl_2$ (20 ml) at 0° was treated with a solution of (+1−)-3-(3-cyclopentyloxy-4-methoxyphenyl)-3-phenylethynylpropionic acid chloride (320 mg, 0.82 mmol) in $CH_2Cl_2$ (5 ml). The reaction was stirred at 0° for 6 hr, and the solvents were evaporated. The residue in HOAc (5 ml) and $H_2O$ (0.3 ml) was refluxed for 3 hr. The solvents were evaporated, and the residue taken up in $Et_2O$, washed with $H_2O$, 0.1N HCl, 0.1N NaOH, dried, and the solvent evaporated. The residue was crystallized from a mixture of cyclohexane and hexane, and gave the titled compound, 105 mg (35%). mp 62–64°. $^1H$ NMR (400 MHz, CDCl$_3$) δ 7.40 (m, 2 H), 7.27 (m, 3 H), 6.95 (m, 2 H), 6.80 (d, 1 H), 4.80 (m, 1 H), 4.33 (t, 1 H), 3.81 (s, 3 H), 3.02 (d of d, 1 H), 2.85 (d of d, 1 H), 2.16 (s, 3 H), 1.78–1.98 (m, 6 H), 1.60 (m, 2 H).

Example 39

Preparation of (+/−)-1-Methoxy-3-(3-cyclopentyloxy-4-methoxyphenyl)-5-phenyl-4-pentyne A solution of (+/−)-3-(3-cyclopentyloxy-4-methoxyphenyl)-5-phenylpent-4-ynol (175 mg, 0.5 mmol) in a mixture of glyme (7 ml) and DMF (2 ml) was treated with NaH (20 mg of a 60% dispersion in mineral oil), heated to 50° for 3 min, and cooled to 23°. MeI (0.5 ml) was added, and the mixture stirred for 18 hr. $Me_2SO_4$ (0.3 ml) was added, and the mixture was heated to 60° for 2 hr. The reaction was cooled, quenched with 50 ml cold 0.1N HCl, and extracted with $Et_2O$. The extracts were washed with $H_2O$, dried, and the solvent evaporated. Purification by flash chromatography (silica gel, 30% EtOAc in hexane) gave the titled compound, (26 mg 14%). $^1H$ NMR (400 MHz, CDCl$_3$) δ 7.42 (m, 2 H), 7.28 (m, 3 H), 6.96 (m, 2 H), 6.82 (d, 1 H), 4.80 (m, 1 H), 3.98 (t, 1 H), 3.84 (s, 3 H), 3.62 (m, 1 H), 3.48 (m, 1 H), 3.40 (s, 3 H), 2.06 (m, 2 H), 1.72–2.00 (m, 6 H), 1.62 (m, 2 H).

Example 40

Preparation of (+/−)-Methyl4(3-cyclopentlyoxy-4-methoxyphenyl)-4-phenylethynylbutyrate 40(a) (+/−)-1-Phenyl-3-(3-cyclopentyloxy-4-methoxyphenyl)-5-oxo-6-diazohexyne A solution of (+/−)-3-(3-cyclopentyloxy-4-methoxyphenyl)-3-phenylethynylpropionic acid chloride (1.06 mg, 3.1 mmol) in $Et_2O$ (10 ml) was added to a cold (0°) solution of $CH_2N_2$ (0.1 mol) in $Et_2O$ (75 ml), and the reaction was stirred in the cold for 1 hr. The ice bath was removed, and excess diazomethane was removed with a stream of Argon. The solvent was concentrated, hexane was added, and the titled product crystallized, (850 mg, 79%). $^1H$ NMR (400 MHz, CDCl$_3$) δ 7.42 (m, 2 H), 7.32 (m, 3 H), 6.96 (m, 2 H), 6.86 (d, 1 H), 5.26 (s, 1 H), 4.80 (m, 1 H), 4.38 (t, 1 H), 3.86 (s, 3 H), 2.88 (m, 1 H), 2.76 (m, 1 H), 1.72–2.00 (m, 6 H), 1.62 (m, 2 H).

40(b) (+/−)-Methyl4(3-cyclopentlyoxy-4-methoxyphenyl) 4-phenylethynylbutyrate (+/−)-1-Phenyl-3-(3-cyclopentyloxy-4-methoxyphenyl)-5-oxo-6-diazohexyne (180 mg, 0.52 mmol) was added portionwise to a refluxing suspension of silver benzoate (200 mg) in MeOH (20 ml). The mixture was refluxed for 15 min, cooled, filtered and the filtrate evaporated. The residue was dissolved in $Et_2O$, washed with $H_2O$, 0.01N HCl, dried, filtered, and the sovent evaporated. Purification by flash chromatography (silica gel, 30% $Et_2O$ in hexane) gave the titled product as a yellow oil. $^1H$ NMR (400 MHz, CDCl$_3$) δ 7.41 (m, 2 H), 7.28 (m, 3 H), 6.93 (m, 2 H), 6.83 (d, 1 H), 4.80 (m, 1 H), 3.88 (t, 1 H), 3.82 (s, 3 H), 3.65 (s, 3 H), 2.50 (m, 2 H), 2.14 (m, 2 H), 1.72–2.00 (m, 6 H), 1.62 (m, 2 H).

Example 41

Preparation of (+/−)-4-(3-cyclopentlyoxy-4-methoxyphenyl)-6-phenylhex-5-ynoic acid A solution of (+/−)-methyl-4-(3-cyclopentlyoxy-4-methoxyphenyl)-4-phenylethynylbutyrate (45 mg, 0.13 mmol) in EtOH (2 ml) was treated with NaOH (0.05 ml of a 2.5N solution), and the mixture was heated to 50° for 45 min. The mixture was cooled, diluted with H₂O, acidified with 3N HCl and extracted with Et₂O. The extracts were washed with H₂O, dried, and the solvent evaporated. Purification by flash chromatography (silica gel, Et₂O followed by 0.5% HOAc in Et₂O) gave the titled compound (32 mg, 74%). $^1$H NMR (400 MHz, CDCl₃) δ 7.42 (m, 2 H), 7.32 (m, 3 H), 6.93 (m, 2 H), 6.84 (d, 1 H), 4.80 (m, 1 H), 3.92 (t, 1 H), 3.84 (s, 3 H), 2.56 (m, 2 H), 2.14 (m, 2 H), 1.68–2.00 (m, 6 H), 1.60 (m, 2 H).

Example 42

Preparation of (+/−)-1-Phenyl-3-(3-cyclopentyloxy-4-methoxyphenyl)-5-oxo-6-hydroxyhexyne 42(a) (+/−)-1-Phenyl-3-(3-cyclopentyloxy-4-methoxyphenyl)-5-oxo-6-acetoxyhexyne A solution of (+/−)-1-phenyl-3-(3-cyclopentyloxy-4-methoxyphenyl)-5-oxo-6-diazohexyne (190 mg, 0.55 mmol) in HOAc (1 ml) was heated to 70° for 30 min. The reaction was cooled, diluted with H2O, and extracted with CHCl3. The extracts were washed with H2O, 5% NaHCO3, dried, and the solvent evaporated. Purification by flash chromatography (silica gel, 50% Et2O in hexane) gave the titled compound as an oil (132 mg, 63%). $^1$H NMR (400 MHz, CDCl₃ ) δ 7.42 (m, 2 H), 7.30 (m, 3 H), 6.96 (m, 2 H), 6.82 (d, 1 H), 4.80 (m, 1 H), 4.72 (d, 1 H), 4.56 (d, 1 H), 4.36 (t, 1 H), 3.86 (s, 3 H), 3.04 (d of d, 1 H), 2.85 (d of d, 1 H), 2.16 (s, 3 H), 1.72–2.00 (m, 6 H), 1.54–1.64 (m, 2 H).

42(b) (+/−)-1-Phenyl-3-(3-cyclopentyloxy-4-methoxyphenyl)-5-oxo-6-hydroxyhexyne

A solution of (+/−)-1-phenyl-3-(3-cyclopentyloxy-4-methoxyphenyl)-5-oxo-6-acetoxyhexyne (130 mg, 0.34 mmol) in MeOH (2 ml) was treated with NaOH ( 0.1 ml of a 2.5N solution), and the mixture was stirred at 23° for 3.5 hr. The reaction was diluted with H₂O, and extracted with Et₂O. The extracts were washed with H₂O, dried, and the solvent removed. Purification by flash chromatography (silica gel, 50% Et₂O in CH₂Cl₂) gave the titled compound as an oil (32 mg, 28%). $^1$H NMR (400 MHz, CDCl₃) δ 7.42 (m, 2 H), 7.32 (m, 3 H), 6.98 (m, 2 H), 6.86 (d, 1 H), 4.80 (m, 1 H), 4.38 (t, 1 H), 4.32 (d, 1 H), 4.14 (d, 1 H), 3.84 (s, 3 H), 3.00 (d of d, 1 H), 2.86 (d of d, 1 H), 1.68–2.00 (m, 6 H), 1.62 (m, 2 H).

Example 43

Preparation of (+/−)-1-Phenyl-3-(3-cyclopentyloxy-4-methoxyphenyl)-5-oxo-6-methoxyhexyne (+/−)-1-Phenyl-3-(3-cyclopentyloxy-4-methoxyphenyl)-5-oxo-6-diazohexyne (120 mg, 0.35 mmol) was added portionwise to a refluxing solution of BF₃·Et₂O (0.5 ml) in MeOH (20 ml). After 5 min, the solvent was concentrated, the reaction diluted with H₂O, basified with NaHCO₃, and extracted with Et₂O. The extracts were washed with H₂O, dried, and the solvent removed. Purification by flash chromatography (silica gel, 30% Et₂O in hexane) gave the titled product (4.8 mg, 4%). $^1$H NMR (400 MHz, CDCl₃) δ 7.42 (m, 2 H), 7.30 (m, 3 H), 6.98 (m, 2 H), 6.84 (d, 1 H), 4.80 (m, 1 H), 4.40 (t, 1 H), 4.06 (d, 1 H), 3.92 (d, 1 H), 3.84 (s, 3 H), 3.38 (s, 3 H), 3.04 (d of d, 1 H), 2.88 (d of d, 1 H), 1.68–2.00 (m, 6 H), 1.58 (m, 2 H).

Example 44

Preparation of (+/−)-Methyl-2-carbomethoxy-3-(3-cyclopentyloxy-4-methoxyphenyl)-5-phenylpent-4-ynoate A solution of (+/−)-2,2-dimethyl-5-([1-(3-cyclopentyloxy-4-methoxyphenyl)-3-phenyl]prop-2-yne)-1,3-dioxane-4,6-dione (160 mg, 0.36 mmol) in MeOH (5 ml) was treated with HCl (0.5 ml of a 1N solution in Et₂O) and refluxed for 2 hr. The solvent was evaporated, and the residue was chromatographed (alumina, neutral, Activity I, 5% Et₂O in CH₂Cl₂) and gave the titled compound (72 mg, 46%), mp 66–67°. $^1$H NMR (400 MHz, CDCl₃) δ 7.38 (m, 2 H), 7.30 (m, 3 H), 6.98 (m, 2 H), 6.82 (d, 1 H), 4.78 (m, 1 H), 4.58 (d, 1 H), 3.83 (d, 1 H), 3.82 (3, 3 H), 3.80 (s, 3 H), 3.60 (s, 3 H), 1.78–2.00 (m, 6 H), 1.58 (m, 2 H).

Example 45

Preparation of (+/−)-Methyl-3-(3-cyclopentyloxy-4-methoxyphenyl)-2-methyl-5-phenylpent-4-ynoate A solution of (+/−)-methyl-(3-cyclopentyloxy-4methoxyphenyl)-3-phenylethynylpropionate (190 mg, 0.5 mmol) in THF (20 ml) cooled to −78° was treated with lithium hexamethyldisilazide (0.55 ml of a 1N solution in hexane), and excess MeI. After stirring at −78° for 1 hr, the reaction was quenched with cold 0.05N Hcl, and extracted with Et₂O. The extracts were washed with dilute HCl, H₂O, dried and evaporated. Purification by flash chromatography (silica gel, hexane:CH₂Cl₂:Et₂O 70:30:4), followed by crystallization from hexane gave the titled compound (80 mg, 41%), mp 52–54°. $^1$H NMR (400 MHz, CDCl₃) δ 7.45 (m, 2 H), 7.30 (m, 3 H), 6.95 (m, 2 H), 6.82 (d, 1 H), 4.80 (m, 1 H), 4.26 (d, 1 H), 3.84 (3, 3 H), 3.62 (s, 3 H), 2.84 (t, 1 H), 1.78–1.96 (m, 6 H), 1.62 (m, 2 H), 1.34 (d, 3 H).

Example 46

Preparation of (+/−)-Methyl-3-(3-cyclopentyloxy-4-methoxyphenyl)-2-thiomethyl-5-phenylpent-4-ynoate A solution of (+/−)-methyl-(3-cyclopentyloxy-4-methoxyphenyl)-3-phenylethynylpropionate (100 mg, 0.26 mmol) in THF (8 ml), at −78° was treated with lithium hexamethyldisilazide (0.3 ml of a 1N solution in hexane) and stirred for 5 min. HMPA (0.2 ml) was added, followed by MeSSO₂Me (35 mg, 0.28 mmol). The reaction was stirred at −78° for 60 min, poured into cold 0.05N HCl (50 ml), and extractred with Et₂O. The extracts were washed with HCl, H₂O, dried, and the solvent evaporated. Purification by flash chromatography (alumina, neutral, Activity I; hexane:CH₂Cl₂:Et₂O/75:25:50), followed by crystallization from hexane gave the titled compound (36 mg, 33%), mp 64–72°. $^1$H NMR of major isomer (400 MHz, CDCl₃) δ 7.44 (m, 2 H), 7.30 (m, 3 H), 6.96 (m, 2 H), 6.80 (d, 1 H), 4.80 (m, 1 H), 4.30 (d, 1 H), 3.84 (3, 3 H), 3.60 (s, 3 H), 3.56 (d, 1 H), 2.28 (s, 3 H), 1.78–1.96 (m, 6 H), 1.62 (m, 2 H).

Example 47

Preparation of (R)-methyl-3-(3-cyclopentyloxy-4-methoxyphenyl)-3-ethynylpropionate and (S)-methyl-3-(3-cyclopentyloxy-4-methoxyphenyl)3-ethynylpropionate A mixture of (R,S)-methyl-3-(3-cyclopentyloxy-4-methoxyphenyl)-3-ethynylpropionate was seperated by HPLC, using a Diacel Chiralpack AD column, 21.2×250 mm, 85:15/hexane:isopropanol as the mobile phase at 10 ml/min with uv detection at 302 nm, and 200 mg injections. (R)-methyl-3-(3-cyclopentyloxy-4-methoxyphenyl)-3-ethynylpropionate, mp 64–66°, had retention time of 11.0 min, and (S)-methyl-3-(3-cyclopentyloxy-4-methoxyphenyl)-3-ethynylpropionate had retention time of 14.4min.

Example 48

Preparation of (R)-methyl-3-(3-cyclopentyloxy-4-methoxyphenyl)-3-phenylethynylpropionate and (S)-methyl-3-(3-cyclopentyloxy-4-methoxyphenyl)-3-phenylethynylpropionate A mixture of (R,S)-methyl-3-(3-cyclopentyloxy-4-methoxyphenyl)-3-phenylethynylpropionate was seperated by HPLC, using a Diacel Chiralpack AD column, 21.2×250 mm, 95:5/hexane:isopropanol as the mobile phase at 10 ml/min with uv detection at 295 nm, and 45 mg injections. (S)-methyl-3-(3-cyclopentyloxy-4-methoxyphenyl)-3-phenylethynylpropionate had retention time of 16.3 min, and (R)-methyl-3-(3-cyclopentyloxy-4-methoxyphenyl)-3-phenylethynylpropionate had retention time of 20.2 min.

Example 49

Preparation of (R)-3-(3-cyclopentyloxy-4-methoxyphenyl)-3-ethynylpropionic acid

A mixture of (R,S)-3-(3-cyclopentyloxy-4-methoxyphenyl)-3-ethynylpropionic acid was treated with a molar euivalent of (S)-α-methylbenzylamine, and the resultant salt was fractionally crystallized numerous times from acetonitrile and gave (S)-α-methylbenzylammonium·(R)-3-(3-cyclopentyloxy-4-methoxyphenyl)-3-ethynylpropionate, mp 126°. Treatment of the salt with aqueous HCl, followed by extraction with $Et_2O$ and evaporation of the solvent gave (R)-3-(3-cyclopentyloxy-4-methoxyphenyl)-3-ethynylpropionic acid, mp 101–102° C.

Example 50

Preparation of (S)-methyl-3-(3-cyclopentyloxy-4-methoxyphenyl)-5-[3-(3-methyl[1,2,4]oxadiazol-5-yl)phenyl]pent-4ynoate A solution of (R)-methyl-3-(3-cyclopentyloxy-4-methoxyphenyl)-3-ethynylpropionate (150 mg, 0.5 mmol) and 3-(3-methyl[1,2,4]oxadiazol-5-yl) iodobenzene (144 mg, 0.5 mmol) in $Et_3N$ (4 ml) was treated with tetrakis(triphenylphosphine)palladium(0) (10 mg) and copper(I) iodide (10 mg). The reaction was heated to 55° for 30 min, and then the solvent was thoroughly evaporated. The residue was purified by flash chromatography (silica gel $CH_2Cl_2$:hexane:$Et_2O$/10:10:1) and gave the titled compound as an oil (73 mg, 17%) $^1H$ NMR (400 MHz, $CDCl_3$) δ 8.18 (s, 1 H), 8.02 (m, 1 H), 7.60 (m, 1 H), 7.60 (t, 1 H), 6.95 (m, 2 H), 6.86 (d, 1 H), 4.80 (m, 1 H), 4.33 (t, 1 H), 3.84 (s, 3 H), 3.72 (s, 3 H), 2.92 (d of d, 1 H), 2.82 (d of d, 1 H), 2.48 (s, 3 H), 1.78–2.02 (m, 6 H), 1.62 (m, 2 H).

Proceeding in the same manner, using (R)-methyl-3-(3-cyclopentyloxy-4-methoxyphenyl)-3-ethynylpropionate but substituting for 3-(3-methyl[1,2,4]oxadiazol-5-yl) iodobenzene the appropriate aryliodide, the following compounds were made:

(S)-methyl 3-(3-cyclopentyloxy-4-methoxyphenyl)-3-(fluoren-2-ylethynyl)propionate;

(S)-methyl 3-(3-cyclopentyloxy-4-methoxyphenyl)-3-(3-methyl4N-phthalimidophenylethynyl)propionate;

(S)-methyl 3-(3-cyclopentyloxy-4-methoxyphenyl)-3-(4-methoxyethoxymethylphenylethynyl)propionate;

(S)-methyl 3-(3-cyclopentyloxy-4-methoxyphenyl)-3-(4N-veratrylaminophenylethynyl)propionate;

(S)-methyl 3-(3-cyclopentyloxy-4-methoxyphenyl)-3-(naphthalen-2-ylethynyl)propionate;

(S)-methyl 3-(3-cyclopentyloxy-4-methoxyphenyl)-3-(10,10-dioxo-phenoxathiin-2-ylethynyl)propionate;

(S)-methyl 3-(3-cyclopentyloxy-4-methoxyphenyl)-3-(1-acetylindolin-5-ylethynyl)propionate;

(S)-methyl 3-(3-cyclopentyloxy-4-methoxyphenyl)-3-(dibenzofuran-2-ylethynyl)propionate;

(S)-methyl 3-(3-cyclopentyloxy-4-methoxyphenyl)-3-(dibenzo-p-dioxin-2-ylethynyl)propionate;

(S)-methyl 3-(3-cyclopentyloxy-4-methoxyphenyl)-3-(4'-trifluoromethylbenzophenon-4-ylethynyl)propionate;

(S)-methyl 3-(3-cyclopentyloxy-4-methoxyphenyl)-3-(4chloro-3-fluorophenylethynyl)propionate;

(S)-methyl 3-(3-cyclopentyloxy-4-methoxyphenyl)-3-(3-chloro-4-fluorophenylethynyl)propionate;

(S)-methyl 3-(3-cyclopentyloxy-4-methoxyphenyl)-3-(3,4,difluorophenylethynyl)propionate;

(S)-methyl 3-(3-cyclopentyloxy-4-methoxyphenyl)-3-(3,5,-dinitrophenylethynyl)propionate;

(S)-methyl 3-(3-cyclopentyloxy-4-methoxyphenyl)-3-(4-difluoromethoxyphenylethynyl)propionate;

(S)-methyl 3-(3-cyclopentyloxy-4-methoxyphenyl)-3-(4-t-butylphenylethynyl)propionate;

(S)-methyl 3-(3-cyclopentyloxy-4-methoxyphenyl)-3-(3-fluoro-5-nitrophenylethynyl)propionate;

(S)-methyl 3-(3-cyclopentyloxy-4-methoxyphenyl)-3-(3-trifluoromethyl-phenylethynyl)propionate;

(S,S)-1,4-Bis[3-(cyclopentyloxy-4-methoxyphenyl-4-methoxycarbonylbutynyl]benzene;

(S)-methyl 3-(3-cyclopentyloxy-4-methoxyphenyl)-3-(3-fluorophenylethynyl)propionate;

(S)-methyl 3-(3-cyclopentyloxy-4-methoxyphenyl)-3-(4-fluorophenylethynyl)propionate;

(S)-methyl 3-(3-cyclopentyloxy-4-methoxyphenyl)-3-(4-methoxyphenylethynyl)propionate;

(S)-methyl 3-(3-cyclopentyloxy-4-methoxyphenyl)-3-(4-cyanophenylethynyl)propionate;

(S)-methyl 3-(3-cyclopentyloxy-4-methoxyphenyl)-3-[4pyrrol-1-yl)phenylethynyl]propionate;

(S)-methyl 3-(3-cyclopentyloxy-4-methoxyphenyl)-3-(3,5-bistrifluoromethylphenylethynyl)propionate;

(S)-methyl 3-(3-cyclopentyloxy-4-methoxyphenyl)-3-(2-formylfuran-5-ylethynyl)propionate;

(S)-methyl 3-(3-cyclopentyloxy-4-methoxyphenyl)-3-(naphthalen-1-ylethynyl)propionate;

(S)-methyl 3-(3-cyclopentyloxy-4-methoxyphenyl)-3-(3-cyanomethylphenylethynyl)propionate; SB-248025

(S)-methyl 3-(3-cyclopentyloxy-4-methoxyphenyl)-3-(4-nitrophenylethynyl)propionate;

(S)-methyl 3-(3-cyclopentyloxy-4-methoxyphenyl)-3-(3,5-dichlorophenylethynyl)propionate;

(S)-methyl 3-(3-cyclopentyloxy-4-methoxyphenyl)-3-(3,4-dichlorophenylethynyl)propionate;

(S)-methyl 3-(3-cyclopentyloxy-4-methoxyphenyl)-3-(3-chlorophenylethynyl)propionate;

(S)-methyl 3-(3-cyclopentyloxy-4-methoxyphenyl)-3-(3-acetophenylethynyl)propionate;

(S)-methyl 3-(3-cyclopentyloxy-4-methoxyphenyl)-3-(4-acetophenylethynyl)propionate;

(S)-methyl 3-(3-cyclopentyloxy-4-methoxyphenyl)-3-(4-cyanomethylphenylethynyl)propionate;

(S)-methyl 3-(3-cyclopentyloxy-4-methoxyphenyl)-3-(3-methoxyphenylethynyl)propionate;

(S)-methyl 3-(3-cyclopentyloxy-4-methoxyphenyl)-3-(4-chlorophenylethynyl)propionate;

(S)-methyl 3-(3-cyclopentyloxy-4-methoxyphenyl)-3-(3-cyanophenylethynyl)propionate;

(S)-methyl 3-(3-cyclopentyloxy-4-methoxyphenyl)-3-(4-[N-{2-(cyclohexylamino)acetamido}]phenylethynyl)propionate;

(S)-methyl 3-(3-cyclopentyloxy-4-methoxyphenyl)-3-(4-[N-{2-(pyrrolidino)acetamido}]phenylethynyl)propionate;

(S)-methyl 3-(3-cyclopentyloxy-4-methoxyphenyl)-3-(4-[N-{2-(benzylamino)acetamido}]phenylethynyl)propionate;

(S)-methyl 3-(3-cyclopentyloxy-4-methoxyphenyl)-3-(2,4 diethyloxazol-3-ylethynyl)propionate;

(S)-methyl 3-(3-cyclopentyloxy-4-methoxyphenyl)-3-(4-trifluoromethoxyphenylethynyl)propionate; and (S)-methyl 3-(3-cyclopentyloxy-4-methoxyphenyl)-3-(3-trifluoromethyl4-acetamidophenyl)propionate.

These esters may be converted to their corresponding acid or to salt by treating a given compound with a base, forming the salt, then acidifying that solution if needs be to obtain the acid.

Example 51

Preparation of (S)-methyl-3-(3-cyclopentyloxy-4-methoxyphenyl)-5-[3-(5-methyl[1,2,4]oxadiazol-3-yl)phenyl]pent-4-ynoate The titled compound was prepared following the procedure in Example 50, except and 3-(5-methyl[1,2,4]oxadiazol-3-yl) iodobenzene was substituted for and 3-(3-methyl[1,2,4]oxadiazol-5-yl) iodobenzene. $^1$H NMR (400 MHz, CDCl$_3$) δ 8.14 (s, 1 H), 8.00(d, 1 H), 7.52 (d, 1 H), 7.42 (t, 1 H), 6.94 (m, 2 H), 6.82 (d, 1 H), 4.80 (m, 1 H), 4.33 (t, 1 H), 3.84 (s, 3 H), 3.70 (s, 3 H), 2.92 (d of d, 1 H), 2.80 (d of d, 1 H), 2.66 (s, 3 H), 1.80–2.00 (m, 6 H), 1.62 (m, 2 H).

Example 52

Preparation of (+/−)-methyl-3-(3-carbomethoxyphenyl)ethynyl-3-(3-cyclopentyloxy-4-methoxyphenyl)propionate Following the procedure of Example 50, except substituting methyl 3-iodobenzoate for 3-(3-methyl[1,2,4]oxadiazol-5-yl) iodobenzene, and (+/−)-methyl-3-(3-cyclopentyloxy-4-methoxyphenyl)-3-ethynylpropionate for (R)-methyl-3-(3-cyclopentyloxy-4-methoxyphenyl)-3-ethynylpropionate the titled compound was prepared as a yellow oil (28%). Anal. (C$_{26}$H$_{28}$O$_6$) calcd: C, 71.54; H, 6.47. found: C, 71.30; H, 6.39.

Example 53

Preparation of (+/−)-methyl-3-(2-carbomethoxyphenyl)ethynyl-3-(3-cyclopentyloxy-4-methoxyphenyl)propionate Following the procedure of Example 50, except substituting methyl 2-iodobenzoate for 3-(3-methyl[1,2,4]oxadiazol-5-yl) iodobenzene, and (+/−)-methyl-3-(3-cyclopentyloxy-4-methoxyphenyl)-3-ethynylpropionate for (R)-methyl-3-(3-cyclopentyloxy-4-methoxyphenyl)-3-ethynylpropionate, the titled compound was prepared as a yellow oil (34%). Anal. (C$_{26}$H$_{28}$O$_6$) calcd: C, 71.54; H, 6.47. found; C, 71.44; H, 6.70.

Example 54

Preparation of (+/−)-methyl-3-(4-carbomethxyphenyl)ethynyl-3-(3-cyclopentyloxy-4-methoxyphenyl)propionate Following the procedure of Example 50, except substituting methyl 4-iodobenzoate for 3-(3-methyl[1,2,4]oxadiazol-5-yl) iodobenzene, and (+/−)-methyl-3-(3-cyclopentyloxy-4methoxyphenyl)-3-ethynylpropionate for (R)-methyl-3-(3-cyclopentyloxy-4-methoxyphenyl)-3-ethynylpropionate the titled compound was prepared as a yellow oil (81%). Anal. (C$_{26}$H$_{28}$O$_6$) calcd: C, 71.54; H, 6.47. found: C, 71.55; H, 6.74.

Example 55

Preparation of (+/−)-3-(4-carbomethxyphenyl)ethynyl-3-(3-cyclopentyloxy-4-methoxyphenyl) propionic acid To a solution of (+/−)-methyl-3-(4-carbomethxyphenyl)ethynyl-3-(3-cyclopentyloxy-4-methoxyphenyl)propionate (0.40 g, 0.91 mmol) in 5:2 methanol/water was added NaOH (0.04 g, 0.91 mmol). After 36 h, 3N HCl was added, the methanol was evaporated and the aqueous residue was extracted twice with CH$_2$Cl$_2$ and was evaporated. Purification by flash chromatography (silica gel, 5% CH$_3$OH/CHCl$_3$) provided the title compound as a white solid (0.04 g, 10%). mp 109–110° C.

Example 56

Preparation of (+/−)-3-(3-carbomethoxyphenyl)ethynyl-3-(3-cyclopentyloxy-4-methoxyphenyl) propionic acid To a solution of (+/−)-methyl-3-(3-carbomethoxyphenyl)ethynyl-3-(3-cyclopentyloxy-4-methoxyphenyl)propionate (0.14 g, 0.32 mmol) in 5:2 methanol/water was added NaOH (0.01 g, 0.32 mmol). After 24 h, 3N HCl was added, the methanol was evaporated and the aqueous residue was extracted twice with CH$_2$Cl$_2$ and was evaporated. Purification by flash chromatography (silica gel, 5% CH$_3$OH/CHCl$_3$) provided the title compound as a yellow oil (0.02 g, 13%). Anal (C$_{25}$H$_{26}$O$_6$·0.25H20) calcd: C, 70.32; H, 6.26. found: C, 70A6; H, 6.45.

Example 57

Preparation of (+/−)-3-(2-carbomethxyphenyl)ethynyl-3-(3-cyclopentyloxy-4-methoxyphenyl) propionic acid To a solution of (+/−)-methyl-3-(2-carbomethoxyphenyl)ethynyl-3-(3-cyclopentyloxy-4-methoxyphenyl)propionate (0.07 g, 0.16 mmol) in 5:2 methanol/water was added NaOH (0.01 g, 0.32 mmol). After 24 h, 3N HCl was added, the methanol was evaporated and the aqueous residue was extracted twice with CH$_2$Cl$_2$ and was evaporated. Purification by flash chromatography (silica gel, 5% CH$_3$OH/CHCl$_3$) provided the title compound as a yellow oil (0.01 g, 18%).MS(EI) m/e 423 [M+H]$^+$.

Example 58

Preparation of (+/−)-4-Amino-3-(3-cyclopentyloxy-4-methoxyphenyl)-1-phenyl-1-butyne hydrochloride A solution of (+/−)-3-(3-cyclopentyloxy-4-methoxyphenyl)-3-phenylethynylpropionic acid (1.2 g, 3.3 mmol) in Me$_2$CO (40 ml) was cooled to −15° and treated with Et$_3$N (0.505 ml, 3.63 mmol) and then ethyl chloroformate (0.35 ml, 3.63 mmol), at such a rate so the temperature did not exceed −10°. The mixture was stirred at 0° for 15 minutes. A solution of NaN$_3$ (470 mg, 7.25 mmol) in H$_2$O (2 ml) was added dropwise to the cold solution, and stirring continued in the cold for 15 minutes. The reaction was diluted with H$_2$O, and extracted with Et$_2$O. The extracts were washed with H$_2$O, and dried. The ether extract was slowly added to C$_6$H$_5$Me (100 ml) at 110°, and the solution was heated at 110° for 30 minutes, and the solvent was evaporated. The residue was dissolved in a mixture of dioxane (5 ml), H$_2$O (3 ml), and conc. HCl (3 ml), refluxed for 10 minutes, cooled and the solid filtered. Recrystallization from a mixture of i-propanol and Et$_2$O gave the titled compound as the HCl salt, 1.03 g (84%). mp 212–215°. NMR.

Example 59

Preparation of (+/−)-N-[2-(3-Cyclopentyloxy-4-methoxyphenyl)-4-phenylbut-3-ynyl]acetamide A solution of (+/−)-4-amino-3-(3 cyclopentyloxy-4-methoxyphenyl)-1-phenyl-1-butyne (50 mg, 0.15 mmol) and Et$_3$N (0.2 ml) in EtOAc (30 ml) at 5° was treated with Ac$_2$O (0.2 ml). After 5 minutes, the reaction was treated with MeOH, to decompose excess Ac$_2$O. The reaction was washed with H$_2$O and 0.05 N HCl, dried, and the solvent was evaporated. The residue was purified by flash chromatography (alumina, neutral, activity 1, 5% MeOH/CHCl$_3$), and then by recrystallization from a mixture of cyclohexane and Et$_2$O, and gave the titled compound, 37 mg (65%). mp 114–117°. $^1$H NMR (400 MHz, CDCl$_3$) δ 7.42 (m, 2 H), 7.32 (m, 3 H), 6.92 (m, 2 H), 6.84 (d, 1 H), 5.78 (broad s, 1 H), 4.76 (m, lH), 4.02 (t, 1 H), 3.82 (s, 3 H), 3.64 (m, 1 H), 3.50 (m, 1 H), 2.06 (s, 3 H), 1.78–2.00 (m, 6 H), 1.62 (m, 2 H).

Example 60

Preparation of (+/−)-N-[2-(3-Cyclopentyloxy-4-methoxyphenyl)-4-phenylbut-3-ynyl]-trifluoroacetamide A solution of (+/−)-4-amino-3-(3-cyclopentyloxy-4-methoxyphenyl)-1-phenyl-1-butyne hydrochloride (50 mg, 0.14 mmol) and Et$_3$N (40 mg) in a mixture of MeOH (1 ml) and ethyl trifluoroacetate (0.5 ml) was refluxed overnight. The solvents were evaporated, the residue taken up in Et$_2$O, washed with H$_2$O, 0.01N HCl, dried, and the solvent evaporated. The residue was crystallized from a mixture of cyclohexane and Et$_2$O, and gave the titled compound, 32 mg (55%). mp 143–145°. $^1$H NMR (400 MHz, CDCl$_3$) δ 7.42 (m, 2 H), 7.32 (m, 3 H), 6.94 (m, 2 H), 6.84 (d, 1 H), 6.54 (broad s, 1 H), 4.78 (m, 1 H), 4.08 (t, 1 H), 3.82 (s, 3 H), 3.78 (m, 1 H), 3.58 (m, 1 H), 1.76–1.92 (m, 6 H), 1.60 (m, 2 H).

Example 61

Preparation of (+,−)-Methyl 2-(3-cyclopentyloxy-4-methoxyphenyl)-4-phenyl-but-3-ynyloxamate A suspension of (+/−)-4-amino-3-(3-cyclopentyloxy-4-methoxyphenyl)-1-phenyl-1-butyne hydrochloride (400 mg, 1.08 mmol) in CH$_2$Cl$_2$ (20 ml) was treated with Et$_3$N (0.32 ml, 2.3 mmol), and the suspension became a clear solution. The solution was cooled to −20°, and treated dropwise with a solution of methyl oxalyl chloride (146 mg, 1.2 mmol) in CH$_2$Cl$_2$ (2 ml). When the addition was complete, the reaction was diluted with Et$_2$O (100 ml), washed with H$_2$O, 0.1N HCl, aqueous NaHCO$_3$, dried, and the solvent evaporated. The residue was purified by flash chromatography (silica gel, 40% CH$_2$Cl$_2$/Et$_2$O), and gave the titled compound, 390 mg (86%). mp 120–124°. $^1$H NMR (400 MHz, CDCl$_3$) δ 7.44 (m, 3 H), 7.30 (m, 3 H), 6.96 (m, 2 H), 6.82 (d, 1 H), 4.80 (m, IH), 4.08 (t, 1 H), 3.88 (s, 3 H), 3.82 (s, 3 H), 3.76 (m, 1 H), 3.62 (m, 1 H), 1.72–1.96 (m, 6 H), 1.58–1.66 (m, 2 H).

Example 62

Preparation of (+/−)-Methyl 2-(3-cyclopentyloxy-4methoxyphenyl)-4-phenyl-but-3-ynyloxamic acid A solution of (+,−)-methyl 2-(3-cyclopentyloxy-4-methoxyphenyl)-4-phenyl-but-3-ynyloxamate (100 mg, 0.24 mmol) in hot EtOH (3 ml) was treated with 2.5N NaOH (0.5 ml). The reaction was diluted with H$_2$O, acidified with Hcl, and extracted with EtOAc. The extracts were washed with H$_2$O, dried and the solvent evaporated. The residue was recrystallized from MeCN, and gave the titled compound, 42 mg (44%). mp 157–159°. $^1$H NMR (400 MHz, CDCl$_3$+DMSO-D6) δ 7.63 (t, 1 H), 7.45 (m, 2 H), 7.30 (m, 4 H), 6.97 (m, 2 H), 6.85 (d, 1 H), 4.79 (m, 1 H), 4.07 (t, 1 H), 3.84 (s, 3 H), 3.74 (m, 1 H), 3.62 (m, 1 H), 1.78–1.98 (m, 6 H), 1.61 (m, 2 H).

Example 63

Preparation of (+/−)-Methyl 2-(3-cyclopentyloxy-4-methoxyphenyl)-4-phenyl-but-3-ynyloxamide A solution of (+,−)-methyl 2-(3-cyclopentyloxy-4-methoxyphenyl)-4-phenyl-but-3-ynyloxamate (260 mg, 0.62 mmol) in liquid NH$_3$ (5 ml) was stirred overnight in a sealed vial at room temperature. The NH$_3$ was evaporated, and the residue was crystallized from MeOH and gave the titled compound, 180 mg (72%). $^1$H NMR (400 MHz, DMSO-D$_6$) δ 8.75 (t, 1 H), 8.10 (s, 1 H), 7.81 (s, 1 H), 7.42 (m, 2 H), 7.38 (m, 3 H), 6.93 (m, 3 H), 4.76 (m, 1 H), 4.17 (t, 1 H), 3.73 (s, 3 H), 3.53 (m, 1 H), 3.45 (m, 1 H), 1.86 (m, 2 H), 1.72 (m, 4 H), 1.57 (m, 2 H).

Example 64

Preparation of 4-Aninomethylcarbonylamino-3-(3-cyclopentyloxy-4-methoxyphenyl)-1-phenyl-1-butyne cyclohexylsulfamate 64(a) 4-t-Butoxycarbonylaminomethylcarbonylamino-3-(3-cyclopentyloxy-4-methoxyphenyl)-1-phenyl-1-butyne A mixture of (+/−)1amino-3-(3-cyclopentyloxy-4-methoxyphenyl)-1-phenyl-1-butyne hydrochloride (370 mg, 1 mmol), Et$_3$N (101 mg, 1 mmol), N-t-butoxycarbonylglycine (175 mg, 1 mmol), and cyclohexyl morpholinoethylcarbodiimide metho-p-toluene sulfonate (425 mg, 1 mmol) in CH$_2$Cl$_2$ (25 ml) was stirred at 23° for 3 hr. The solvent was evaporated, the residue was taken up in Et$_2$O, washed with H$_2$O, aqueous K$_2$CO$_3$, 0.1N HCl, dried, and the solvent evaporated, and gave the titled compound, 430 mg (87%). $^1$H NMR (400 MHz, CDCl$_3$) δ 7.40 (m, 2 H), 7.30 (m, 3E), 6.94 (m, 2 H), 6.78 (d, 1 H), 6.72 (t, 1 H), 5.38 (t, 1 H), 4.80 (m, 1 H), 4.02 (t, 1 H), 3.78 (s, 3 H), 3.76 (m, 2 H), 3.70 (m, 1 H), 3,48 (m, 1 H), 1.80–1.98 (a, 6 H), 1.60 (m, 2 H), 1.38 (s, 9 H).

64(b) 4-Aminomethylcarbonylamino-3-(3-cyclopentyloxy-4-methoxyphenyl)-1-phenyl-1-butyne cyclohexylsulfamate A solution of 4-t-butoxycarbonylaminomethylcarbonylamino-3-(3- cyclopentyloxy-4methoxyphenyl)-1-phenyl-1-butyne (290 mg, 0.59 mmol) in $CH_2Cl_2$ (5 ml) at 0° was treated with trifluoroacetic acid (4 ml). After 1 hr, all the solvents were evaporated. The residue was partitioned between $H_2O$ and $Et_2O$, basified with aqueous NaOH, and the $Et_2O$ layer seperated, dried, and the solvent evaporated, and gave 4-aminomethylcarbonylamino-3-(3-cyclopentyloxy-4-methoxyphenyl)-1-phenyl-1-butyne, 200 mg (86%). The salt was formed by treating this amine (180 mg) in $Me_2CO$ (2 ml) with sulfamic acid (82 mg). The solution was concentrated to almost dryness, and the resultant crystals were triturated with $Me_2CO$, and gave the titled compound, mp 119–124°. $^1H$ NMR (400 MHz, $CDCl_3$) δ 8.22 (t, 1 H), 7.44 (m, 3 H), 7.28 (m, 3 H), 7.02 (d, 1 H), 6.94 (m, 1 H), 6.82 (d, 1 H), 4.80 (m, 1 H), 4.04 (t, 1 H), 3.80 (s, 3 H), 3.76 (m, 2 H), 3.62 (m, 1 H), 3.52 (m, 1 H), 3.18 (m, 1 H), 2.04 (m, 2 H), 1.80–1.98 (m, 6 H), 1.52–1.72 (m, 4 H), 1.08–1.32 (m, 6 H).

Example 65

Preparation of (+/−)-1-Amino3-(3-cyclopentyloxy-4-methoxyphenyl)-5-phenylpent4-yne 65(a) (+/−)-3-(3-cyclopentyloxy-4methoxyphenyl)-5-phenyl-1-phthaimido-pent-4-yne To a solution of (+/−)-3-(3-cyclopentyloxy-4-methoxyphenyl)-5-phenyl-pent-4-yn-1-ol (0.63 g, 1.78 mmol), phthalimide (0.39 g, 2.67 mmol) and triphenyl phosphine (0.70 g, 2.67 mmol) in tetrahydrofuran (20 mL) at room temperature under an argon atmosphere was dropwise added diethyl azodicarboxylate (0.42 mL, 2.67 mmol). The reaction was stirred for 1 h and was evaporated. Purification by flash chromatography, eluted with 2:8 ethyl acetate: hexanes provided the title compound (0.96 g, 100%) as a pale yellow waxy solid. $^1H$-NMR (400 MHz, $CDCl_3$) δ 7.87 (m, 1 H), 7.79 (m, 2 H), 7.66 (m, 1 H), 7.36 (m, 2 H), 7.26 (m, 3 H), 6.99 (d, J=1.8 Hz, 1 H), 6.95 (dd, J=8.3, 1.8 Hz, 1 H), 6.79 (d, J=8.3 Hz, 1 H), 4.81 (m, 1 H), 3.84.0 (m, 3 H), 3.80 (s, 3 H), 2.25 (m, 2 H), 1.8-2.0 (m, 6 H), 1.65 (m, 2 H) ppm.

65(b) (+/−)-1-amino-3-(3-cyclopentyloxy-4-methoxyphenyl)-5-phenylpent-4-dyne

To a solution of (+/−)-3-(3-cyclopentyloxy-4-methoxyphenyl)-5-phenyl-1-phthalimido-pent-4-yne (0.85 g, 1.78 mmol) in ethanol (20 mL) and tetrahydrofuran (10 mL) at room temperature under an argon atmosphere was added hydrazine monohydrate (0.89 mL, 17.8 mmol) and the reaction was stirred for 18 h. Water was added and the reaction was extracted with three times 10/90 methanol/dichloromethane, was dried ($K_2CO_3$) and was evaporated. Purification by flash chromatography, eluted with 3:97 methanol: dichloromethane provided the title compound (0.36 g, 58%) as a pale yellow oil. $^1H$-NMR (400 MHz, $CDCl_3$) δ 7.42 (m, 2 H), 7.29 (m, 3 H), 6.98 (d, J=2.0 Hz, 1 H), 6.94 (dd, J=8.1, 2.0 Hz, 1 H), 6.83 (d, J=8.1 Hz, 1 H), 4.80 (m, 1 H), 3.92 (t, J=7.3 Hz, 1 H), 3.84 (s, 3 H), 2.93 (m, 2 H), 1.8–2.0 (m, 6 H), 1.67 (m, 2 H), 1.55 (m, 2 H) ppm. Anal ($C_{23}H_{27}NO_2$ 0.25 $H_2O$) calcd: C, 78.04, H, 7.76, N, 3.96; found: C, 78.05, H, 7.37, N, 3.92.

Example 66

Preparation of (+/−)-3-(3-cyclopentyloxy-4-methoxyphenyl)-5-phenyl-1-thiomethyl-pent-4-yne 66(a) (+/−)-3-(3-cyclopentyloxy-4-methoxyphenyl)-1-methylsulfonato 5-phenyl-1-pent4-yne To a solution of (+/−)-3-(3-cyclopentyloxy-4-methoxyphenyl)-5-phenyl-1-pent4yn-1-ol (0.49 g, 1.41 mmol) and triethylamine (0.3 mL, 2.12 mmol) in dichloromethane (10 mL) at 0° C. under an argon atmosphere was dropwise added methanesulfonyl chloride (0.12 mL, 1.55 mmol). Water (2 mL) was added after 0.5 h and stirring was continued at room temperature for 6 h. The reaction was extracted three times with dichloromethane, was dried ($MgSO_4$) and was evaporated. Purification by flash chromatography, eluted with 35:65 ethyl acetate:hexanes provided the title compound (0.42 g, 69%) as a yellow oil. $^1H$-NMR (400 MHz, $CDCl_3$) δ 7.43 (m, 2 H), 7.32 (m, 3 H), 6.96 (m, 2 H), 6.85 (d, J=8.1 Hz, 1 H), 4.70 (m, 1 H), 4.49 (m, 1 H), 4.37 (m, 1 H), 4.01 (dd, J=9.9, 6.0 Hz, 1 H), 3.84 (s, 3 H), 3.04 (s, 3 H), 2.21 (m, 2 H), 1.8–2.0 (m, 6 H), 1.65 (m, 2 H) ppm.

66(b) (+/−)-3-(3cyclopentyloxy-4-methoxyphenyl)-5-phenyl-1-thiomethyl-pent-4-yne To a suspension of sodium thiomethoxide (0.076 g, 1.08 mmol) in ethanol (8 mL) was added a solution of (+/−)-3-(3-cyclopentyloxy-4-methoxyphenyl)-1-methylsulfonato-5-phenyl-pent-4-yne in tetrahydrofuran (4 mL) and the reaction was stirred at room temperature under an argon atmosphere for 24 h. The reaction was diluted with water and sodium bicarbonate, was extracted three times with dichloromethane, was dried ($MgSO_4$) and was evaporated. Purification by two flash chromatographies, eluted first with 1:9 ethyl acetate:hexanes, then with 5:95 ethyl acetate:hexanes provided the title compound (0.23 g, 73%) as a pale yellow oil. $^1H$-NMR (400 MHz, $CDCl_3$) δ 7.43 (m, 2 H), 7.29 (m, 3 H), 6.97 (d, J=1.8 Hz, 1 H), 6.94 (dd, J=8.1, 1.8 Hz, 1 H), 6.84 (d, J=8.1 Hz, 1 H), 4.80 (m, 1 H), 3.98 (t, J=7.2 Hz, 1 H), 3.84 (s, 3 H), 2.66 (m, 2 H), 2.12 (s, 3 H), 2.02 (m, 2 H), 1.8–2.0 (m, 6 H), 1.65 (m, 2 H) ppm. Anal ($C_{24}H_{28}O_2S$·0.125 $H_2O$) calcd: C, 75.30; H, 7.44: found: C, 75.36, H, 7.36.

Example 67

Preparation of (+/−)-3-(3-cyclopentyloxy-4methoxyphenyl)-1-methylsulfoxyl-5-phenyl-pent-4-yne A solution of (+/−)-3-(3-cyclopentyloxy-4-methoxyphenyl)-5-phenyl-1-thiomethyl-pent-4-yne (0.19 g, 0.51 mmol) in methanol (2 mL) and tetrahydrofuran (0.5 mL) was added to a 0° C. solution of sodium metaperiodate (0.12 g, 0.56 mmol) in water (2 mL). After 24 h at room temperature under an argon atmosphere, additional sodium metaperiodate (0.12 g, 0.56 mmol) was added and stirring continued for 3 d. Water was added and the reaction was extracted three times with 5:95 methanol: dichloromethane, was dried ($MgSO_4$) and was evaporated. Purification by two flash chromatographies, eluting with ethyl acetate provided the title compound (0.088 g, 43%) as a yellow oil. $^1H$-NMR (400 MHz, $CDCl_3$) δ 7.43 (m, 2 H), 7.32 (m, 3 H), 6.96 (m, 2 H), 6.84 (d, J=8.2 Hz, 1 H), 4.79 (m, 1 H), 4.01 (m, 1 H), 3.84 (s, 3 H), 2.88 (m, 2 H), 2.57 (s, 3 H), 2.29 (m, 2 H), 1.8–2.0 (m, 6 H), 1.65 (m, 2 H) ppm. Anal ($C_{24}H_{28}O_3S$·0.35 $H_2O$) calcd: C,71.56; H, 7.18; found: C,71.58, H, 6.96.

Example 68

Preparation of (+/−)-3-(3-cyclopentyloxy-4-methoxyphenyl)-1-methylsulfonyl-5-phenyl-pent-4-yne To a solution of (+/−)-3-(3-cyclopentyloxy-4-methoxyphenyl)-5-phenyl-1-thiomethyl-pent-4-yne (0.12 g, 0.31 mmol) in chloroform (10 mL) at 0° C. under an argon atmosphere was added 57–85% 3-chloroperoxybenzoic acid (0.21 g, 0.68 mmol). The reaction was stirred 1 h at 0° C. and 6 h at room temperature. Water and sodium bicarbonate were added and the reaction was extracted three times with dichloromethane, was dried ($MgSO_4$) and was evaporated. Purification by two flash chromatographies, eluting with 3:7 ethyl acetate:hexanes provided the title compound (0.061 g, 48%) as a yellow oil. $^1$H-NMR (400 MHz, $CDCl_3$) δ 7.44 (m, 2 H), 7.33 (m, 3 H), 6.95 (m, 2 H), 6.85 (d, J=8.1 Hz, 1 H), 4.80 (m, 1 H), 3.85 (s, 3 H), 3.19 (m, 2 H), 2.90 (s, 3 H), 2.35 (m, 2 H), 1.8-2.0 (m, 6 H), 1.65 (m, 2 H) ppm. Anal ($C_{24}H_{28}O_4S \cdot 0.25 H_2O$) calcd: C, 69.12; H, 6.89; found: C, 69.02, H, 7.04.

Example 69

Preparation of (+/−)-5,5-bis-methylthio-3-(3-cyclopentyloxy-4-methoxyphenyl)-1-phenyl-1-pentyne 69(a) 3-(3-cyclopentyloxy-4-methoxyphenyl)-3-phenylethynylpropionaldehyde To a solution of oxalyl chloride (0.265 mL, 3.0 mmol) in $CH_2Cl_2$ (11 mL) at −78° C. under an argon atmosphere was added DMSO (0.43 mL, 6.0 mmol). After 0.03 h, (+/−)-3-(3-cyclopentyloxy-4-methoxyphenyl)-5-phenylpent4ynol (0.96 g, 2.74 mmol) was added in $CH_2Cl_2$ (15 mL). After 0.25 h, triethylamine (2.0 mL, 13.7 mmol) was added. The mixture was allowed to warm to room temperature. Aqueous $NH_4Cl$ was added, the mixture was extracted three times with $CH_2Cl_2$, the organic extract was washed with 1N HCl, was dried ($Na_2SO_4$) and was evaporated. Purification by flash chromatography (silica gel, 25% EtOAc/Hex) provided the title compound as a yellow oil (0.59 g, 62%).MS(EI) m/e 349 [M+H]$^+$.

69(b) (+/−)-5,5-bis-methylthio-3-(3-cyclopentyloxy-4-methoxyphenyl)-1-phenyl-1-pentyne To a solution of 3-(3-cyclopentyloxy-4-methoxyphenyl)-3-phenylethynylpropionaldehyde (0.10 g, 0.29 mmol) in $CH_2Cl_2$ (2 mL) at −78° C. under an argon atmosphere was added a saturated solution of methyl mercaptan in $CH_2Cl_2$(2 mL). To the resulting mixture was added boron trifluoride etherate (0.007 mL). The mixture was warmed to room temperature, 10% NaOH (5 mL) was added and the mixture was extracted once with $CH_2Cl_2$. The organic extract was washed once with 10% NaOH, was dried ($Na_2SO_4$) and was evaporated. Purification by flash chromatography provided the title compound as a clear colorless oil (0.09 g, 72%). Anal. ($C_{25}H_{30}S_2O_2$) calcd: C, 70.38; H, 7.09. found: C, 70.07; H, 6.76.

Example 70

Preparation of (+/−)-1-(1,3-dithiolane)-3-(3-cyclopentyloxy-4-methoxyphenyl)-1-phenyl-1-pentyne Following the procedure of Example 69(b) above, except substituting 1,2-dithioethane for methylmercaptan the title compound was prepared as a colorless oil (86%). Anal. ($C_{25}H_{28}S_2O_2$) calcd: C, 70.72; H, 6.65. found: C, 70.68; H, 6.75.

Example 71

Preparation of (+/−)-1-(1,3-Dithiolane)-3-(3-cyclopentyloxy-4-methoxyphenyl)-5-[3-(5-methyl[1,2,4]oxadiazol-3-yl)phenyl]-1-pentyne 71(a) (+/−)-3-(3-cyclopentyloxy-4-methoxyphenyl)pent-4-ynol To a solution of (+/−)-methyl-(3-cyclopentyloxy-4-methoxyphenyl)-3-ethynylpropionate (1.0 g, 3.3 mmol) in THF (20 mL) at 0° C. under an argon atmosphere was added solid lithium aluminum hydride (0.175 g, 4.62 mmol). After 0.3 h, ethyl acetate was added then water was added. The mixture was extracted three times with EtOAc, was dried ($MgSO_4$) and was evaporated to give the title compound as a colorless oil (0.9 g, 100%). $^1$H NMR (400 Mhz, $CDCl_3$) δ 6.89–6.92 (m, 2 H), 6.83 (d, J=8 Hz, 1 H), 4.75 (m, 1 H), 3.75–3.81 (m, 3 H), 3.84 (s, 3 H), 2.31, (d, J=2.5 Hz, 1 H), 1.842.02 (m, 8 H), 1.53–1.69 (m, 4 H).

71 (b) (+/−)-3-(3-cyclopentyloxy-4-methoxyphenyl)pent-4-ynal

To a solution of oxalyl chloride (0.33 mL, 3.85 mmol) in $CH_2Cl_2$ (10 mL) at −78° C. under an argon atmosphere was added DMSO (0.55 mL, 7.7 mmol). After 0.03 h, (+/−)-3-(3-cyclopentyloxy-4-methoxyphenyl)pent-4-ol (0.95 g, 3.5 mmol) was added in $CH_2Cl_2$ (10 mL). After 0.25 h, triethylamine (2.4 mL, 117.5 mmol) was added. The mixture was allowed to warm to room temperature. Aqueous $NH_4Cl$ was added, the mixture was extracted three times with $CH_2Cl_2$, the organic extract was washed with 1N HCl, was dried ($Na_2SO_4$) and was evaporated. Purification by flash chromatography (silica gel, 20% EtOAc/Hex) provided the title compound as a yellow oil (0.77 g, 86%). $^1$H NMR (400 Mhz, $CDCl_3$) δ 9.80 (t, J=1.5 Hz, 1 H), 6.89–6.92 (m, 2 H), 6.82 (d, J=8 Hz, 1 H), 4.78 (m, 1 H), 4.16 (m 1 H), 3.83 (s, 3 H), 2.83–2.91 (m, 2 H), 2.35 (d, J=2.4 Hz, 1 H), 1.842.0 (m, 6 H), 1.57–1.64 (m, 2 H).

71(c) (+/−)-3-(3-cyclopentyloxy-4methoxyphenyl)-5-[3-(5-methyl[1,2,4]oxadiazol-3-yl)phenyl]pent-4-ynal A mixture (+/−)-3-(3-cyclopentyloxy-4-methoxyphenyl) pent-4-ynal (0.20 g, 0.73 mmol) and 1-iodo-3-(5-methyl-[1,2,4]oxadiazol-3-yl)benzene (0.21 g, 0.73 mmol) and trace tetrakistriphenylphosphine palladium (0) and trace copper (I)iodide in triethylamine (5 mL)under an argon atmosphere was heated at 80° C. for 0.25 h. The mixture was cooled to room temperature and was evaporated. The residue was purified by flash chromatography (silica gel, 35% EtOAc/Hex) to provide the title compound as a yellow oil (0.22 g, 71%).$^1$H NMR (250 Mhz, $CDCl_3$) δ 9.86 (t, J=1.7 Hz, 1 H), 8.15, (d, J=1.4 Hz, 1 H), 8.01 (dt, J=7.8 and 1.4 Hz, 1 H), 7.54 (dt, J=7.8 and 1.4 Hz, 1 H), 7.42 (t, J=7.8 Hz),lH), 6.95 (m. 2 H), 6.84 (d, J=8.5 Hz, 1 H), 4.8 (m, 1 H), 4.40 (t, J=7 Hz, 1 H), 3.85 (s, 3 H), 2.86–3.10 (m, 2 H), 2.66 (s, 3 H), 1.80–2.05 (m, 6 H), 1.60–1.69 (m, 2 H).

71(d) (+1-)- 1-(1,3-dithiolane)-3-(3-cyclopentyloxy-4-methoxyphenyl)-5-[3-(5-methyl[1,2,4]oxadiazol-3-yl) phenyl]-1-pentyne Following the procedure of Example 69(b) above, except substituting (+/−)-3-(3-cyclopentyloxy-4-methoxyphenyl)-5-[3-(5-methyl[1,2,4]oxadiazol-3-yl)phenyl]pent-4-ynal for 3-(3-cyclopentyloxy-4-methoxyphenyl)-3-phenylethynylpropionaldehyde, the title compound was prepared as a yellow oil (71%). Anal. ($C_{28}H_{30}N_2S_2O_3 \cdot 0.5H_2O$) calcd: C, 65.52; H, 6.06; N, 5.43. found: C, 65.52; H, 5.92; N, 5.03.

Example 72

Preparation of (+/−)-2-[2-(3-Cyclopentyloxy-4-methoxyphenyl)-4-phenylbut-3-ynyl]-5-methylthiazole 72(a) (+/−)-3-(3-cyclopentyloxy-4-methoxyphenyl)-3-phenylethynylpropionic acid thioamide A solution of (+/−)-3-(3-cyclopentyloxy-4-methoxyphenyl)-3-phenylethynylpropionic acid amide (1.5 gm, 4.13 mmol) in benzene (75 ml) was treated with Lawesson's reagent (835 mmol, 2.07 mmol) and heated at 65° for 40 min. The solvent was evaporated, the residue was taken up in a mixture of EtOAc and Et$_2$O, washed twice with 5% aq K$_2$CO$_3$, dried, and the solvent evaporated. Purification by flash chromatography (silica gel 10% Et$_2$O in CH$_2$Cl$_2$) gave the titled compound as a pale yellow oil (1.04 gm, 67%). $^1$H NM (400MHz, CDCl$_3$) δ 7.58 (s, broad, 1 H), 7.42 (m, 2 H), 7.30 (m, 3 H),7.08 (s, broad, 1 H), 7.00 (m, 2 H), 6.82 (d, 1 H), 4.78 (m, 1 H), 4.46 (t, 1 H), 3.82 (s, 3 H), 3.12 (dd, 1 H), 3.08 (dd, 1 H), 1.78–1.98 (m, 6 H), 1.60 (m, 2 H).

72(b) (+/−)-2-[2-(3-Cyclopentyloxy-4-methoxyphenyl)4-phenylbut-3-ynyl]-4-hydroxy-5-methyl-4,5-dihydrothiazole A mixture of (+/−)-3-(3-cyclopentyloxy-4-methoxyphenyl)-3-phenylethynylpropionic acid thioamide (500 mg, 1.65 mmol), α-bromopropionaldehyde (350 mg) and K$_2$CO$_3$ (800 mg) in EtOH (20 ml) was heated at 60° for 3 hr. The solvent was thoroughly evaporated, the residue taken up in Et$_2$O, washed with H$_2$O, dried, and the solvent evaporated. Purification by flash chromatography (silica gel, 50% Et$_2$O in CH$_2$Cl$_2$) gave the titled product (90 mg, 15%), MS(EI) m/e 423 [M+H]$^+$.

72(c) (+/−)-2-[2-(3-Cyclopentyloxy-4-methoxyphenyl)-4-phenylbut-3-ynyl]-5-methylthiazole A solution of (+/−)-2-[2-(3-cyclopentyloxy-4-methoxyphenyl)-4-phenylbut-3-ynyl]-4-hydroxy-5-methyl-4,5-dihydrothiazole (70 mg, 0.2 mmol) in CDCl$_3$ (4 ml) was treated with HCl (0.2 ml of a 1N solution in Et$_2$O) and heated to 50° for 3 hr. The solvent was evaporated, the residue taken up in Et$_2$O, washed with aqueous NaHCO$_3$, H$_2$O, dried and the solvent evaporated. Purification by flash chromatography (silica gel, 2% Et$_2$O in CH$_2$Cl$_2$) gave the titled compound (19 mg, 28%). $^1$H NMR (400 MHz, CDCl$_3$) δ 7.42 (m, 2 H), 7.36 (s, 1 H), 7.30 (m, 3 H), 7.00 (m, 1 H), 6.92 (d, 1 H), 6.84 (d, 1 H), 4.74 (m, 1 H), 4.28 (t, 1 H), 3.82 (s, 3 H), 3.40 (d, 2 H), 2.42 (s, 3 H), 1.78–1.98 (m, 6 H), 1.60 (m, 2 H).

Example 73

Preparation of (+/−)-2-[2-(3-Cyclopentyloxy-4-methoxyphenyl)-4-phenylbut-3-ynyl]-4-methylthiazole A solution of (+/−)-3-(3-cyclopentyloxy-4-methoxyphenyl)-3-phenylethynylpropionic acid thioamide (114 mg, 0.3 mmol) and chloroacetone (0.2 ml) in EtOH (3 ml) was heated at 60° for 2 hr. The solvent was evaporated, the residue taken up in Et$_2$O, washed with aqueous NaHCO$_3$, H$_2$O, dried and evaporated. The residue was purified by flash chromatography (1. silica gel, 10:10:3/hexane:CH$_2$Cl$_2$:Et$_2$O, 2. alumina, neutral, Act.I, 10:10:1/hexane:CH$_2$Cl$_2$:Et$_2$O), and gave the itled compound (43 mg, 34%). $^1$H NMR (400 MHz, CDCl$_3$) δ 7.40 (m, 2 H), 7.30 (m, 3 H), 7.00 (m, 1 H), 6.96 (d, 1 H), 6.82 (d, 1 H), 6.76 (s, 1 H), 4.76 (m, 1 H), 4.28 (t, 1 H), 3.84 (s, 3 H), 3.44 (m, 2 H), 2.46 (s, 3 H), 1.78–1.98 (m, 6 H), 1.60 (m, 2 H).

Example 74

Preparation of (+/−)-3-(3-cyclopentyloxy-4-methoxyphenyl)4(5-ethyloxazol-2-yl)-1-phenylbut-1-yne 74(a) (+/−)-3-(3-cyclopentyloxy-4-methoxyphenyl)-4-[N-butan-2-ol)-carboxamido]-1-phenylbut-1-yne To a solution of (+/−)-3-(3-cyclopentyloxy-4-methoxyphenyl)-3-phenylethynylpropionic acid (0.50 g, 1.37 mmol) and dimethyl formamide (3 drops) in dichloromethane (10 mL) at room temperature under an argon atmosphere was dropwise added oxalyl chloride (0.125 mL, 1.44 mmol). The reaction was stirred 0.5 h, was evaporated, was dissolved in tetrahydrofuran (5 mL) and was added to a solution of 1-amino-2-butanol (0.15 mL, 1.52 mmol) and triethylamine (0.23 mL, 1.64 mmol) in tetrahydrofuran (10 mL) and was stirred at room temperature under an argon atmosphere for 1 h. Water was added, the reaction was extracted with three times dichloromethane, was dried (MgSO$_4$) and was evaporated. Purification by flash chromatography, eluted with 2:98 methanol:dichloromethane provided the title compound (0.54 g, 91%) as a white solid, mp.94–96° C.

74(b) (+/−)-3-(3-cyclopentyloxy-4-methoxyphenyl)-4-[(N-butan-2-one)-carboxamido]-1-phenylbut-1-yne To a solution of oxalyl chloride ( 0.1 mL, 1.23 mmol) in dichloromethane (5 mL) at −78° C. under an argon atmosphere was dropwise added first a solution of dimethyl sulfoxide (0.19 mL, 2.68 mmol) in dichloromethane (4 mL) followed by a solution of (+/−)-3-(3-cyclopentyloxy-4-methoxyphenyl)-4-[(N-butan-2-ol)-carboxamido]-1-phenylbut-1-yne (0.49 g, 1.12 mmol) in dichloromethane (4 mL). After 0.5 h, triethylamine (0.75 mL, 5.36 mmol) was dropwise added and the reaction was stirred at room temperature for 1 h. Water was added, the reaction was extracted with three times dichloromethane, was dried (MgSO$_4$) and was evaporated. Purification by flash chromatography, eluted with 1:1 ethyl acetate:hexanes provided the title compound (0.43 g, 88%) as a white solid, mp.107–109° C.

74(c) (+/−)-3-(3-cyclopentyloxy-4-methoxyphenyl)4(5-ethyloxazol-2-yl)-1-phenylbut-1-yne To a solution of (+/−)-3-(3-cyclopentyloxy-4-methoxyphenyl)-4-[(N-butan-2-one)-carboxamido]-1-phenylbut-1-yne (0.51 g, 1.18 mmol), N,N-dimethylaminopyridine (0.015 g, 10%) and pyridine (2.38 mL, 29.5 mmol) in dichloromethane (15 mL) at 0° C. under an argon atmosphere was dropwise added over 15 min trichloroacetyl chloride (1.35 mL, 11.8 mmol). After 1 h the reaction was neutralized with sodium bicarbonate, was diluted with water, was extracted with three times dichloromethane, was dried (NaHCO$_3$) and was evaporated. The residue was dissolved in methanol (10 mL) at 0° C. under an argon atmosphere and was stirred with potassium carbonate (0.50 g, 3.54 mmol) for 1 h. The reaction was diluted with water, was extracted three times with dichloromethane, was dried (MgSO$_4$) and was evaporated. Purification by two flash chromatographies, eluted first with 2:8 ethyl acetate: hexanes, then with 15:85 ethyl acetate-:hexanes provided the title compound (0.15 g, 31%) as a dark oil. $^1$H-NMR (400 MHz, CDCl$_3$) δ 7.39 (m, 2 H), 7.29 (m, 3 H), 6.93 (m, 2 H), 6.83 (d, J=8.3 Hz, 1 H), 6.64 (s, 1 H), 4.75 (m, 1 H), 4.34 (t, J=7.2 Hz, 1 H), 3.83 (s, 3 H), 3.22 (d AB quartets, Δppm=0.10, J=14.6, 8.5 Hz, 2 H), 2.62 (q, J=7.5 Hz, 2 H), 1.8–2.0 (m, 6 H), 1.65 (m, 2 H), 1.21 (t, J=7.5 Hz, 3 H) ppm. Anal (C$_{27}$H$_{29}$NO$_3$ ·0.25 H$_2$O) calcd:C,77.21, H, 7.08, N, 3.33; found: C, 77.06, H, 7.09, N, 3.37.

Example 75

Preparation of (+/−)-3-(3-cyclopentyloxy-4-methoxyphenyl)-4-(5-methyloxazol-2-yl)-1-phenylbut-1-yne 75(a) (+/−)-3-(3-cyclopentyloxy-4-methoxyphenyl)-4-[(N-propan-2-ol)-carboxamido]-1-phenylbut-1-yne Following the procedure for Example 74(a), except substituting 1-amino-2-propanol for 1-amino-2-butanol the title compound was prepared (83%) as a pale yellow solid, mp 103–104° C.

75(b) (+/−)-3-(3-cyclopentyloxy-4-methoxyphenyl)-4-[(N-propan-2-one)-carboxamido]-1-phenylbut-1-yne To a suspension of pyridinium dichromate (0.38 g, 1.0 mmol) and acetic anhydride (0.4 mL, 4.2 mmol) in dichloromethane (15 mL) was rapidly added a solution of (+/−)-3-(3-cyclopentyloxy-4-methoxyphenyl)-4-[(N-propan-2-ol)-carboxamido]-1-phenylbut-1-yne (0.59 g, 1.4 mmol) in dichloromethane (5 mL) and the reaction was refluxed under an argon atmosphere for 7 h, then at room temperature for 3 d. The reaction was diluted with ether (30 mL), was filtered through Celite and was evaporated. Purification by flash chromatography, eluted with 1:1 ethyl acetate:hexanes provided the title compound (0.38 g, 64%) as a pale yellow solid, mp 105–106° C.

75(c) (+/−)-3-(3-cyclopentyloxy-4-methoxyphenyl)-4-(5-methyloxazol-2-yl-1-phenylbut-1-yne Following the procedure for Example 74(c), except substituting (+/−)-3-(3-cyclopentyloxy-4-methoxyphenyl)-4-[(N-propan-2-one)-carboxamido]-1-phenylbut-1-yne for (+/−)-3-(3-cyclopentyloxy-4-methoxyphenyl)-4-[(N-butan-2-one)-carboxamido]-1-phenylbut-1-yne the title compound was prepared (33%) as a yellow oil. $^1$H-NMR (400 MHz, CDCl$_3$) δ 7.38 (m, 2 H), 7.28 (m, 3 H), 6.94 (m, 2 H), 6.82 (d, J=8.2 Hz, 1 H), 6.64 (s, 1 H), 4.75 (m, 1 H), 4.34 (t, J=7.8 Hz, 1 H), 3.83 (s, 3 H), 3.21 (d AB quartets, Δppm=0.08, J=14.6, 8.5 Hz, 2 H), 2.26 (d, J=1.0Hz, 3 H), 1.8–2.0 (m, 6 H), 1.65 (m, 2 H) ppm. Anal (C$_{26}$H$_{27}$NO$_3$·0.5 H$_2$O) calcd: C, 76.07, H, 6.87, N, 3.40, found: C, 75.76, H, 6.80, N, 3.24.

Example 76

Preparation of (+/−)-3-(3-cyclopentyloxy-4-methoxyphenyl)-4-(4,5-dimethyloxazol-2-yl)-1-phenylbut-1-yne 76(a) (+/−)-3-(3-cyclopentyloxy-4-methoxyphenyl)-4-[(N-butan-2-ol-3-yl)-carboxamidol-1-phenylbut-1-yne Following the procedure for Example 74(a), except substituting 3-amino2-butanol for 1-amino-2-butanol the title compound was prepared (16%) as a colorless oil. $^1$H-NMR (400 MHz, CDCl$_3$) δ 7.44 (m, 2 H), 7.30 (m, 3 H), 6.99 (m, 2 H), 6.83 (d, J=7.5 Hz, 1 H), 5.81 (m, 1 H), 4.79 (m, 1 H), 4.34 (m, 1 H), 3.85 (m, 2 H), 3.83 (s, 3 H), 2.60 (m, 2 H), 1.8-2.0 (m, 6 H), 1.65 (m, 2 H), 1.05 (m, 6 H) ppm.

76(b) (+/−)-3-(3-cyclopentyloxy-4-methoxyphenyl)-4-[(N-butan-2-on-1-yl)-carboxamido]-1-phenylbut-1-yne Following the procedure for Example 75(b), except substituting (+/−)3-(3-cyclopentyloxy-1methoxyphenyl)-4-[(N-butan-2-ol-3-yl)-carboxamidol-1-phenylbut-1-yne for (+/−)-3-(3-cyclopentyloxy-4-methoxyphenyl)4[(N-propan-2-ol)-carboxamido]-1-phenylbut-1-yne the title compound was prepared (73%) as a colorless oil. $^1$H-NMR (400 MHz, CDCl$_3$) δ 7.42 (m, 2 H), 7.29 (m, 3 H), 6.99 (m, 1 H), 6.84 (m, 1 H), 6.43 (d, J=7.2 Hz, 1 H), 4.79 (m, 1 H), 4.58 (m, 1H), 4.33 (t, J=7.4 Hz, 1 H), 3.83 (s, 3 H), 2.71 (m, 2 H), 2.19 (s, 3 H), 1.8-2.0 (m, 6 H), 1.65 (m, 2 H), 1.27 (d, J=7.2 Hz, 3 H) ppm.

76(c) (+/−)-3-(3-cyclopentyloxy-4-methoxyphenyl)-4-(4,5-dimethyl oxazol-2-yl)-1-phenylbut-1-yne Following the procedure for Example 74(c), except substituting (+/−)-3-(3-cyclopentyloxy-4-methoxyphenyl)-4-[(N-butan-2-on-1-yl)-carboxamido]-1-phenylbut-1-yne for (+/−)-3-(3-cyclopentyloxy-4-methoxyphenyl)4[(N-butan-2-one)-carboxamido]-1-phenylbut-1-yne the title compound was prepared (38%) as a yellow oil. $^1$H-NMR (400 MHz, CDCl$_3$) δ 7.38 (m, 2 H), 7.28 (m, 3 H), 6.97 (dd, J=8.3, 2.0 Hz, 1 H), 6.92 (d, J=2.0 Hz, 1 H), 6.83 (d, J=8.3 Hz, 1 H), 4.74 (m, 1 H), 4.32 (t, J=7.7 Hz, 1 H), 3.83 (s, 3 H), 3.70 (d AB quartets, Δppm=0.07, J=14.6, 8.8 Hz, 2 H), 2.19 (s, 3 H), 2.06 (s, 3 H), 1.8–2.0 (m, 6 H), 1.65 (m, 2 H) ppm. Anal (C$_{27}$H$_{29}$NO$_3$·1.0 H$_2$O) calcd: C, 74.80, H, 7.20, N, 3.23, found: C, 74.45, H, 6.68, N, 3.10.

Example 77

Preparation of (+/−)-3-(3-cyclopentyloxy-4-methoxyphenyl)-4-(4-ethyloxazol-2-yl)-1-phenylbut-1-yne 77(a) (+/−)-3-(3-cyclopentyloxy-4-methoxyphenyl)-4-[(N-butan-1-ol-2-yl)-carboxamidol-1-phenylbut-1-yne Following the procedure for Example 74(a), except substituting 2-amino-1-butanol for 1-amino-2-butanol the title compound was prepared (98%) as a waxy white solid, mp 58–59° C.

77(b) (+/−)-3-(3-cyclopentyloxy-4-methoxyphenyl)-4-[(N-butan-1-al-2-yl)-carboxamidol-1-phenylbut-1-yne Following the procedure for Example 74(b), except substituting (+/−)3-(3-cyclopentyloxy-4-methoxyphenyl)-4-[(N-butan-1-ol-2-yl)-carboxamido]-1-phenylbut-1-yne for (+/−)-3-(3-cyclopentyloxy-4-methoxyphenyl)4[(N-butan-2-ol)-carboxamido]-1-phenylbut-1-yne, the title compound was prepared (76%) as a colorless oil. $^1$H-NMR (400 MHz, CDCl$_3$) δ 9.54 (s, 1/2 H), 9.51 (s, 1/2 H), 7.41 (m, 2 H), 7.30 (m, 3 H), 7.00 (m, 2 H), 6.85 (m, 1H), 6.35 (m, 1 H), 4.79 (m, 1 H), 4.54 (m, 1 H), 4.35 (m, 1H), 3.83 (s, 3 H), 2.70 (m, 2 H), 1.8–2.0 (m, 6 H), 1.65 (m, 2 H), 0.90 (m, 3 H) ppm.

77(c) (+/−)-3-(3-cyclopentyloxy-4-methoxyphenyl)-4-(4-ethyloxazol-2-yl)-1-phenylbut-1-yne To a solution of triphenylphosphine (0.44 g, 1.65 mmol), iodine (0.38 g, 1.5 mmol) and triethylamine (0.42 mL, 3.0 mmol) in dichloromethane (3 mL) at 0° C. under an argon atmosphere in a foil-wrapped flask was added a solution of (+/−)-3-(3-cyclopentyloxy-4-methoxyphenyl)-4-[(N-butan-1-al-2-yl) arboxamido]-1-phenylbut-1-yne (0.33 g, 0.75 mmol) in dichloromethane (3 mL) and the reaction was stirred for 20 h. Water and sodium bisulfite were added and the reaction was extracted three times with dichloromethane, was dried (MgSO$_4$), and was evaporated. This was combined with crude product from another run and was purified by flash chromatography, eluted with 1:9 ethyl acetate:hexanes to provide the title compound (0.21 g, 37%) as a yellow oil. $^1$H-NMR (400 MHz, CDCl$_3$) δ 7.39 (m, 2 H), 7.29 (m, 3 H), 6.96 (dd, J=8, 2 Hz, 1 H), 6.91 (d, J=2 Hz, 1 H), 6.83 (d, J=8 Hz, 1 H), 4.74 (m, 1 H), 4.35 (t, J=7.8 Hz, 1 H), 3.83 (s, 3 H), 3.24 (d AB quartets, Δppm=0.l0, J=14.5, 8.5 Hz, 2 H), 2.54 (q, J=7.5 Hz, 2 H), 1.8-2.0 (m, 6 H), 1.65 (m, 2 H), 1.21 (t, J=7.5 Hz, 3 H) ppm. Anal (C$_{27}$H$_{29}$NO$_3$·0.7 H$_2$O) calcd: C,75.74, H, 7.16, N, 3.27; C, 75.78, H, 6.83, N, 3.13.

Example 78

Preparation of (+/−)-3-(3-cyclopentyloxy-4-methoxyphenyl)-4-(4-methyloxazol-2-yl)-1-phenylbut-1-yne 78(a) (+/−)-3-(3-cyclopentyloxy-4-methoxyphenyl)-4-[(N-propan-1-ol-2-yl)-carboxamido]-1-phenylbut-1-yne Following the procedure for Example 74(a), except substituting 2-amino-1-propanol for 1-amino-2-butanol the title compound was prepared (58%) as a white solid, mp 56–57° C.

78(b) (+/−)-3-(3-cyclopentyloxy-4-methoxyphenyl)-4-[(N-propan-1-al-2-yl)-carboxamido]-1-phenylbut-1-yne Following the procedure for Example 74(b), except substituting (+/−)-3-(3-cyclopentyloxy-4-methoxyphenyl)-4-[(N-propan-1-ol-2-yl)-carboxarnidol-1-phenylbut-1-yne for (+/−)-3-(3-cyclopentyloxy-4-methoxyphenyl)-4-[(N-butan-2-ol)-carboxamido]-1-phenylbut-1-yne, the title compound was prepared (65%) as a white wax. $^1$H-NMR (400 MHz, CDCl$_3$) δ 9.52 (s, 1/2 H), 9.48 (s, 1/2 H), 7.43 (m, 2 H), 7.31 (m, 3 H), 6.99 (m, 2 H), 6.83 (d, J=7.9 Hz, 1 H), 6.83 (d, J=7 Hz, 1/2 H), 6.77 (d, J=7 Hz, 1/2 H), 4.79 (m, 1 H), 4.50 (m, 1 H), 4.35 (t, J=7.4 Hz, 1 H), 3.83 (s, 3 H), 2.71 (m, 2 H), 1.8–2.0 (m, 6 H), 1.65 (m, 2 H), 1.35 (d, J=7.4 Hz, 1 1/2 H), 1.28 (d, J=7.4 Hz, 1 1/2 H) ppm.

78(c) (+/−)-3-(3-cyclopentyloxy-4-methoxyphenyl)-4-(4-methyloxazol-2-yl)-1-phenylbut-1-yne Following the procedure for Example 77(c), except substituting (+/−)-3-(3-cyclopentyloxy-4-methoxyphenyl)-4-[(N-propan-1-al-2-yl)-carboxamido]-1-phenylbut-1-yne for (+/−)-3-(3-cyclopentyloxy-4methoxyphenyl)4[N-butan-1-al-2-yl)-carboxamido]-1-phenylbut-1-yne, the title compound was prepared (39%) as a yellow oil. $^1$H-NMR (400 MHz, CDCl$_3$) δ 7.39 (m, 2 H), 7.29 (m, 3 H), 6.97 (dd, J=8.3,2.0 Hz, 1 H), 6.93 (d, J=2.0 Hz, 1 H), 6.82 (d, J=8.3 Hz, 1 H), 4.75 (m, 1 H), 4.37 (t, J=7.7 Hz, 1 H), 3.83 (s, 3 H), 3.25 (d AB quartets, Δppm=0.08, J=14.5, 8.5 Hz, 2 H), 2.16 (d, J=1.0 Hz, 3 H), 1.8-2.0 (m, 6 H), 1.65 (m, 2 H) ppm. Anal (C$_{26}$H$_{27}$NO$_3$·0.9 H$_2$O) calcd: C, 74.76, H, 6.95, N, 3.35; C, 74.57, H, 6.51, N, 3.16.

Example 79

Preparation of (+/−)-3-(3-cyclopentyloxy-4-methoxyphenyl)-4-(4-trifluoroethyloxazol-2-yl)-1-phenylbut-1-yne 79(a) (+/−)-3-(3-cyclopentyloxy-4-methoxyphenyl)-4-[N-(methyl 4,4,4-trifluorobutanoat-2-yl)carboxamido]-1-phenylbut-1-yne Following the procedure for Example 74(a), except substituting methyl 2-amino4,4,4trifluorobutyrate for 1-amino-2-butanol the title compound was prepared (93%) as an off-white solid, mp 133–134° C.

79(b) (+/−)-3-(3-cyclopentyloxy-4-methoxyphenyl)-4-[(N4,4,4-trifluorobutan-1-ol-2-yl)-carboxamido]-1-phenylbut-1-yne To a solution of (+/−)-3-(3-cyclopentyloxy-4-methoxyphenyl)-4-[N-(methyl 4,4,4trifiuorobutanoat-2-yl)] carboxamido-1-phenylbut-1-yne (0.55 g, 1.06 mmol) in dimethoxyethane (10 mL) at room temperature under an argon atmosphere was added lithium borohydride (0.047 g, 2.13 mmol) and the reaction was stirred for 1.5 h. The reaction was cooled to 0° C., was carefully quenched with ammonium chloride and water, was extracted three times with 5/95 methanol/dichloromethane, was dried (MgSO$_4$), and was evaporated. Purification by flash chromatography, eluted with 1:1 ethyl acetate:hexanes provided the title compound (0.46 g, 89%), a mixture of isomers, as a white solid, mp 132–133° C.

79(c) (+/−)-3-(3-cyclopentyloxy-4-methoxyphenyl)-4-[(N-4,4,4-trifluorobutan-1-al-2-yl)-carboxamidol-1-phenylbut-1-yne Following the procedure for Example 74(b), except substituting (+/−)-3-(3-cyclopentyloxy-4-methoxyphenyl)-4-[(N-4,4,4-trifluorobutan- 1-o-2-yl)-carboxamido]-1-phenylbut-1-yne for (+/−)-3-(3-cyclopentyloxy-4-methoxyphenyl)-4-[(N-butan-2-ol)-carboxamido]-1-phenylbut-1-yne, the title compound was prepared as a crude mixture (0.46 g, 100%). $^1$H-NMR (400 MHz, CDCl$_3$) δ 9.48 (s, 1/2 H), 9.42 (s, 1/2 H), 7.42 (m, 2 H), 7.35 (m, 3 H), 7.00 (m, 2 H), 6.75 (d, J=8 Hz, 1 H), 6.45, (m, 1 H), 4.70 (m, 1 H), 4.42 (m, 1 H), 3.85 (s, 3 H), 3.50 (s, 2 H), 2.80 (m, 2 H), 1.8–2.0 (m, 6 H), 1.65 (m, 2 H) ppm.

79(d) (+/−)-3-(3-cyclopentyloxy-4-methoxyphenyl)-4-(4-trifluoroethyloxazol-2-yl)-1-phenylbut-1-yne Following the procedure for Example 77(c), except substituting (+/−)-3-(3-cyclopentyloxy-4-methoxyphenyl)-4-[(N-4,4,4-trifluorobutan- 1-al-2-yl)-carboxamido]-1-phenylbut-1-yne for (+/−)-3-(3-cyclopentyloxy-4-methoxyphenyl)-4-[-(N-butan-1-al-2-yl)-carboxamido]-1-phenylbut-1-yne, the title compound was prepared (2%) as a yellow oil. $^1$H-NMR (400 MHz, CDCl$_3$) δ 7.54 (s, 1 H), 7.38 (m, 2 H), 7.29 (m, 3 H), 6.94 (m, 2 H), 6.82 (d, J=8.9 Hz, I H), 4.75 (m, 1 H), 4.35 (m, 1 H), 3.83 (s, 3 H), 3.32 (m, 4 H), 1.8–2.0 (m, 6 H), 1.65 (m, 2 H) ppm. Anal (C$_{27}$H$_{26}$F$_3$NO$_3$) calcd: C, 69.07, H, 5.58, N, 2.98; C, 69.19, H, 5.90, N, 3.12.

Example 80

Preparation of (S)-3-(3-cyclopentyloxy-4-methoxyphenyl)4-methyloxazol-2-yl)-1-(5-methyl-[1,2,4]oxadiazol-3-ylphenyl)but-1-yne 80(a) S-3-(3-cyclopentyloxy-4-methoxyphenyl)-3-[3-(5-methyl[1,2,4]oxadiazol-3-yl)phenylethynyl]propionic acid A mixture of (R)-methyl-3-(3-cyclopentyloxy-4-methoxyphenyl)-3-ethynylpropionate (1.055 g, 2.29 mmol) and potassium hydroxide (0.14 g, 2.41 mmol) in tetrahydrofuran(10 mL), methanol (10 mL) and water (4 mL) was stirred at room temperature for 3.5 h. Preliminary workup showed incomplete saponification, so the crude mixture was resubjected to the same reaction conditions, using only 0.08 g (0.63 mmol) potassium hydroxide. After 8 h, the reaction was neutralized with 10% hydrochloric acid, was extracted three times with 5/95 methanol/ldichloromethane, was dried (MgSO$_4$) and was evaporated to provide the crude tide compound (0.92 g, 90%) as an orange foam.

80(b) S-3-(3-cyclopentyloxy-4-methoxyphenyl)-4-[(N-propan-1-ol-2-yl)-carboxamido]-1-(5-methyl-[1,2,4]oxadiazoI-3-ylphenyl)but- 1-yne Following the procedure for Example 74(a), except substituting 2-amino-1-propanol for 1-amino-2-butanol and substituting S-3-(3-cyclopentyloxy-4-methoxyphenyl)-3-[3-(5-methyl[1,2,4]oxadiazol-3-yl)phenylethynyl]propionic acid for (+/−)-3-(3-cyclopentyloxy-4methoxyphenyl)-3-phenylethynylpropionic acid the title compound was prepared (58%) as an ivory solid, mp 131–132° C.

80(c) S-3-(3-cyclopentyloxy-4methoxyphenyl)-4-[(N-propan-1-al-2-yl)-carboxamido]-1-(5-methyl[1,2,4]oxadiazol-3-ylphenyl)but-1- yne Following the procedure for Example 74(b), except substituting S-3-(3-cyclopentyloxy-4-methoxyphenyl)4[(N-propan-1-ol-2-yl)-carboxamido]-1-(5-methyl[1,2,4]oxadiazol-3-ylphenyl)but-1-yne for (+/−)-3-(3-cyclopentyloxy-4-methoxyphenyl)4[(N-butan-2-ol)-carboxamido]-1-phenylbut-1-yne, the ttle compound was prepared (87%) as a dark red oil. ¹H-NMR (400 MHz, CDCl₃) δ 9.52 (s, 1/2 H), 9.47 (s, 1/2 H), 8.13 (s, 1 H), 7.98 (d, J=7.8 Hz, 1 H), 7.52 (m, 1 H), 7.41 (t, J=7.8 Hz, 1 H), 6.97 (m, 2 H), 6.61 (d, J=8.2 Hz, 1 H), 6.35 (br, 1/2 H), 6.31 (br, 1/2 H), 4.79 (m, 1 H), 4.50 (m, 1 H), 4.36 (m, 1 H), 3.83 (s, 3 H), 2.75 (m, 2 H), 2.66 (s, 3 H), 1.8–2.0 (m, 6 H), 1.65 (m, 2 H), 1.34 (d, J=7.4 Hz, 1 1/2 H), 1.27 (d, J=7.4 Hz, 1 1/2 H) ppm.

80(d) S-3-(3-cyclopentyloxy-4-methoxyphenyl)4(4-methyloxazol-2-yl)-1-(5-methyl [1,2,4]oxadiazol-3-ylphenyl)but- 1-yne Following the procedure for Example 77(c), except substituting S-3-(3-cyclopentyloxy-4-methoxyphenyl)4-[(N-propan-1-al-2-yl)-carboxamido]-1-(5-methyl[1,2,4]oxadiazol-3-ylphenyl)but-1-yne for (+/−)-3-(3-cyclopentyloxy-4-methoxyphenyl)-4-[(N-butan-1-al-2-yl)-carboxamido]- 1-phenylbut- 1-yne, the title compound was prepared (33%) as a yellow oil. ¹H-NMR (400 MHz, CDCl₃) δ 8.11 (s, 1 H), 7.98 (d, J=7.8 Hz, 1 H), 7.50 (d, J=7.8 Hz, 1 H), 7.40 (t, J=7.8 Hz, 1 H), 7.30 (s, 1 H), 6.97 (dd, J=8.3, 2.0 Hz, 1 H), 6.92 (d, J=2.0 Hz, 1 H), 6.84 (d, J=8.3 Hz, 1 H), 4.76 (m, 1 H), 4.36 (t, J=7.7 Hz, 1 H), 3.84 (s, 3 H), 3.24 (d AB quartets, Δppm=0.08, J=14.6, 8.6 Hz, 2 H), 2.65 (s, 3 H), 2.17 (s, 3 H), 1.8–2.0 (m, 6 H), 1.65 (m, 2 H) ppm. Anal (C₂₉H₂₉N₃O₄·1.1 H₂O) calcd: C, 69.19, H, 6.00, N, 8.35; C, 69.32, H, 5.62, N, 8.38.

Example 81

Preparation of (S)-3-(3-cyclopentyloxy-4-methoxyphenyl)-4-(4-methyloxazol-2-yl)-1-(3-methyl-[1,2,4]oxadiazol-5-ylphenyl)but-1-yne 81(a) S-3-(3-cyclopentyloxy-4-methoxyphenyl)-4-[(N-propan-1-ol-2-yl)-carboxamido]-1-but-1-yne Following the procedure for Example 74(a), except substituting 2-amino-1-propanol for 1-amino-2-butanol and substituting (S)-3-(3-cyclopentyloxy-4-methoxyphenyl)-3-ethynyl propionic acid for (+/−)-3-(3-cyclopentyloxy-4-methoxyphenyl)-3-phenylethynylpropionic acid, the crude title compound was prepared (100%) as a colorless oil. ¹H-NMR (250 MHz, CDCl₃) δ 6.88 (m, 2 H), 6.80 (m, 1 H), 5.71 (br, 1 H), 4.77 (m, 1 H), 4.12 (m, 1 H), 4.00 (m, 1 H), 3.81 (s, 3 H), 2.90 (dd, J=12,5 Hz, 1 H), 2.58 (m 2 H), 2.31 (d, J=1.9 Hz, 1 H), 1.8-2.0 (m, 6 H), 1.65 (m, 2 H), 1.14 (d, J=6.8 Hz, 3 H) ppm.

81(b) S-3-(3-cyclopentyloxy-4-methoxyphenyl)-4-[(N-propan-1-al-2-yl)-carboxamido]-1-but-1-yne Following the procedure for Example 74(b), except substituting S-3-(3-cyclopentyloxy-4-methoxyphenyl)-4-[(N-propan-1-ol-2-yl)-carboxamido]-1-but-1-yne for (+/−)-3-(3-cyclopentyloxy-4methoxyphenyl)4[(N-butan-2-ol)-carboxamido]-1-phenylbut-1-yne, the title compound was prepared (80%) as a colorless oil. ¹H-NMR (400 MHz, CDCl₃) δ 9.53 (s, 1/2 H), 9.48 (s, 1/2 H), 6.88 (m, 3 H), 6.15 (br, 1 H), 4.80 (m, 1 H), 4.51 (dq, J=7, 7 Hz, 1 H), 4.15 (t, J=7 Hz, 1 H), 3.82 (s, 3 H), 2.64 (m, 2 H), 2.34 (d, J=2.4 Hz, 1 H), 1.8–2.0 (m, 6 H), 1.65 (m, 2 H), 1.37 (d, J=7.4 Hz, 1 1/2 H), 1.28 (d, J=7.4 Hz, 1 1/2 H) ppm.

81(c) S-3-(3-cyclopentyloxy-4-methoxyphenyl)4(4-methyloxazol-2-yl)-1-but-1-yne

Following the procedure for Example 77(c), except substituting S-3-(3-cyclopentyloxy-4-methoxyphenyl)4[(N-propan- 1-al-2-yl)-carboxamido]- 1-but- 1-yne for (+/−)-3-(3-cyclopentyloxy-4methoxyphenyl)4-[(N-butan-1-al-2-yl)-carboxamido]-1-phenylbut-1-yne, the title compound was prepared (45%) as a colorless oil. ¹H-NMR (400 MHz, CDCl₃) δ 7.27 (s, 1 H), 6.90 (dd, J=8.2, 2.0 Hz, 1 H), 6.86 (d, J=2.0 Hz, 1 H), 6.80 (d, J=8.2 Hz, 1 H), 4.73 (m, 1 H), 4.14 (m 1 H), 3.82 (s, 3 H), 3.15 (d AB quartets, Δppm=0.10, J=14.7, 9.6, 2 H), 2.29 (d, J=2.4 Hz, 1 H), 2.14 (d, J=1.1 Hz, 3 H), 1.8–2.0 (m, 6 H), 1.65 (m, 2 H) ppm.

81(d) S-3-(3-cyclopentyloxy-4-methoxyphenyl)4(4-methyloxazol-2-yl)-1-(3-methyl-[1,2,4]oxadiazol-5-ylphenyl)but-1-yne To a solution of 1-iodo-3-(3-methyl-[1.2,4]oxadiazol-5-yl)benzene (0.14 g, 0.5 mmol) and S-3-(3-cyclopentyloxy-4methoxyphenyl)-4-(4-methyloxazol-2-yl)-1-but-1-yne (0.15 g, 0.50 mmol) in tnethylamine (5 mL) under an argon atmosphere was added trace tetrakis(triphenylphosphine) palldium(0) and trace copper(I) iodide. The mixture was heated to 80° C. for 0.20 h, was cooled to room temperature and was concentrated in vacuo. Purification by flash chromatography (silica gel, 50%EtOAc/hexane) provided the titled compound (81%) as a yellow lass. ¹H-NMR (400 MHz, CDCl₃) δ 8.14 (d, J=1.2 Hz, 1 H), 8.03 (m, 1 H), 7.57 (m, 1 H), 7.45 (t, J=7.7 Hz, 1 H), 7.30 (d, J=1.2 Hz, 1 H), 6.97 (dd, J=8.3, 2.0 Hz, 1 H), 6.91 (d, J=2.0 Hz, 1 H), 6.84 (d, J=8.3 Hz, 1 H), 4.76 (m, 1 H), 4.36 (t, J=7.7 Hz, 1 H), 3.84 (s, 3 H), 3.35 (d AB quartets, Δppm=0.08, J=14.6, 8.9 Hz, 2 H), 2.47 (s, 3 H), 2.17 (d, J=1.3 Hz, 3 H), 1.8–2.0 (m, 6 H), 1.65 (m, 2 H) ppm. Anal (C₂₉H₂₉N₃O₄·0.5 H₂O) calcd: C, 70.71, H, 6.04, N, 8.53; C, 70.72, H, 5.70, N, 8.48.

Example 82

Preparation of (+/−)-1-(2-aminopyrimidin-5-yl)-3-(3-cyciopentyloxy4-methoxyphenyl)-4-(4-methyl oxazol-2-yl)but-1-yne 82(a) (+/−)-3-(3-cyclopentyloxy-4-methoxyphenyl)-4-[(N-propan-1-ol-2-yl)-carboxamido-1-but-1-yne Following the procedure for Example 74(a), except substituting 2-amino-1-propanol for 1-amino-2-butanol and substituting (+/−)-3-(3-cyclopentyloxy-4-methoxyphenyl)-3-propionic acid (SB 225588) for (+/−)-3-(3-cyclopentyloxy-4-methoxyphenyl)-3-phenylethynyl propionic acid (SB 225429) the crude title compound was prepared (89%) as a white foam, mp 54–59° C.

82(b) (+/−)-3-(3-cyclopentyloxy-4-methoxyphenyl)-4-[(N-propan-1-al-2-yl)-carboxamido]-1-phenylbut-1- yne Following the procedure for Example 74(b), except substituting (+/−)-3-(3-cyclopentyloxy-4-methoxyphenyl)-4-[(N-propan-1-ol-2-yl)-carboxamido]-1-but-1-yne for (+/−)-3-(3-cyclopentyloxy-4-methoxyphenyl)4([N-butan-2-ol)-carboxamido]-1-phenylbut-1-yne, the title compound was prepared (83%) as a colorless oil. ¹H-NMR (400 MHz, CDCl₃) δ 9.53 (s, 1/2 H), 9.48 (s, 1/2 H), 6.92 (m, 2 H), 6.82 (d, J=8.8 Hz, 1 H), 6.19 (m, 1 H), 4.77 (m, 1 H), 4.50 (dq, J=7.1, 7.1 Hz, 1 H), 3.82 (s, 3 H), 2.63 (m, 2 H), 2.34 (m, 1 H), 1.8–2.0 (m, 6 H), 1.65 (rn, 2 H), 1.37 (d, J=7.5 Hz, 1 1/2 H), 1.28 (d, J=7.5 Hz, 1 1/2 H) ppm.

82(c) (+/−)-3-(3-cyclopentyloxy-4-methoxyphenyl)-4-(4-methyloxazol-2-yl)-1-but-1-yne Following the procedure for Example 77(c), except substituting (+/−)-3-(3-cyclopentyloxy-4-methoxyphenyl)-4-[(N-propan-1-al-2-yl)-carboxamido]-1-but-1-yne for (+/−)-3-(3-cyclopentyloxy-4-methoxyphenyl)-4-[(N-butan-1-al-2-yl)-carboxamido]-1-phenylbut-1-yne, the title compound was prepared (43%) as a colorless oil. ¹H-NMR (400 MHz, CDCl₃) δ 7.27 (s, 1 H), 6.91 (dd, J=8.2, 1.8 Hz, 1 H), 6.86 (s, 1 H), 6.81 (d, J=8.2 Hz, 1 H), 4.73 (m, 1 H), 4.17 (m, 1 H), 3.82 (s, 3 H), 3.16 (d AB quartets, Δppm=0.10, J=14.7, 8.6 Hz, 2 H), 2.29 (m, 1 H), 2.15 (s, 3 H), 1.8–2.0 (m, 6 H), 1.65 (m, 2 H) ppm.

82(d) (+/−)-3-(3-cyclopentyloxy-4-methoxyphenyl)4(4-methyloxazol-2-yl)-1-(2-propionamidopyrimidin-5-yl)but-1-yne Following the procedure of Example 81(d), except substituting 5-bromo-2-propionamidopyrimidine for 1-iodo-3-(5-methyl-[1,2,4]oxadiazol-3-yl)benzene and substituting (+/−)-3-(3-cyclopentyloxy-4-methoxyphenyl)4(4-methyloxazol-2-yl)-1-but-1-yne for (+/−)-methyl-3-(3-cyclopentyloxy-4methoxyphenyl)-3-ethynylpropionate the title compound was prepared (31%) as a yellow lass. $^1$H-NMR (400 MHz, CDCl$_3$) δ 8.54 (s, 2 H), 8.18 (s, 1 H), 7.29 (s, 1 H), 6.93 (dd, J=8.3, 1.9 Hz, 1 H), 6.88 (d, J=1.9 Hz, 1 H), 6.84 (d, J=8.3 Hz, 1 H), 4.75 (m, 1 H), 4.37 (d, J=6.8 Hz, 1/2 H), 4.36 (d, J=7.9 Hz, 1/2 H), 3.83 (s, 3 H), 3.23 (d AB quartets, Δppm=0.07, J=14.6, 8.9 Hz, 2 H), 2.74 (q, J=7.5 Hz, 2 H), 2.15 (d, J=0.9 Hz, 3 H), 1.8–2.0 (m, 6 H), 1.65 (m, 2 H), 1.24 (t, J=7.5 Hz, 3 H) ppm.

82(e) (+/−)-1-(2-aminopyrimidin-5-yl)-3-(3-cyclopentyloxy-4-methoxyphenyl)4(4-methyloxazol-2-yl)but-1-yne To a suspension of sodium methoxide (0.12 g, 2.2 mmol) in methanol (20 mL) was added (+/−)-3-(3-cyclopentyloxy-4-methoxyphenyl)4(4-methyloxazol-2-yl)-1-(2-propionamidopyrimidin-5-yl)but-1-yne (0.29 g, 0.60 mmol). The mixture was heated at reflux for 1 h (forming a solution) and was cooled. Water was added and the mixture was extracted three times with dichloromethane, was dried (magnesium sulfate) and the solvent was evaporated and gave the titled compound (64%) as an off-white solid, mp 103–105° C. Anal (C$_{24}$H$_{26}$N$_4$O$_3$·0.6 H$_2$O) calcd: C, 67.15, H, 6.39, N, 13.05; C, 67.07, H, 6.22, N, 12.67.

Example 83

Preparation of (+/−)-2-[2-(cyclopentyloxy-4-methoxyphenyl)-4-phenylbut-ynyl]-5-methyl-2-oxazoline To a solution of (+/−)-3-(3-cyclopentyloxy-4-methoxyphenyl)-4-[(N-propan-2-ol)-carboxamido]-1-phenylbut-1-yne (0.56 g, 1.33 mmol) and triphenylphosphine (0.74 g, 2.66 mmol) in tetrahydrofuran (10 mL) at 0° C. under an argon atmosphere was dropwise added diisopropylazodicarboxylate (0.53 mL, 2.66 mmol) and stirring continued for 2 h at room temperature. The reaction was evaporated and purified by two flash chromatographies, eluted first with 35:65 ethyl acetate:hexanes, then with 25:75 ethyl acetate: hexanes to provide the title compound (0.19 g, 36%) as a yellow oil. $^1$H-NMR (400 MHz, CDCl$_3$) δ 7.41 (m, 2 H), 7.28 (m, 3 H), 7.00 (m, 2 H), 6.83 (d, J=8.5 Hz, 1 H), 4.79 (m, 1 H), 4.67 (m, 1 H), 4.26 (t, J=8.3 Hz, 1 H), 3.92 (m, 1 H), 3.83 (s, 3 H), 3.41 (m, 1 H), 2.80 (m, 2 H), 1.8–2.0 (m, 6 H), 1.65 (m, 2 H), 1.30 (m, 3 H) ppm. Anal (C$_{26}$H$_{29}$NO$_3$·1.4 H$_2$O) calcd: C, 72.84, H, 7.48, N, 3.27; found: C, 72.75, H, 7.09, N, 3.69.

Example 84

Preparation of (+/−)-3-(3-cyclopentyloxy-4-methoxyphenyl)4(3-methyl [1,2,4]thiadiazol-5-yl)-1-phenylbut- 1-yne A solution of (+/−)-3-(3-cyclopentyloxy-4-methoxyphenyl)-3-phenylethynyl propionic thioamide (0.12 g, 0.31 mmol) in dimethylacetamide dimethylacetal (1 mL) was stirred at room temperature under an argon atmosphere for 2.5 h, then evaporated. The residue was dissolved in ethanol (1 mL), to which was added pyridine (1 drop) and a solution of hydroxylarine-O-sulfonic acid (0.04 g, 0.34 mmol) in methanol (1 mL). The reaction was stirred at room temperature under an argon atmosphere for 2 h, then was diluted with 5% sodium carbonate, was extracted with ether, was washed with water, was dried (K$_2$CO$_3$) and was evaporated.

Purification first by flash chromatography eluted with 1:9 ethyl acetate:hexanes, then by thin layer chromatography, eluting five times with 1:99 acetone:toluene, followed by filtration through Celite washed with dichloromethane provided slihtly impure title compound (0.0006 g, 0.4%) as a colorless film. $^1$H-NMR (400 MHz, CDCl$_3$) δ 7.61 (d, J=7.5 Hz, 1 H), 7.35 (t, J=7.5 Hz, 2 H), 7.26 (m, 2 H), 6.86 (m, 2 H), 6.78 (s, lH), 4.78 (m, 1 H), 4.03 (t, J=7.7 Hz, 1 H), 3.85 (s, 3 H), 2.04 (d AB quartets, Δppm=0.I0, J=16.5, 7.8 Hz, 2 H), 2.01 (s, 3 H), 1.8-2.0 (m, 6 H), 1.65 (m, 2 H) ppm.

Example 85

Preparation of (+/−)-3-(3-cyclopentyloxy-4-methoxyphenyl)+(5-methyl [1,3,4]oxadiazol-2-yl)-1-phenylbut-1-yne 85(a) (+/−)-3-(3-cyclopentyloxy-4-methoxyphenyl)-3-phenylethynyl propionyl hydrazide To a solution of (+/−)-3-(3-cyclopentyloxy-4-methoxyphenyl)-3-phenylethynyl propionic acid (0.90 g, 2.47 mmol) and dimethyl formamide (3 drops) in dichloromethane (10 mL) at room temperature under an argon atmosphere was dropwise added oxalyl chloride (0.225 mL, 2.60 mmol), the reaction was stirred for 0.5 h and was evaporated. The residue was dissolved in tetrahydrofuran (5 mL) and added to a solution of triethylamine (0.69 mL, 4.94 mmol) and hydrazine monohydrate (0.60 mL, 12.4 mmol) in tetrahydrofuran (10 mL) at room temperature under an argon atmosphere. Water was added after 1 h and the reaction was extracted with 5/95 methanol/dichloromethane, dried (MgSO$_4$) and was evaporated. Purification by flash chromatography, eluted with 3:97 methanol:dichloromethane provided the title compound (0.47 g, 51%) as a white foamy solid, mp 44–46° C.

85(b) (+/−)-3-(3-cyclopentyloxy-4-methoxyphenyl)-3-phenylethynyl propionyl acylhydrazide To a solution of (+/−)-3-(3-cyclopentyloxy-4-methoxyphenyl)-3-phenylethynyl propionyl hydrazide (0.47 g, 1.25 mmol) in ethanol (5 mL) at room temperature under an argon atmosphere was added triethylamine (0.44 mL, 3.13 mmol) and acetic anhydride (0.22 mL, 2.25 mmol) and the reaction was stirred at reflux for 1 h. The reaction was cooled, was diluted with water, was three times extracted with 5/95 methanol/dichloromethane, was dried (MgSO$_4$) and was evaporated to provide the title compound (0.50 g, 95%) as a white solid, mp 136–139° C.

85(c) (+/−)-3-(3-cyclopentyloxy-4methoxyphenyl)4(5-methyl [1,3,4]oxadiazol-2-yl)- 1-phenylbut-1-yne A suspension of (+/−)-3-(3-cyclopentyloxy-4-methoxyphenyl)-3-phenylethynyl propionyl acylhydrazide (0.54 g, 1.29 mmol) and Lawesson's reagent (0.65 g, 1.61 mmol) in toluene (10 mL) was refluxed for 1 h under an argon atmosphere. The reaction was cooled, was diluted with sodium bicarbonate and water, was three times extracted with dichloromethane, was dried (MgSO$_4$) and was evaporated. Purification by numerous flash chromatographies provided the titled compound, (0.14 g, 28%), mp 105–106° C., Anal (C$_{25}$H$_{26}$N$_2$O$_3$·0.75 H$_2$O ) calcd: C, 72.18, H, 6.66, n, 6.73; found: C, 73.31, H, 6.39, N, 6.65.

Example 86

Preparation of (+/−)-3-(3-cyclopentyloxy-4-methoxyphenyl)4(5-methyl [1,3,4]thiadiazol-2-yl)-1-phenylbut-1-yne The titled compound was isolated by flash chromatography as a by product from the reaction mixture in Example 14(c) as a waxy amber solid (0.05 g, 9.5%), $^1$H-NMR (400 MHz, CDCl$_3$) δ 7.45 (m, 2 H), 7.33 (m, 3 H), 6.98 (dd, J=8.2,2.0 Hz, 1 H), 6.95 (d, J=2.0 Hz, 1 H), 6.84 (d, J=8.2 Hz, 1 H), 4.77 (m, 1 H), 4.25 (t, J=7.7 Hz, 1 H), 3.84 (s, 3 H), 3.58 (m, 2 H), 2.73 (s, 3 H), 1.8-2.0 (m, 6 H), 1.65 (m, 2 H) ppm. Anal (C$_{25}$H$_{26}$N$_2$O$_2$S·0.75 H$_2$O) calcd: C, 69.49, H, 6.41, N, 6.48; found, C, 69.27, H, 6.12, N, 6.41.

Example 87

Preparation of (+/−)-2-(2-[3-cyclopentyloxy-4-methoxyphenyl]4phenyl-3-butyn- 1-yl) 4methylimidazole 87(a) (+/−)-O-methyl-3-(3-cyclopentyloxy-4methoxyphenyl)-3-phenylethynylpropionimidate A stirred suspension of (+/−)-3-(3-cyclopentyloxy-4methoxyphenyl)-3-phenylethynylpropionic acid amide (0.83 g, 2.2 mmol) and anhydrous disodium hydrogen phosphate (3.12 g, 22.0 mmol) in dry methylene chloride (25 mL) at 0° C. was treated with trimethyloxonium fluoroborate (2.28 g, 15.4 mmol) in portions under argon. After 30 m, the mixture was allowed to warm to ambient temperature. The reaction mixture was rechilled after 3 h and quenched with an aqueous solution of sodium carbonate at 0° C. The organic phase was washed with cold water, dried and stored over anhydrous potassium carbonate at 5° C. Evaporation of the solvent afforded the titled compound as an oil. $^1$H NMR (400 MHz, CDCl$_3$) δ 7.43 (m, 2 H), 7.30 (m, 3 H), [6.98 (d, J=2.0 Hz)+6.97 (s) +6.94 (d, J=2.1 Hz)] ( 3H total), 6.84 (d, J=8.2 Hz, lH), 4.80 (m, 1 H), 4.19 (t, J=7.7 Hz, 1 H), 3.85 (s, 3 H), 3.78 (s, 3 H), 2.77 (d, 2 H), 1.50-2.00 (m, 10 H). MS-ES+(m/e) [M+H] 378.2, [M+H-C$_3$H$_7$NO] 305.2.

87b) (+/−)-2-(2-[3-cyclopentyloxy-4-methoxyphenyl] 4phenyl-3-butyn-1-yl)4methylimidazole.

A stirred solution of the (+/−)-O-methyl-3-(3-cyclopentyloxy-4-methoxyphenyl)-3-phenylethynylpropionimidate (64 mg, 0.17 mmol) and tosic acid (1.4 mg, 0.008 mmol, 5 mol %) in dry dioxane (1.6 mL) under argon heated to 100° C. was treated with a solution of proparylamine (9.5 mg, 0.17 mmol) in dioxane (1.0 mL) over 45 m. After 2 h a second portion of the amine (4.5 mg, 0.08 mmol) in dioxane (0.5 mL) was added over 20 m followed by 10 h additional heating. The solvent was removed to afford the titled compound as a dark resin. MS-ES+ (m/e) M+H] 401.2 base peak.

Example 88

Preparation of (+/−)-2-(2-[3-cyclopentyloxy-4-methoxyphenyl]4phenyl-3-butyn-1-yl)-1, 5dimethylimidazole 88(a) (+/−)-N,O-dimethyl-3-(3-cyclopentyloxy-4-methoxyphenyl)-3-phenylethynylpropionimidate A stirred suspension of (+/−)-N-methyl-3-(3-cyclopentyloxy-4-methoxyphenyl)-3-phenylethynylpropionic acid amide (113 mg, 0.30 mmol) and anhydrous disodium hydrogen phosphate (850 mg, 6.0 mmol) in dry methylene chloride (10 mL) at 0° C. was treated with trimethyloxonium fluoroborate (666 mg, 4.50 mmol) in portions under argon. After 10 m, the mixture was allowed to warm to ambient temperature. The reaction mixture was rechilled after 48 h and quenched into an aqueous solution of sodium carbonate at 0° C. The organic phase was washed with cold water, cold brine, dried and stored over anhydrous potassium carbonate at 5° C. Evaporation of the solvent afforded the titled compound as an oil. $^1$H NMR (400 MHz, CDCl$_3$) δ 7.42 (m, 2 H), 7.29 (m, 3 H), 6.97 (s)+ 6.96 (d, J=2.1 Hz) + 6.93 (d, J=2.1 Hz ( 2 H), 6.83 (d, J=8.2 Hz), 4.79 (m, 1 H), 4.21 (t, J=7.7 Hz, 1 H), 3.84 (s, 3 H), 3.67 (s-br, 3 H), 2.92 (s, 3 H), 2.84 (d-d, J=8.1 Hz, J=13.5 Hz, 1 H), 2.67 (d-d, J=7.5 Hz, J=13.5 Hz, 1 H), 1.50–2.00 (m, 12 H). MS-ES+(m/e) [M+H] 392.2, [M+H—C$_4$H$_9$NO] 305.2.

88(b) (+/−)-2-(2-[3-cyclopentyloxyfmethoxyphenyl] 4phenyl-3-butyn-1-yl)-1,5-dimethylimidazole.

A stirred solution of the (+/−)-N,O-dimethyl-3-(3-cyclopentyloxy-4-methoxyphenyl)-3-phenylethynylpropionimidate (63 mg, 0.16 mmol) and tosic acid (1.4 mg, 0.008 mmol, 5 mol %) in dry dioxane (1.6 mL) under argon heated to 100° C. was treated with a solution of proparylamine (9 mg, 0.16 mmol) in dioxane (1.0 mL) over 45 m. After 2 h a second portion of the amine (4.5 mg, 0.08 mmol) in dioxane (0.5 mL) was added over 20 m followed by 10 h additional heating. The solvent was removed and the residue purified by flash chromatography (silica, 3–4% methanol in methylene chloride) to afford the titled compound as a yellow resin (8.3%). $^1$H NMR (400 MHz, CDCl$_3$) δ 7.39 (m, 2 H), 7.30 (m, 3 H), 6.99 (d-d, J=8.2 Hz, J=2.0 Hz, 1 H), 6.83 (s) superimposed upon 6.88-6.78 (m, 3 H), 4.69 (m, 1 H), 4.36 (t, 1 H), 3.83 (s, 3 H), 3.29 (d-d, J=7.7, J=14.2 Hz, 1 H), 3.15 (s) superimposed upon 3.20–3.08 (m, 4 H), 2.13 (s, 3 H), 1.5–2.0 (m, 9 H). ). MS-ES+(m/e) [M+H] 415.1.

UTILITY EXAMPLES

EXAMPLE A

Inhibitory effect of compounds of Formula (I) on in vitro TNF production by human monocytes The inhibitory effect of compounds of Formula (I) on in vitro TNF production by human monocytes may be determined by the protocol as described in Bader et aL, EPO published Application 0 411 754 A2, Feb. 6, 1991, and in Hanna, WO 90/15534, Dec. 27, 1990.

EXAMPLE B

Two models of endotoxic shock have been utilized to determine in vivo TNF activity for the compounds of Formula (I). The protocol used in these models is described in Bader et al, EPO published Application 0 411 754 A2, Feb. 6, 1991, and in Hanna, WO 90/15534, Dec. 27, 1990.

The compound of Example 1 herein demonstrated a positive in vivo response in reducing serum levels of TNF induced by the injection of endotoxin.

EXAMPLE C

Isolation of PDE Isozymes

The phosphodiesterase inhibitory activity and selectivity of the compounds of Formula (I) can be determined using a battery of five distinct PDE isozymes. The tissues used as sources of the different isozymes are as follows: 1) PDE Ib, porcine aorta; 2) PDE Ic, guinea-pig heart; 3) PDE III, guinea-pig heart; 4) PDE IV, human monocyte; and 5) PDE V (also called "Ia"), canine trachealis. PDEs Ia, Ib, Ic and III are partially purified using standard chromatographic techniques [Torphy and Cieslinski, Mol. Pharmacol., 37:206–214, 1990]. PDE IV is purified to kinetic homoeneity by the sequential use of anion-exchange followed by heparin-Sepharose chromatography [Torphy et al., J. Biol. Chem., 267:1798–1804, 1992].

Phosphodiesterase activity is assayed as described in the protocol of Torphy and Cieslinski, Mol. Pharmacol., 37:206–214, 1990. Positive IC$_{50's}$ in the nanomolar to μM range for compounds of the workings examples described herein for Formula (I) have been demonstrated.

What is claimed is:
1. A compound of Formula (I)

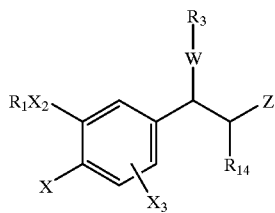

wherein:
R$_1$ is —(CR$_4$R$_5$)$_n$C(O)O(CR$_4$R$_5$)$_m$R$_6$, —(CR$_4$R$_5$)$_n$C(O)NR$_4$(CR$_4$R$_5$)$_m$R$_6$, —(CR$_4$R$_5$)$_n$O(CR$_4$R$_5$)$_m$R$_6$, or —(CR$_4$R$_5$)$_r$R$_6$ wherein the alkyl moieties unsubstituted or substituted with one or more halogens;

m is 0 to 2;

n is 1 to 4;

r is 0 to 6;

R$_4$ and R$_5$ are independently selected hydrogen or C$_{1-2}$ alkyl;

R$_6$ is hydrogen, methyl, hydroxyl, aryl, halo substituted aryl, aryloxyC$_{1-3}$ alkyl, halo substituted aryloxyC$_{1-3}$ alkyl, indanyl, indenyl, C$_{7-11}$ polycycloalkyl, tetrahydrofuranyl, furanyl, tetrahydropyranyl, pyranyl, tetrahydrothienyl, thienyl, tetrahydrothiopyranyl, thiopyranyl, C$_{3-6}$ cycloalkyl, or a C$_{4-6}$ cycloalkyl containin one or two unsaturated bonds, wherein the cycloalkyl or heterocyclic moiety is unsubstituted or substituted by 1 to 3 methyl groups, one ethyl group, or an hydroxyl group;

provided that:
(a) when R$_6$ is hydroxyl, then m is 2; or
(b) when R$_6$ is hydroxyl, then r is 2 to 6; or
(c) when R$_6$ is 2-tetrahydropyranyl, 2-tetrahydrothiopyranyl, 2-tetrahydrofuranyl, or 2-tetrahydrothienyl, then m is 1 or 2; or
(d) when R$_6$ is 2-tetrahydropyranyl, 2-tetrahydrothiopyranyl, 2-tetrahydrofuranyl, or 2-tetrahydrothienyl, then r is 1 to 6;
(e) when n is 1 and m is 0, then R$_6$ is other than H in —(CR$_4$R$_5$)$_n$O(CR$_4$R$_5$)$_m$R$_6$;

X is YR$_2$, fluorine, NR$_4$R$_5$, or formyl amine;

Y is O or S(O)$_{m'}$;

m' is 0, 1, or 2;

X$_2$ is O or NR$_8$;

X$_3$ is hydrogen or X;

R$_2$ is independently selected from —CH$_3$ or —CH$_2$CH$_3$ optionally substituted by 1 or more halogens;

W is alkynyl of 2 carbon atoms;

R$_3$ is H or R$_7$;

Z is C(O)R$_{13}$, (CH$_2$)$_{0-1}$C(O)OR$_{13}$, (CH$_2$)$_{0-1}$C(O)NR$_{10}$R$_{13}$, (CH$_2$)$_{0-1}$C(R$_8$R$_8$)OR$_8$, —NHC(O)R$_7$, (CH$_2$)$_{0-1}$NR$_{10}$R$_{13}$, NH[C(O)C(O)OR$_8$], CH$_2$NH[C(O)CNR$_{10}$R$_{13}$], CH$_2$S(O)qR$_7$, CH[S(O)qR$_7$]$_2$, dithiolane, (tetrazol-5-yl), thiazol-2-yl, [1,2,4]thiadiazol-5-yl, [1,3,4]oxadiazol-2-yl, imidazol-2-yl, oxazol-2-yl, or (3- or 5-oxadiazolyl[1,2,4]; wherein each of the heterocylic ring systems are unsubstituted or substituted one or more times by R$_9$; and wherein q is 0, 1 or 2;

R$_7$ is —(CR$_4$R$_5$)$_q$R$_{11}$ or C$_{1-6}$ alkyl wherein the R$_{11}$ or C$_{1-6}$ alkyl group is unsubstituted or substituted one or more times by methyl or ethyl unsubstituted or substituted by 1–3 fluorines, —NR$_8$R$_{10}$, —CO$_2$R$_8$, —O(CH$_2$)$_q$R$_8$, —NR$_8$C(O)R$_8$ or R$_{12}$;

q is 0, 1, or 2;

R$_8$ is independently selected from hydrogen or R$_9$;

R is C$_{1-4}$ alkyl optionally substituted by one to three fluorines;

R$_{10}$ is OR$_8$ or R$_8$;

R$_{11}$ is pyrimidyl, (1- or 2-imidazolyl), or phenyl;

R$_{12}$ is oxadiazolyl, or thiadiazolyl, and each of these heterocyclic rings is connected throuh a carbon atom and each may be unsubstituted or substituted by one or two C$_{1-2}$ all groups unsubstituted or substituted by one to three fluorines;

R$_{13}$ is hydrogen or R$_7$; or when R$_{10}$ and R$_{13}$ are as NR1OR13 they may toether with the nitroen form a 5 to 7 membered ring comprised of carbon or carbon and one or more additional heteroatoms selected from O, N, or S, wherein the additional nitroen heteroatom may be unsubstituted or substituted by one or two C$_{1-2}$ alkyl groups unsubstituted or substituted by one to three fluorines;

R$_{14}$ is hydrogen, C(O)R$_{13}$, C(O)OR$_{13}$, C(O)NR$_{10}$R$_{13}$, OR$_8$, or S(O)$_q$R$_7$ where q is 0, 1 or 2;

or the pharmaceutically acceptable salts thereof.

2. A compound of claim 1 wherein R$_1$ is —CH$_2$-cyclopropyl, —CH$_2$—C$_{5-6}$ cycloalkyl, —C$_{4-6}$ cycloalkyl unsubstituted or substituted with OH, X is YR$_2$, and Z is tetrazol-5-yl, C(O)R$_{13}$, C(O)OR$_{13}$, C(O)NR$_{10}$R$_{13}$) or (3- or 5-oxadiazolyl[1,2,4].

3. A compound of claim 1 or 2 which is (+/−)-methyl-(3-cyclopentyloxy-4-methoxyphenyl)-3-phenylethynylpropionate;

(+/−)-methyl-3-(3-cyclopentyloxy-4-methoxyphenyl)-7-hydroxyhept-4-ynoate;

(+/−)-methyl-3-(3-cyclopentyloxy-4-methoxyphenyl)-8-hydroxyoct4-ynoate;

(+/−) methyl-3-(3-cyclopentyloxy-4-methoxyphenyl) non-4-ynoate;

(+/−)-3-(3-cyclopentyloxy-4-methoxyphenyl)-3-ethynylpropionic acid;

(+/−) methyl-3-(3-cyclopentyloxy-4-methoxyphenyl)-3-ethynylpropionate;

(+/−)-methyl-3-(3-cyclopentyloxy-4-methoxyphenyl)-3-[3-(5-methyl-[1,3,4]thiadiazol-2-yl)phenylethynyl] propionate;

(+/−)-3-(3-cyclopentyloxy-4-methoxyphenyl)-3[3-(5-methyl-[1,3,4]thiadiazol-2-yl)phenylethynyl]propionic acid;

(+/−)-methyl-3-(3-cyclopentyloxy-4-methoxyphenyl)-3-[3-(5-methyl-[1,3,4]oxadiazol-2-yl)phenylethynyl] propionate;

(+/−)-3-(3-cyclopentyloxy-4-methoxyphenyl)-3-[3-(5-methyl-[1,3,4]oxadiazol-2-yl)phenylethynyl]propionic acid;

(+/−)-methyl-3-(3-cyclopentyloxy-4-methoxyphenyl)-3-[3-(5-methyl-[1,2,4]oxadiazol-3-yl)phenylethynyl] propionate;

(+/−)-methyl 3-(3-cyclopentyloxy-4-methoxyphenyl)-3-(imidazol-2-ylethynyl) propionate;

(+/−)-methyl 3-(2-acetamidopyrimidin-5-ylethynyl)-3-(3-cyclopentyloxy-4-methoxyphenyl) propionate;

(+/−)-methyl 3-(2-aminopyrimidin-5-ylethynyl)-3-(3-cyclopentyloxy-4-methoxyphenyl) propionate;

(+/−)-methyl-3-(4-carboxyphenyl)ethynyl-3-(3-cyclopentyloxy-4-methoxyphenyl)propionate;

(+/−)-3-(3-cyclopentyloxy-4-methoxyphenyl)-3-phenylethynylpropionic acid amide;

(+/−)-N-methyl-3-(3-cyclopentyloxy-4-methoxyphenyl)-3-phenylethynylpropionic acid amide;

(+/−)-N,N-dimethyl-3-(3-cyclopentyloxy-4-methoxyphenyl)-3-phenylethynylpropionic acid amide;

(+/−)-N-[3-(3-cyclopentyloxy-4-methoxyphenyl)-3-phenylethynyl]propionylmorpholine;

(+/−)-N-methoxy-3-(3-cyclopentyloxy-4methoxyphenyl)-3-phenylethynylpropionic acid amide;

(+/−)-N-(thiazol-2-yl)-3-(3-cyclopentyloxy-4-methoxyphenyl)-3-phenylethynylpropionamide;

(+/−)-1-methyl4[2-(3-cyclopentyloxy-4methoxyphenyl)4phenylbut-3-ynoyl]piperazine, hydrochloride;

(+/−)-1,1-dimethyl[2-(3-cyclopentyloxy-4-methoxyphenyl)4phenylbut-3-ynoyl]piperazinium iodide;

(+/−)-N-methyl-N-(thiazol-2-yl)-3-(3-cyclopentyloxy-4methoxyphenyl)-3-phenylethynylpropionamide;

(+/−)-t-butyl-(3-cyclopentyloxy-4methoxyphenyl)-3-phenylethynylpropionate;

(+/−)-3-(3-cyclopentyloxy-4-methoxyphenyl)-5-phenylpent-4-ynol;

(+/−)4(3-cyclopentyloxy-4-methoxyphenyl)-6-phenylhex-5-yn-2-one;

(+/−)-3-[2-(3-cyclopentyloxy-4-methoxyphenyl)4phenylbut-3-ynyl]-5-methyl-1,2,4oxadiazole;

(+/−)-3-[2-(3-cyclopentyloxy-4methoxyphenyl)-4-phenylbut-3-ynyl]-5-trifluoromethyl-1,2,4-oxadiazole;

(+/−)-3-[2-(3-cyclopentyloxy-4-methoxyphenyl)4phenylbut-3-ynyl]-1,2,4 oxadiazole;

(+/−)-5-[2-(3-cyclopentyloxy-4-methoxyphenyl)4phenylbut-3-ynyl]tetrazole;

(+/−)-1-methyl-5-[2-(3-cyclopentyloxy-4-methoxyphenyl)Aphenylbut-3-ynyl]tetrazole;

(+/−)-methyl-3-(3-cyclopentyloxy-4-methoxyphenyl)-3-[3-(3-methyl-[1,2,4]oxadiazol-5-yl)phenylethynyl]propionate;

(+/−)-ethyl-3-(3-cyclopentyloxy-4-methoxyphenyl)-3-phenylethynylpropionate;

(+/−)-i-propyl-3-(3-cyclopentyloxy-4-methoxyphenyl)-3-phenylethynylpropionate;

(+/−)-n-propyl-3-(3-cyclopentyloxy-4-methoxyphenyl)-3-phenylethynylpropionate;

(+/−)-1-phenyl-3-(3-cyclopentyloxy-4-methoxyphenyl)-5-oxohexyne;

(+/−)-1-methoxy-3-(3-cyclopentyloxy-4-methoxyphenyl)-5-phenyl1-pentyne;

(+/−)-methyl4(3-cyclopentlyoxy-4-methoxyphenyl)-4-phenylethynylbutyrate;

(+/−)4-(3-cyclopentlyoxy-4-methoxyphenyl)-6-phenylhex-5-ynoic acid;

(+/−)-1-phenyl-3-(3-cyclopentyloxy-4-methoxyphenyl)-5-oxo-6-hydroxyhexyne;

(+/−)-1-phenyl-3-(3-cyclopentyloxy-4-methoxyphenyl)-5-oxo-6-methoxyhexyne;

(+/−)-methyl-2-carbomethoxy-3-(3-cyclopentyloxy-4-methoxyphenyl)-5-phenylpent4ynoate;

(+/−)-methyl-3-(3-cyclopentyloxy-4methoxyphenyl)-2-methyl-5-phenylpent4-ynoate;

(+/−)-methyl-3-(3-cyclopentyloxy-4-methoxyphenyl)-2-thiomethyl-5-phenylpent4-ynoate;

(R)-methyl-3-(3-cyclopentyloxy-4methoxyphenyl)-3-ethynylpropionate;

(S)-methyl-3-(3-cyclopentyloxy-4-methoxyphenyl)-3-ethynylpropionate;

(R)-methyl-3-(3-cyclopentyloxy-4-methoxyphenyl)-3-phenylethynylpropionate;

(S)-methyl-3-(3-cyclopentyloxy-4-methoxyphenyl)-3-phenylethynylpropionate;

(R)-3-(3-cyclopentyloxy-4methoxyphenyl)-3-ethynylpropionic acid;

(S)-methyl-3-(3-cyclopentyloxy-4-methoxyphenyl)-5-[3-(3-methyl[1,2,4]oxadiazol-5-yl)phenyllpent4ynoate;

(S)-methyl 3-(3-cyclopentyloxy-4-methoxyphenyl)-3-(fluoren-2-ylethynyl)propionate;

(S)-methyl 3-(3-cyclopentyloxy-4-methoxyphenyl)-3-(3-methyl-4-N-phthalimidophenylethynyl)propionate;

(S)-methyl 3-(3-cyclopentyloxy-4-methoxyphenyl)-3-(4-methoxyethoxymethylphenylethynyl)propionate;

(S)-methyl 3-(3-cyclopentyloxy-4-methoxyphenyl)-3-(4-N-veratrylaminophenylethynyl)propionate;

(S)-methyl 3-(3-cyclopentyloxy-4-methoxyphenyl)-3-(naphthalen-2-ylethynyl)propionate;

(S)-methyl 3-(3-cyclopentyloxy-4-methoxyphenyl)-3-(10,10-dioxo-phenoxathiin-2-ylethynyl)propionate;

(S)-methyl 3-(3-cyclopentyloxy-4methoxyphenyl)-3-(1-acetylindolin-5-ylethynyl)propionate;

(S)-methyl 3-(3-cyclopentyloxy-4-methoxyphenyl)-3-(dibenzofuran-2-ylethynyl)propionate;

(S)-methyl 3-(3-cyclopentyloxy-4-methoxyphenyl)-3-(dibenzo-p-dioxin-2-ylethynyl)propionate;

(S)-methyl 3-(3-cyclopentyloxy-4-methoxyphenyl)-3-(4'-trifluoromethylbenzophenon-4-ylethynyl)propionate;

(S)-methyl 3-(3-cyclopentyloxy-4-methoxyphenyl)-3-(4-chloro-3-fluorophenylethynyl)propionate;

(S)-methyl 3-(3-cyclopentyloxy-4-methoxyphenyl)-3-(3-chloro-4-fluorophenylethynyl)propionate;

(S)-methyl 3-(3-cyclopentyloxy-4-methoxyphenyl)-3-(3,4,difluorophenylethynyl)propionate;

(S)-methyl 3-(3-cyclopentyloxy-4methoxyphenyl)-3-(3,5,-dinitrophenylethynyl)propionate;

(S)-methyl 3-(3-cyclopentyloxy-4-methoxyphenyl)-3-(4-difluoromethoxyphenylethynyl)propionate;

(S)-methyl 3-(3-cyclopentyloxy-4-methoxyphenyl)3-(4-t-butylphenylethynyl)propionate;

(S)-methyl 3-(3-cyclopentyloxy-4methoxyphenyI)-3-(3-fluoro-5-nitrophenylethynyl)propionate;

(S)-methyl 3-(3-cyclopentyloxy-4-methoxyphenyl)-3-(3-trifluoromethyl-phenylethynyl)propionate;

(S,S)-1,4Bis[3-(cyclopentyloxy-4-methoxypheny-4-methoxycarbonylbutynyl]benzene;

(S)-methyl 3-(3-cyclopentyloxy-4-methoxyphenyl)-3-(3-fluorophenylethynyl)propionate;

(S)-methyl 3-(3-cyclopentyloxy-4-methoxyphenyl)-3-(4-fluorophenylethynyl)propionate;

(S)-methyl 3-(3-cyclopentyloxy-4-methoxyphenyl)-3-(4-methoxyphenylethynyl)propionate;

(S)-methyl 3-(3-cyclopentyloxy-4methoxyphenyl)-3-(4-cyanophenylethynyl)propionate;

(S)-nmethyl 3-(3-cycIopenty1oxyy4-methoxypheny1)-3-[4-pyrrol-1-yl)phenylethynyllpropionate;

(S)-methyl 3-(3-cyclopentyloxyffmethoxyphenyl)-3-(3,5-bistrifluoromethylphenylethynyl)propionate;
(S)-methyl 3-(3-cyclopentyloxy-4-methoxyphenyl)-3-(2-formylftran-5-ylethynyl)propionate;
(S)-methyl 3-(3-cyclopentyloxy-4methoxyphenyl)-3-(naphthalen-1-ylethynyl)propionate;
(S)-methyl 3-(3-cyclopentyloxy-4-methoxyphenyl)-3-(3-cyanomethylphenylethynyl)propionate; SB-248025
(S)-methyl 3-(3-cyclopentyloxy-4-methoxyphenyl)-3-(4-nitrophenylethynyl)propionate;
(S)-methyl 3-(3-cyclopentyloxy-4-methoxyphenyl)-3-(3,5-dichlorophenylethynyl)propionate;
(S)-methyl 3-(3-cyclopentyloxy-4-methoxyphenyl)-3-(3,4-dichlorophenylethynyl)propionate;
(S)-methyl 3-(3-cyclopentyloxy-4-methoxyphenyl)-3-(3-chlorophenylethynyl)propionate;
(S)-methyl 3-(3-cyclopentyloxyAmethoxyphenyl)-3-(3-acetophenylethynyl)propionate;
(S)-methyl 3-(3-cyclopentyloxy-4-methoxyphenyl)-3-(4-acetophenylethynyl)propionate;
(S)-methyl 3-(3-cyclopentyloxy-4-methoxyphenyl)-3-(4-cyanomethylphenylethynyl)propionate;
(S)-methyl 3-(3-cyclopentyloxy-4-methoxyphenyl)-3-(3-methoxyphenylethynyl)propionate;
(S)-methyl 3-(3-cyclopentyloxy-4-methoxyphenyl)-3-(4-chlorophenylethynyl)propionate;
(S)-methyl 3-(3-cyclopentyloxy-4-methoxyphenyl)-3-(3-cyanophenylethynyl)propionate;
(S)-methyl 3-(3-cyclopentyloxy-4-methoxyphenyl)-3-(4[N-{2-(cyclohexylamino)acetamido}]phenylethynyl)propionate;
(S)-methyl 3-(3-cyclopentyloxy-4methoxyphenyl)-3-(4-[N-{2-(pyrrolidino)acetamido}]phenylethynyl)propionate;
(S)-methyl 3-(3-cyclopentyloxy-4-methoxyphenyl)-3-(4-[N-{2-(benzylamino)acetamido}]phenylethynyl)propionate;
(S)-methyl 3-(3-cyclopentyloxy-4-methoxyphenyl)-3-(2,4dimethyloxazol-3-ylethynyl)propionate;
(S)-methyl 3-(3-cyclopentyloxy-4-methoxyphenyl)-3-(4-trifluoromethoxyphenylethynyl)propionate;
(S)-methyl 3-(3-cyclopentyloxy-4-methoxyphenyl)-3-(3-triuoromethyl-4-acetamidophenyl)propionate,
(S)-methyl-3-(3-cyclopentyloxy-4methoxyphenyl)-5-[3-(5-methyl[1,2,4]oxadiazol-3-yl)phenyl]pent4fynoate;
(+/−)-methyl-3-(3-carbomethoxyphenyl)ethynyl-3-(3-cyclopentyloxy-4-methoxyphenyl)propionate;
(+/−)-methyl-3-(2-carbomethoxyphenyl)ethynyl-3-(3-cyclopentyloxy-4-methoxyphenyl)propionate;
(+/−)-methyl-3-(4carbomethxyphenyl)ethynyl-3-(3-cyclopentyloxy-4-methoxyphenyl)propionate;
(+/−)-3-(4carbomethxyphenyl)ethynyl-3-(3-cyclopentyloxy-4-methoxyphenyl)propionic acid;
(+/−)-3-(3-carbomethoxyphenyl)ethynyl-3-(3-cyclopentyloxy-4-methoxyphenyl)propionic acid;
(+/−)-3-(2-carbomethxyphenyl)ethynyl-3-(3-cyclopentyloxy-4-methoxyphenyl)propionic acid;
(+/−)4-Amino-3-(3-cyclopentyloxy-4-methoxyphenyl)-1-phenyl-1-butyne hydrochloride;
(+/−)-N-[2-(3-Cyclopentyloxy-4-methoxyphenyl)4-phenylbut-3-ynyl]acetamide;
(+/−)-N-[2-(3-Cyclopentyloxy-4-methoxyphenyl)-4-phenylbut-3-ynyl]-trifluoroacetamide;
(+,−)-methyl 2-(3-cyclopentyloxy-4-methoxyphenyl)+phenyl-but-3-ynyloxamate;
(+1-)-methyl 2-(3-cyclopentyloxy-4-methoxyphenyl)-4-phenyl-but-3-ynyloxamic acid;
(+/−)-methyl 2-(3-cyclopentyloxy-4-methoxyphenyl)-4-phenyl-but-3-ynyloxamide;
4-aminomethylcarbonylarnino-3-(3-cyclopentyloxy-4-methoxyphenyl)-1-phenyl-1-butyne cyclohexylsulfamate;
(+/−)-1-amino-3-(3-cyclopentyloxy-4-methoxyphenyl)-5-phenylpent-4-yne;
(+/−)-3-(3-cyclopentyloxy-4-methoxyphenyl)-5-phenyl-1-thiomethyl-pent4-yne;
(+/−)-3-(3-cyclopentyloxy-4-methoxyphenyl)-1-methylsulfoxyl-5-phenyl-pent-4-yne;
(+/−)-3-(3-cyclopentyloxy-4methoxyphenyl)-1-methylsulfonyl-5-phenyl-pent-4-yne;
(+/−)-5,5-bis-methylthio-3-(3-cyclopentyloxy-4-methoxyphenyl)-1-phenyl-1-pentyne;
(+/−)-1-(1,3-dithiolane)-3-(3-cyclopentyloxy-4-methoxyphenyl)-1-phenyl-1-pentyne;
(+/−)-1-(1,3-dithiolane)-3-(3-cyclopentyloxy-4-methoxyphenyl)-5-[3-(5-methyl[1,2,4]oxadiazol-3-yl)phenyl]-1-pentyne;
(+/−)-2-[2-(3-cyclopentyloxy-4-methoxyphenyl)phenylbut-3-ynyl]-5-methylthiazole;
(+/−)-2-[2-(3-cyclopentyloxy-4-methoxyphenyl)-4-phenylbut-3-ynyl]-4-methylthiazole;
(+1-)-3-(3-cyclopentyloxy-4-methoxyphenyl)-4-(5-ethyloxazol-2-yl)-1-phenylbut-1-yne;
(+1-)-3-(3-cyclopentyloxy-4-methoxyphenyl)4-(5-methyloxazol-2-yl)-1-phenylbut-1-yne;
(+1-)-3-(3-cyclopentyloxy-4- methoxyphenyl)4(4,5-dimethyloxazol-2-yl)-1-phenylbut-1-yne;
(+/−)-3-(3-cyclopentyloxy-4-methoxyphenyl)4(4-ethyloxazol-2-yl)-1-phenylbut-1-yne;
(+/−)-3-(3-cyclopentyloxy-4-methoxyphenyl)(4-methyloxazol-2-yl)-1-phenylbut-1-yne;
(+/−)-3-(3-cyclopentyloxy-4-methoxyphenyl)(4-trifiuoroethyloxazol-2-yl)-1-phenylbut-1-yne;
(S)-3-(3-cyclopentyloxy-4-methoxyphenyl)4(4-methyloxazol-2-yl)-1-(5-methyl-[1,2,4]oxadiazol-3-ylphenyl)but-1-yne;
(S)-3-(3-cyclopentyloxy-4-methoxyphenyl)4(4-methyloxazol-2-yl)-1-(3-methyl-[1,2,4]oxadiazol-5-ylphenyl)but-1-yne;
(+/−)- 1-(2-aminopyrimidin-5-yl)-3-(3-cyclopentyloxy-4-methoxyphenyl)-4-(4-methyl oxazol-2-yl)but-1-yne;
(+/−)-2-[2-(cyclopentyloxy-4-methoxyphenyl)-4-phenylbut-ynyl]-5-methyl-2-oxazoline;
(+/−)-3-(3-cyclopentyloxy-4-methoxyphenyl)4(3-methyl [1,2,4]thiadiazol-5-yl)-1-phenylbut-1-yne;
(+/−)-3-(3-cyclopentyloxy-4-methoxyphenyI)4(5-methyl [1,3,4]oxadiazol-2-yl)-1-phenylbut-1-yne;
(+/−)-3-(3-cyclopentyloxy-4-methoxyphenyl)4(5-methyl [1,3,4]thiadiazol-2-yl)-1-phenylbut-1-yne;
(+/−)-2-(2-[3-cyclopentyloxy-4-methoxyphenyI]lphenyl-3-butyn-1-yl)4-methylimidazole;
(+/−)-2-(2-[3-cyclopentyloxy-4-methoxypheny]4phenyl-3-butyn-1-yl)-1,5-dimethylimidazole.

4. A pharmaceutical composition comprising a compound of Formula I according to claim 2 and a pharmaceutically acceptable excipient.

* * * * *